(12) United States Patent
Condado

(10) Patent No.: US 7,384,411 B1
(45) Date of Patent: Jun. 10, 2008

(54) MULTI-PURPOSE CATHETERS, CATHETER SYSTEMS, AND RADIATION TREATMENT

(75) Inventor: Jose Antonio R. Condado, Caracas (VE)

(73) Assignee: Condado Medical Devices Corporation, St. Paul, MN (US)

( * ) Notice: Subject to any disclaimer, the term of this patent is extended or adjusted under 35 U.S.C. 154(b) by 0 days.

(21) Appl. No.: 09/367,636

(22) PCT Filed: Feb. 19, 1998

(86) PCT No.: PCT/US98/03178

§ 371 (c)(1),
(2), (4) Date: May 25, 2000

(87) PCT Pub. No.: WO98/36790

PCT Pub. Date: Aug. 27, 1998

Related U.S. Application Data

(60) Provisional application No. 60/051,758, filed on Jul. 7, 1997, provisional application No. 60/040,455, filed on Mar. 14, 1997, provisional application No. 60/040,708, filed on Mar. 14, 1997, provisional application No. 60/038,231, filed on Feb. 19, 1997.

(51) Int. Cl.
*A61M 29/00* (2006.01)
*A61M 31/00* (2006.01)

(52) U.S. Cl. .................. 604/96.01; 604/101.01; 604/103.05

(58) Field of Classification Search .......... 604/96.01, 604/99.04, 100.01, 100.02, 101.01, 101.05, 604/102.03, 103.04, 103.07, 103.08, 103.01, 604/101.02, 104, 105, 106, 103.05, 103.06, 604/103.13; 606/108, 109, 192, 194; 623/1.11
See application file for complete search history.

(56) References Cited

U.S. PATENT DOCUMENTS

| 766,336 | A | * | 8/1904 | Farrington | ................... 604/104 |
|---|---|---|---|---|---|
| 845,249 | A | * | 2/1907 | Morris | ........................ 604/104 |
| 4,328,056 | A | * | 5/1982 | Snooks | ................... 604/101.02 |
| 4,423,725 | A | * | 1/1984 | Baran et al. | ............ 604/101.02 |
| 4,861,520 | A | | 8/1989 | van't Hooft et al. | .......... 252/644 |
| 4,883,459 | A | | 11/1989 | Calderon | ...................... 604/28 |
| 5,053,033 | A | | 10/1991 | Clarke | ........................... 606/3 |
| 5,199,939 | A | | 4/1993 | Dake et al. | ...................... 600/3 |
| 5,213,561 | A | | 5/1993 | Weinstein et al. | ............... 600/7 |
| 5,282,781 | A | | 2/1994 | Liprie | ........................... 600/3 |
| 5,354,257 | A | | 10/1994 | Roubin et al. | ................... 600/7 |
| 5,368,566 | A | * | 11/1994 | Crocker | ................. 604/101.02 |
| 5,378,237 | A | * | 1/1995 | Boussignac et al. | ..... 604/103.01 |
| 5,411,466 | A | | 5/1995 | Hess | ............................. 600/3 |
| 5,456,667 | A | | 10/1995 | Ham et al. | ................... 604/107 |
| 5,484,384 | A | | 1/1996 | Fearnot | ......................... 600/3 |
| 5,503,613 | A | | 4/1996 | Weinberger | ..................... 600/3 |
| 5,509,900 | A | | 4/1996 | Kirkman | ..................... 600/104 |
| 5,516,336 | A | | 5/1996 | McInnes et al. | .............. 606/194 |
| 5,531,662 | A | | 7/1996 | Carr | ................................ 600/2 |
| 5,536,250 | A | | 7/1996 | Klein et al. | .................... 604/96 |
| 5,540,659 | A | | 7/1996 | Teirstein | ..................... 604/104 |

(Continued)

*Primary Examiner*—Sharon Kennedy
(74) *Attorney, Agent, or Firm*—Andrews Kurth LLP

(57) ABSTRACT

Tis invention is new apparatuses and methods for treatments to be used from inside conduits or biological pathways. Examples of the biological pathways in which these new apparatuses and methods may be used include arteries, veins, and respiratory ways. Multi-purpose catheters (10) and catheter systems using structures including wires (2108), balloons (2150), and cords (2204) are described as well as methods to use such catheters and catheter systems. One of the embodiments is a configurable wire system which carries or transports radioactive sources. The wire is used in conjunction with a closed-end channel catheter.

45 Claims, 55 Drawing Sheets

U.S. PATENT DOCUMENTS

| | | | |
|---|---|---|---|
| 5,599,306 A * | 2/1997 | Klein et al. | 604/103.01 |
| 5,718,684 A * | 2/1998 | Gupta | 604/103.07 |
| 5,720,717 A | 2/1998 | D'Andrea | 604/21 |
| 5,759,172 A * | 6/1998 | Weber et al. | 604/103.07 |
| 5,782,740 A | 7/1998 | Schneiderman | 600/1 |
| 5,851,171 A | 12/1998 | Gasson | 600/3 |
| 5,855,546 A | 1/1999 | Hastings et al. | 600/3 |
| 5,910,101 A | 6/1999 | Andrews et al. | 600/3 |
| 5,938,582 A | 8/1999 | Ciamacco, Jr. et al. | 600/3 |
| 6,068,611 A * | 5/2000 | Loffler et al. | 604/101 |
| 6,398,708 B1 * | 6/2002 | Hastings et al. | 600/3 |

* cited by examiner

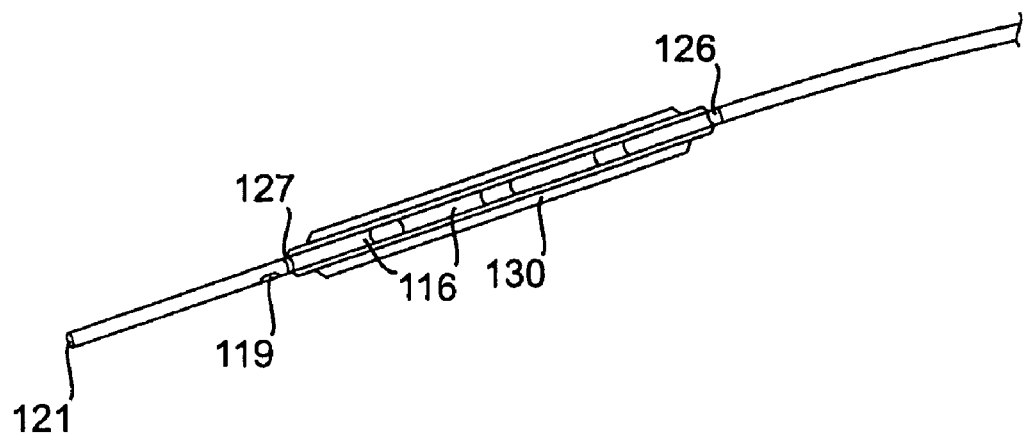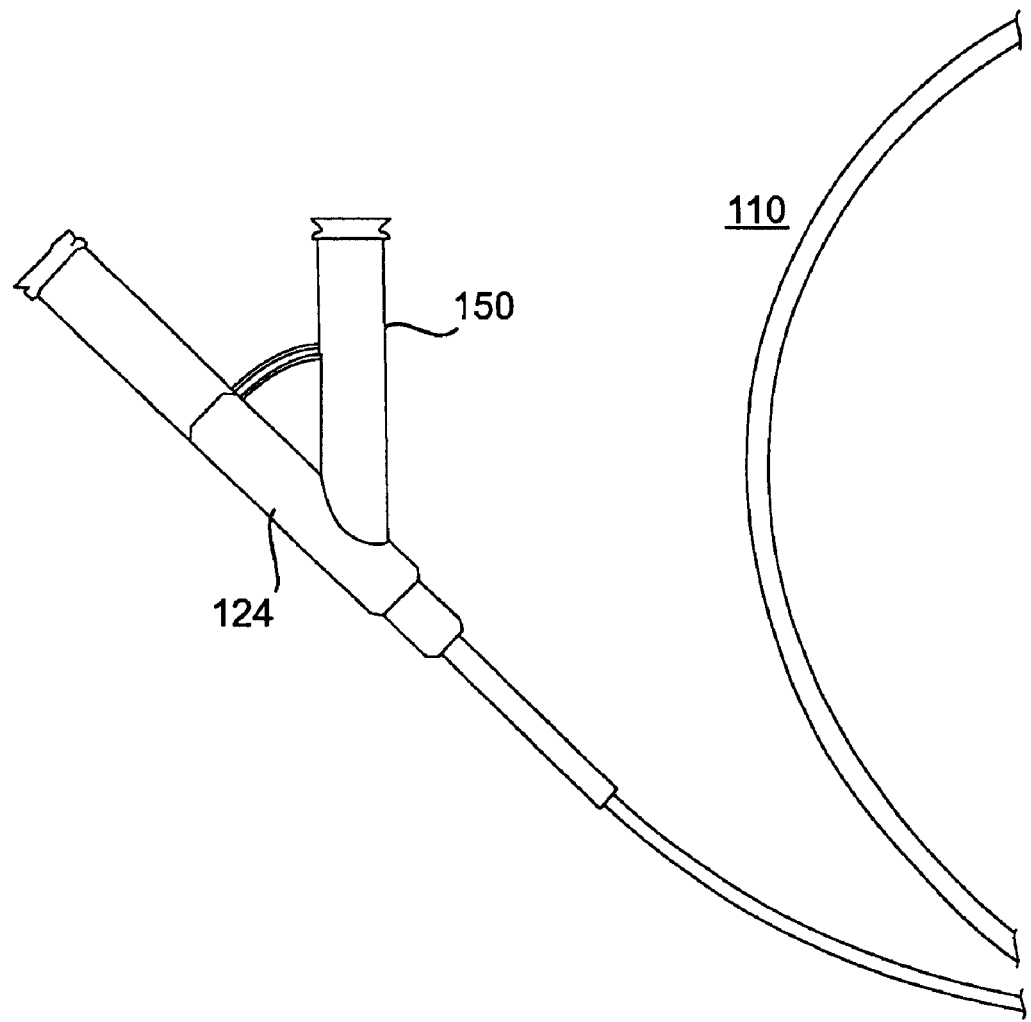
FIG. 4

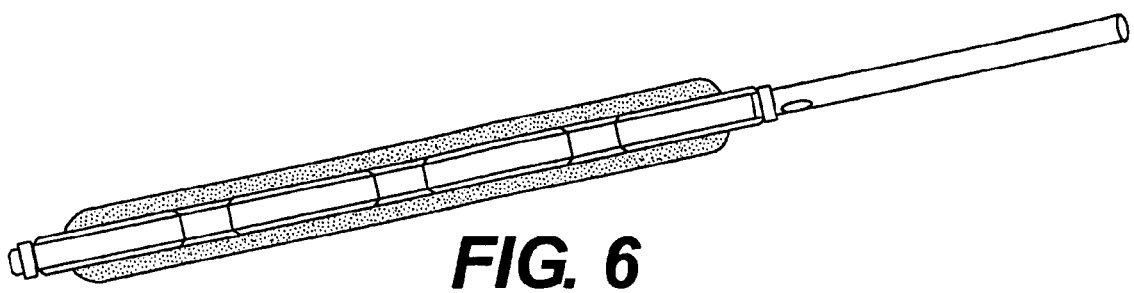
FIG. 6
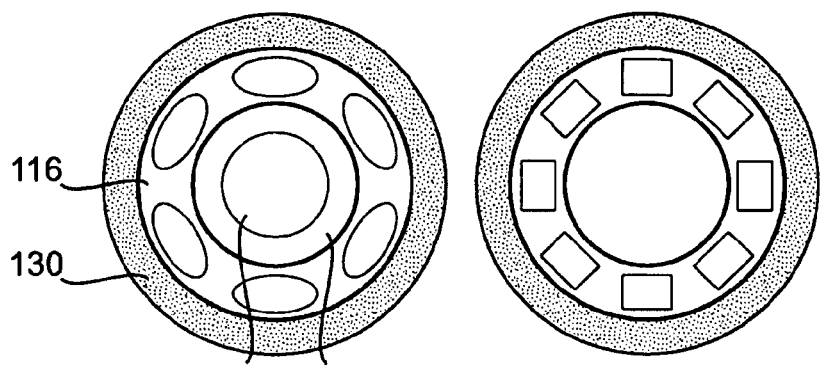
FIG. 6A  FIG. 6B
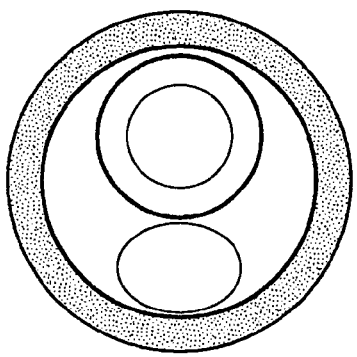 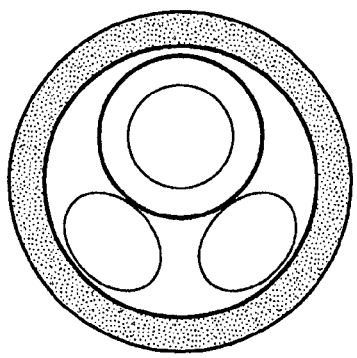 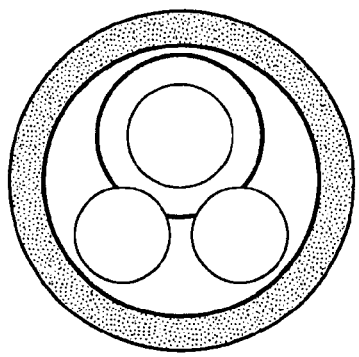
FIG. 6C  FIG. 6D  FIG. 6E
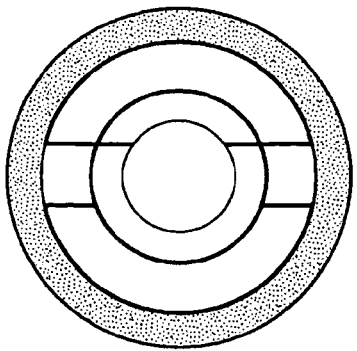 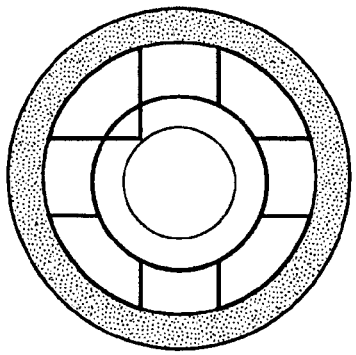 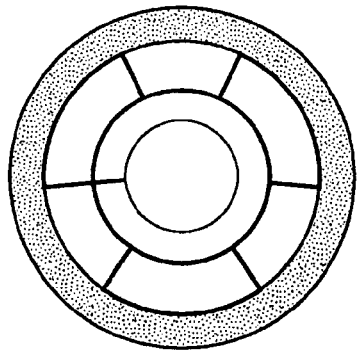
FIG. 6F  FIG. 6G  FIG. 6H

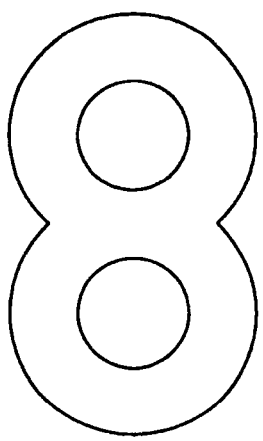
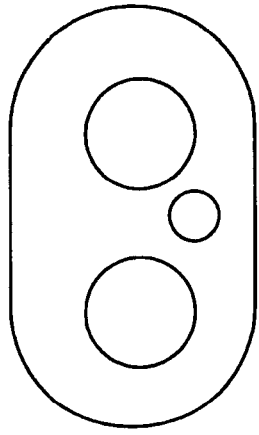
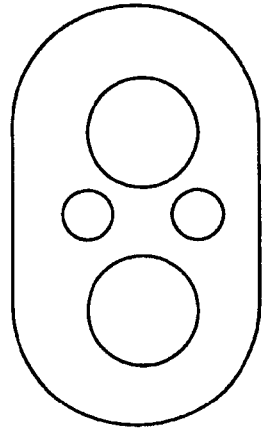
FIG. 9A  FIG. 9B  FIG. 9C
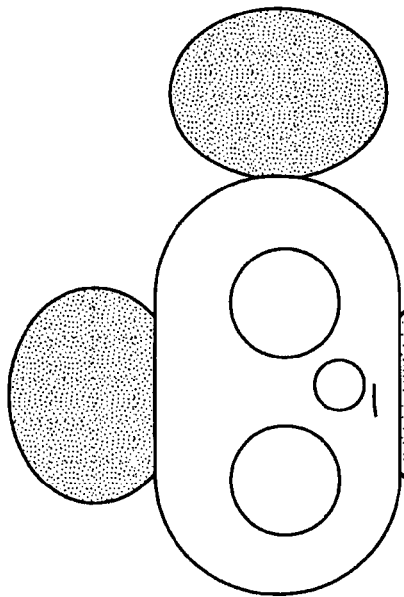
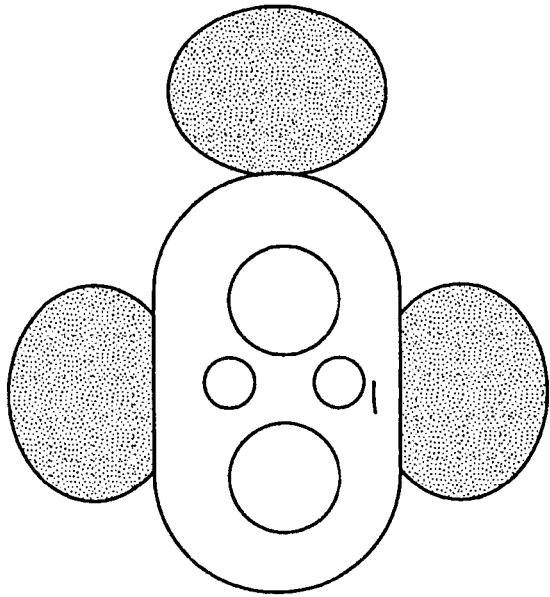
FIG. 9D  FIG. 9E
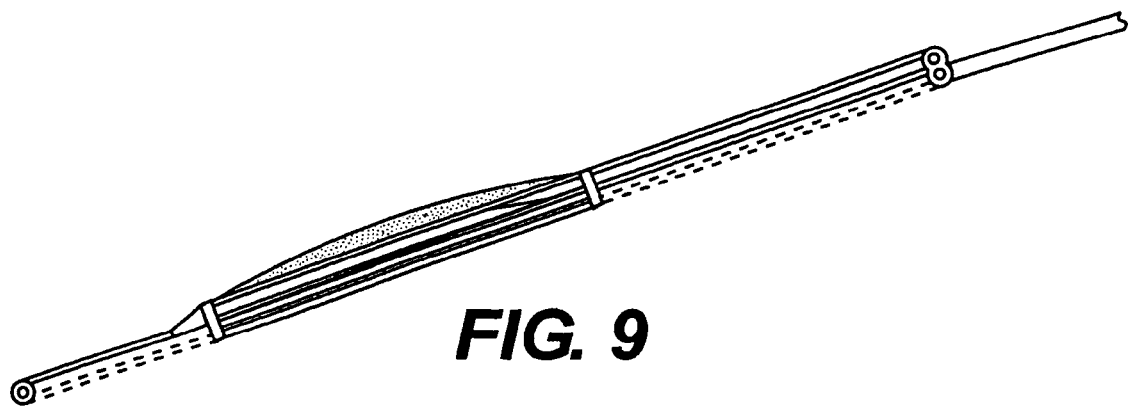
FIG. 9

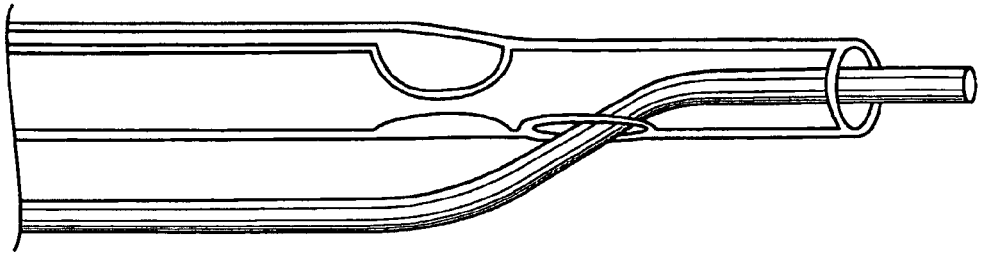
FIG. 13A
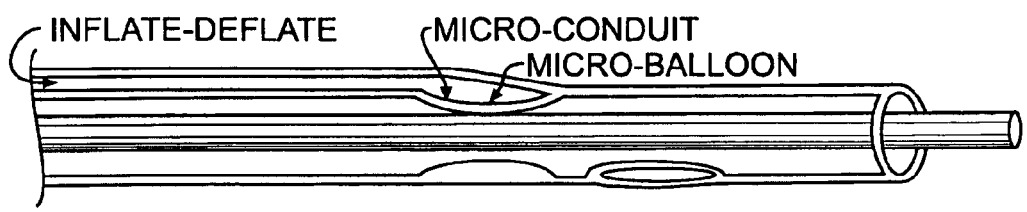
FIG. 13B
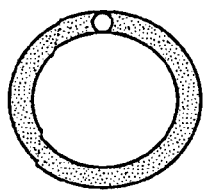 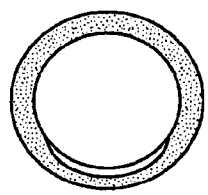 
FIG. 13C   FIG. 13D   FIG. 13E
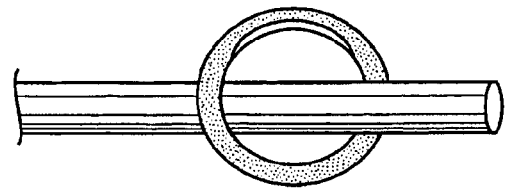
FIG. 13F

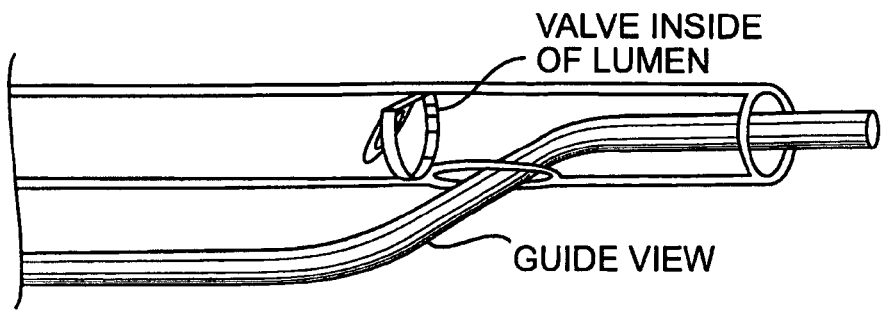
FIG. 14A
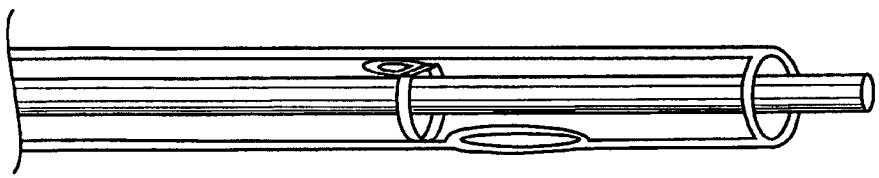
FIG. 14B
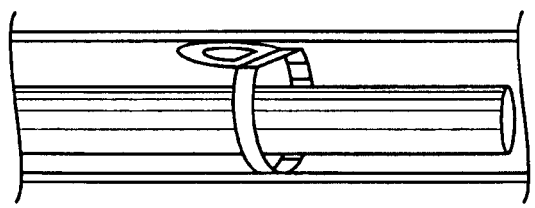 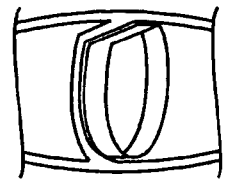
FIG. 14C  FIG. 14D
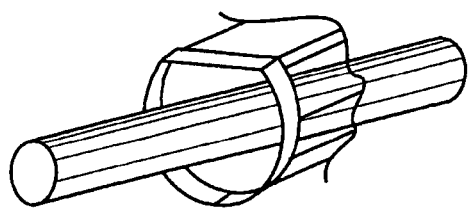 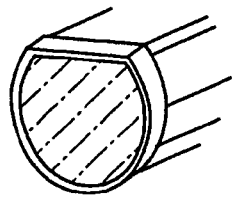
FIG. 14E  FIG. 14F

I-WIRE SYSTEMS

AO = AORTA
RC = RIGHT CORONARY
LC = LEFT CORONARY

PERFORMED LEFT WIRE

I-WIRE SYSTEMS

AO = AORTA
RC = RIGHT CORONARY
LC = LEFT CORONARY

II - BALLOON SYSTEMS

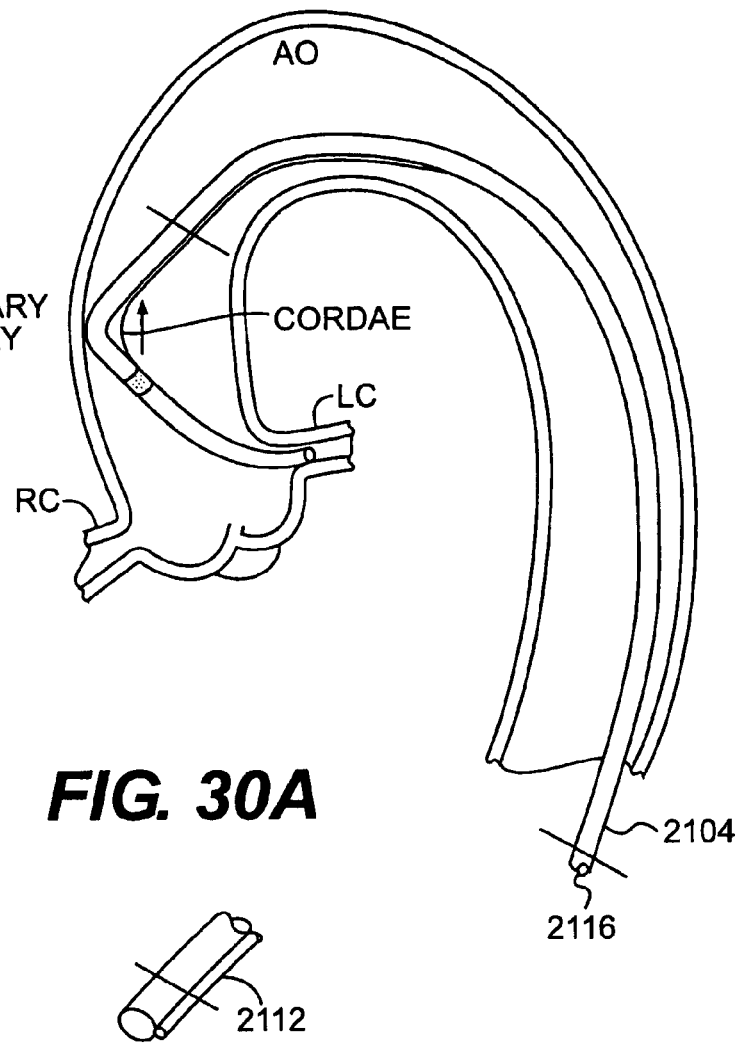
FIG. 30A
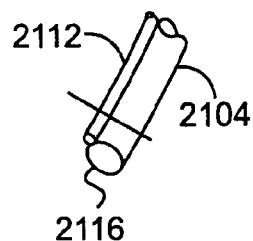
FIG. 30B
FIG. 30C

III - CORDAE SYSTEMS

AO = AORTA
RC = RIGHT CORONARY
LC = LEFT CORONARY

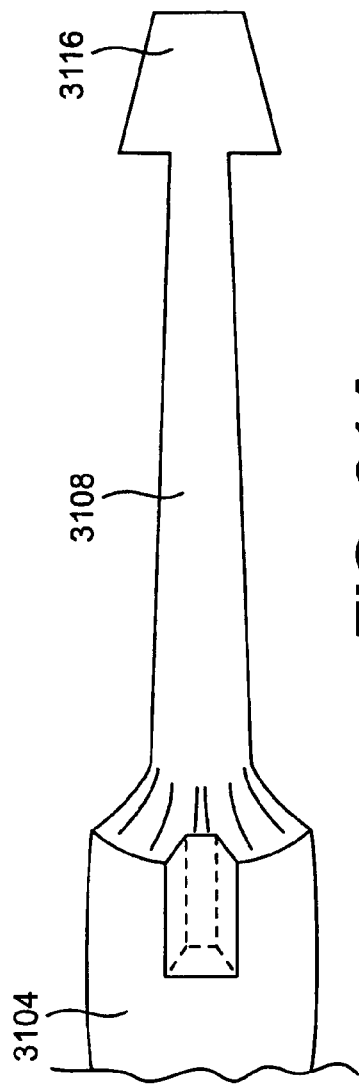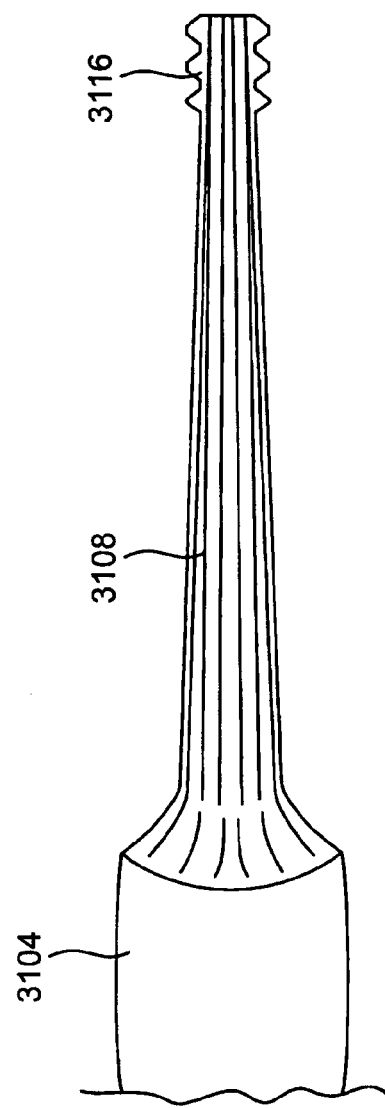

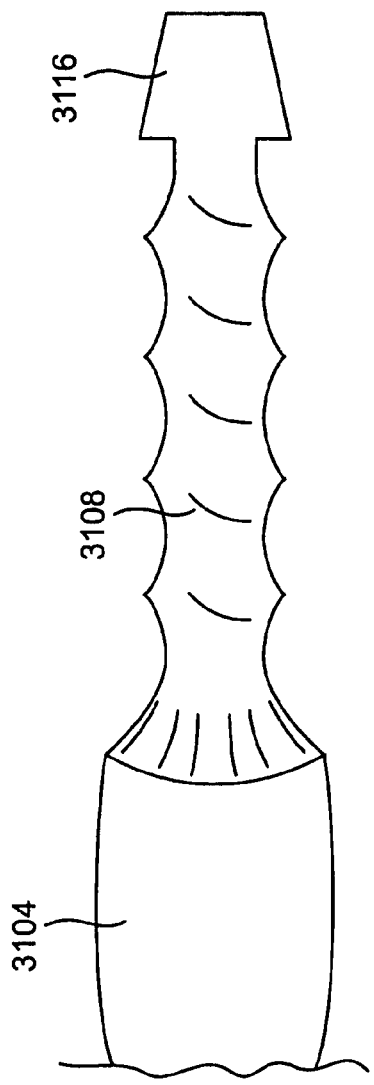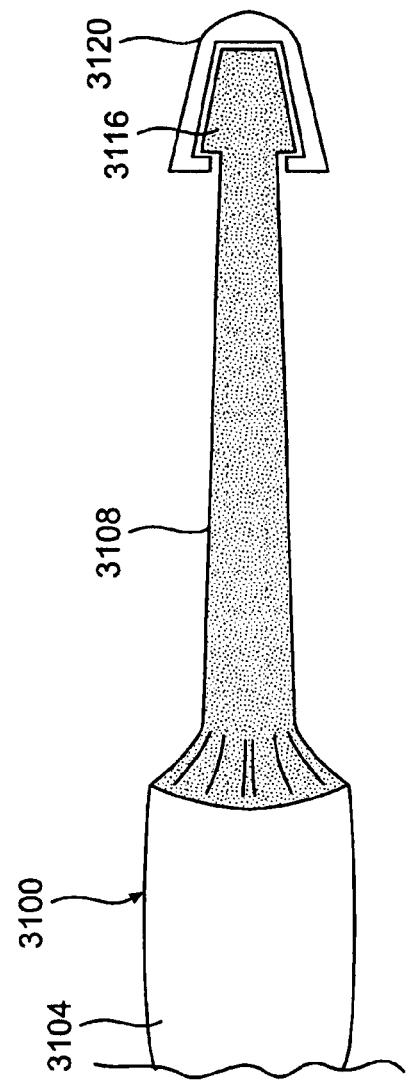

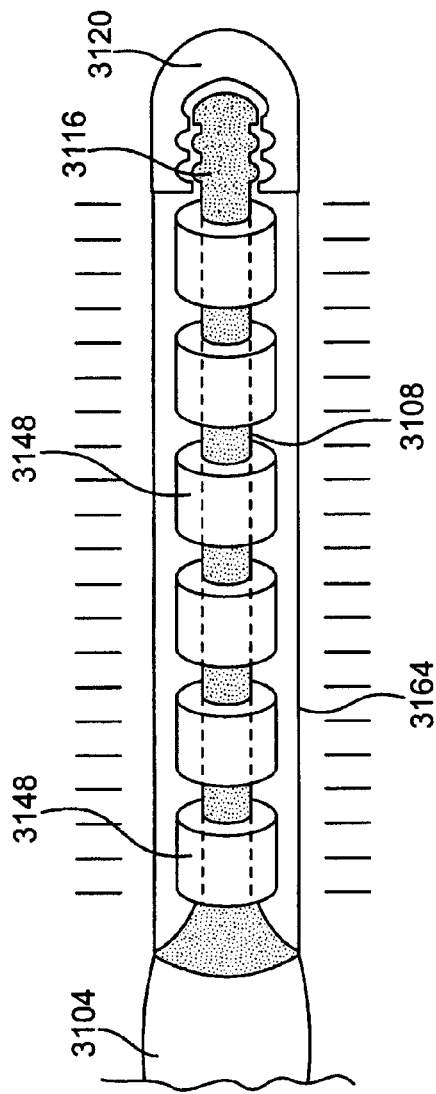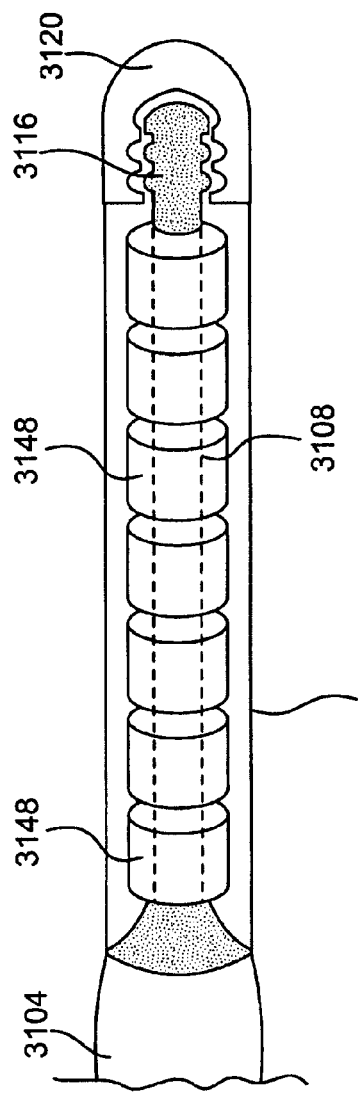

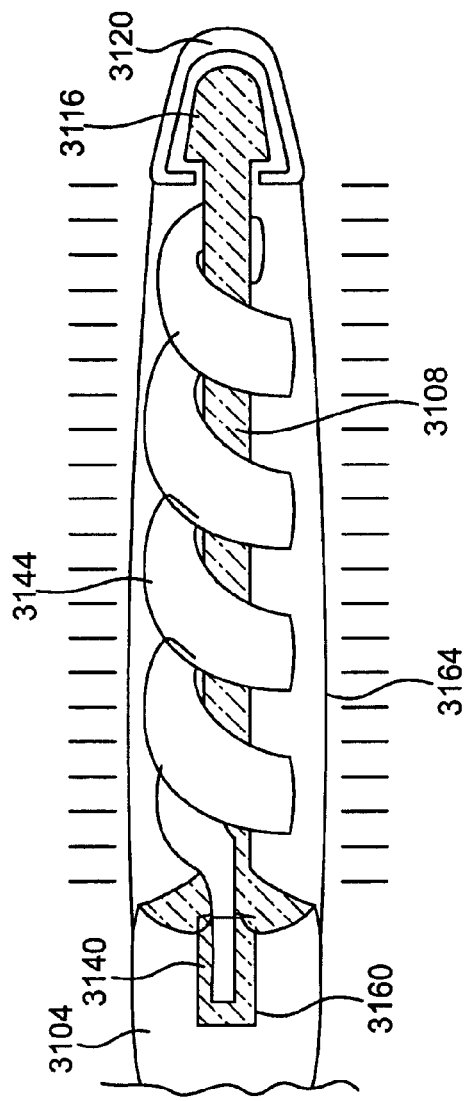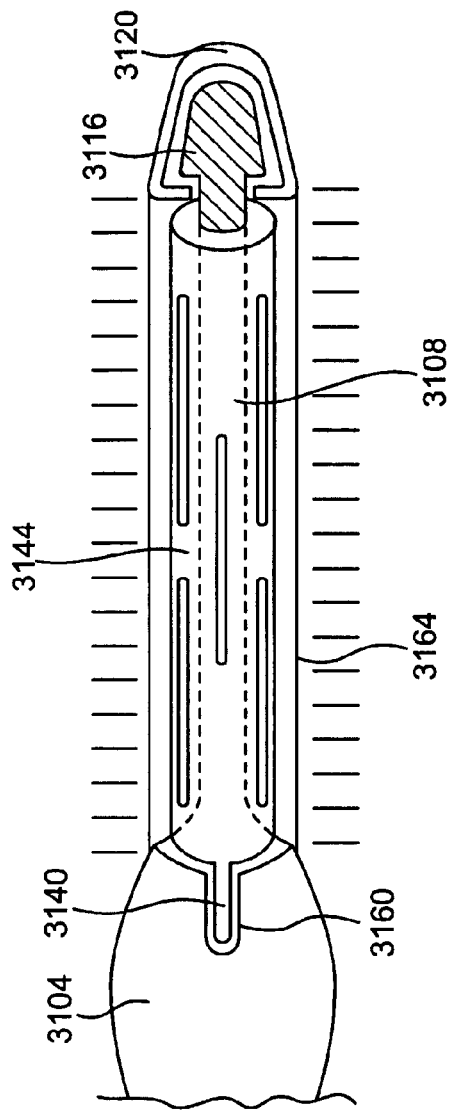

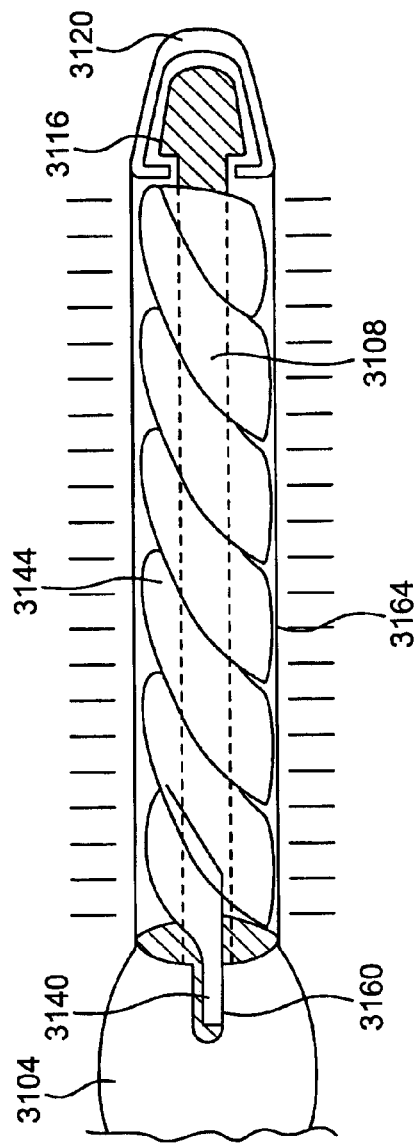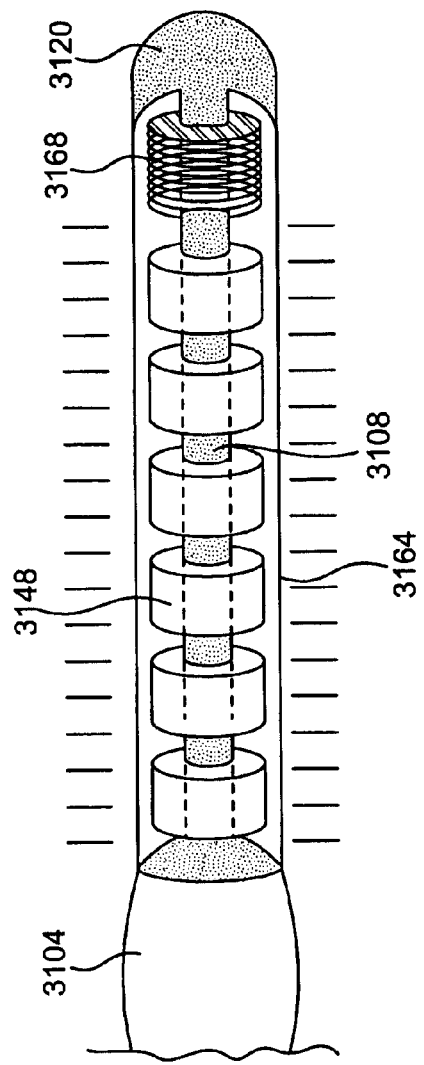

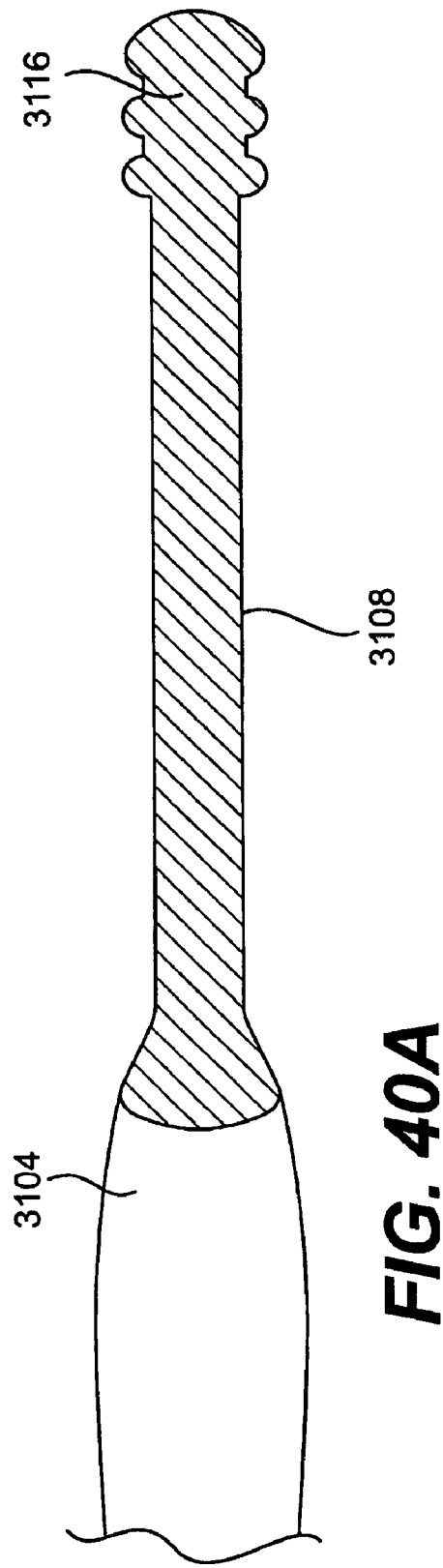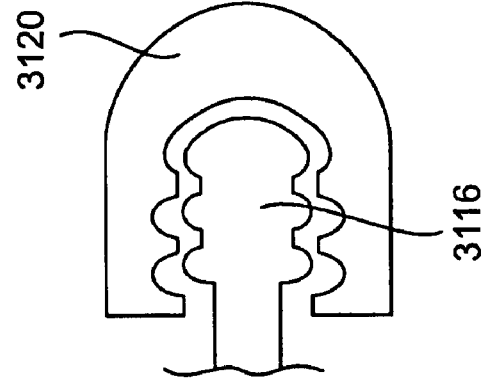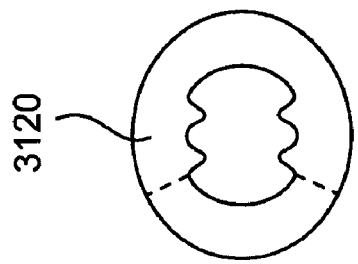
FIG. 40A
FIG. 40B
FIG. 40C

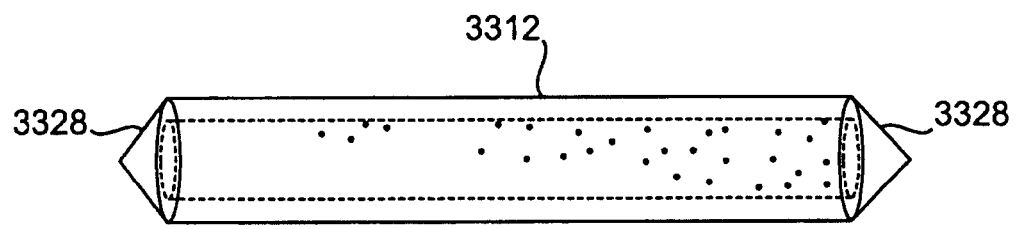
FIG. 46B
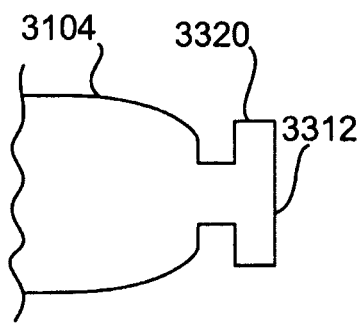 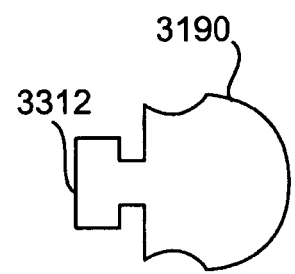
FIG. 46C      FIG. 46D

MULTI-PURPOSE CATHETERS, CATHETER SYSTEMS, AND RADIATION TREATMENT

RELATED APPLICATIONS

This application is related to the following applications which are each hereby incorporated by reference:

U.S. Provisional Application Ser. No. 60/038,231, entitled MULTI-PURPOSE CATHETER, filed on Feb. 19, 1997;

U.S. Provisional Application Ser. No. 60/040,708, entitled MULTI-PURPOSE CATHETER, filed on Mar. 14, 1997;

U.S. Provisional Application Ser. No. 60/040,455, entitled SYSTEMS FOR CATHETER MANIPULATION AND SUPPORT, filed on Mar. 14, 1997;

U.S. Provisional Application Ser. No. 60/051,758, entitled RADIOACTIVE SOURCE TRANSPORTING SYSTEMS FOR USE IN MEDICAL PROCEDURES, filed on Jul. 7, 1997;

International (PCT) Application Ser. No. PCT/US98/03178, entitled MULTI-PURPOSE CATHETERS, CATHETER SYSTEMS, AND RADIATION TREATMENT, filed Feb. 19, 1998.

TECHNICAL FIELD

The field of the invention is medical apparatuses and procedures for radiation treatment. This invention relates to catheters used to access anatomical spaces in humans and animals. The present invention to a catheter that may be used for perfusion, irradiation, dilation, and/or infusion of drugs and relates to systems for manipulating catheters in anatomical spaces and systems for providing structural support to catheters situated in anatomical spaces. This invention also relates to radiation treatment procedures.

BACKGROUND ART

The use of catheters to access the vascular system and other anatomical spaces has become a standard procedure in modern medicine. Catheters may be used for infusion of therapeutics, hyperalimentation, and other substances. Catheters can be used for the insertion or placement of substances or apparatuses for treating various disorders. Catheters can also be used to permit or enhance perfusion in humans and animals. Catheters may be used for specific purposes, such as irradiation or dilation. Similarly, catheters may be modified, e.g., by the addition of balloon systems, for specific purposes such as dilation.

Catheters used for many purposes may be inserted in relatively straight and/or relatively large vascular spaces or other anatomical spaces. Other catheters, however, must be inserted into relatively small and tortuous vascular spaces or tracts. In order to achieve proper placement of such catheters, the catheters must be manipulated or guided through the vascular system or other anatomical spaces.

The current invention is applicable to various catheters designed for multiple purposes for uses where the catheter must be manipulated or guided in order to serve its therapeutic purpose. Although the current invention applies to catheters designed for multiple purposes, the problem to be solved will be described in detail for catheters used to treat disorders of the vascular system and, in particular, disorders of the coronary artery system.

The first percutaneous arterial angioplasty took place in 1963 when a physician accidentally advanced an angiographic catheter through an occluded iliac artery, reestablishing flow. Subsequently, the physician began deliberately dilating peripheral arterial stenoses using a series of tapered catheters inserted percutaneously over a guidewire.

During the past 30 years, the procedure, which has become known as percutaneous transluminal angioplasty (PTA), has become an established procedure in the management of a variety of obstructive disorders of the vascular system. PTA has been applied to obstructive lesions of the iliac, femoral, renal, coronary and cerebral vascular systems. Theoretically, any vessel of sufficient size to allow atraumatic passage of a balloon catheter is suitable for PTA.

One use of PTA that exemplifies the problem solved by the current invention is the application of the procedure to disorders of the coronary circulation. PTA applied to coronary arteries is referred to as percutaneous transluminal coronary angioplasty (PTCA).

PTCA involves the inflation of a distensible balloon within a coronary stenosis and subsequent dilation of the narrowing. After baseline coronary angiography, a large-lumen guiding catheter is advanced to the appropriate coronary ostium. A small flexible guide wire is advanced through the guiding catheter into the coronary artery and across the stenosis. A balloon catheter is then advanced over the wire and positioned across the stenosis. The balloon is usually inflated with 6 to 12 atm of pressure for 30 to 120 seconds and then deflated.

During use of some catheters, the biological path in which treatment is occurring is occluded by the catheter. This occlusion is not desirable. A catheter that avoids interruption of the circulation through the treated segment is desirable. Another problem with current catheters is that they do not provide the doctor with the ability to control dosage of radiation by properly positioning the irradiation source from the area to be treated. The dosage of the ionizing radiation for causing a particular biological affect depends upon (1) the capability of the primary radiation source to emit the radiation, (2) the time of exposure, and (3) the distance from the source to the irradiation target. A catheter which maintains an uniform distance from the ionizing source introduced in the catheter to the tissue to be radiated, thereby allowing for proper radiation of the tissue is desirable. These and other problems in current catheter are addressed by the catheter of the present invention.

Low profile guiding catheters are expensive. They require expensive plastics, special manufacturing processes and cost generally in the $100 to $250 range per catheter. Furthermore, since the catheters are disposable this cost is per patient. Although other equipment used like the radiation source, guide wire, and automatic machine radiation source placing machine are very expensive, these components are reusable and are amortized over many years and many patients. Most catheters are specialized and can only be used for a specific medical procedure. They are not versatile or multi-purpose. Thus, in order to reduce costs, it would be desirable to have one catheter that would allow a doctor to perform a variety of procedures.

For many patients the percutaneous coronary angioplastics with balloon ("PTCA") or angioplastic procedure is not successful. PTCA without a stent or net has approximately a 50% first-time success rate. PTCA with a stent or net as approximately an 80% first-time success rate. Improvements in the catheters and in the procedure are necessary to prevent re-treatment and save money.

The major applications of the catheter are treatment of stenotic coronary veins and arteries as well as peripheral arteries (carotids, renal iliacs, femoral, popliteans). Each of these veins and arteries to be recanalized by any of the existing endovascular techniques (balloon angioplasty, atherectomy, laser evaporation) including cases when biological or metallic endovascular protesic devices are used, all of them causing a different degree of biological reaction of the vessel wall, that can result in new significant reduction of the vessel lumen (restenosis). A catheter that limits reduction of vessel lumen is desirable.

Ionizing radiation has been used in diagnostic, therapeutic, and other medical procedures over the years. Ionizing radiation treatment is used for both benign and malignant diseases. In systems where radiation is delivered through pathways, wire systems including a radioactive source are currently being tested for transporting the radioactive source to the treatment area. Manufacturers of wire systems in the U.S. include: Neocardia, U.S. Surgical Corporation, Best Industries, and Novoste. Manufacturers of wire systems in Europe include: Nucletron and Schnneider.

What is needed are better catheters.

What is needed are better catheter components.

What is needed are better systems for catheter manipulation and support.

What is needed are better and/or safer systems and methods for delivering ionizing radiation.

What is needed are better and/or safer wire systems and methods for ionizing radiation treatment.

BRIEF SUMMARY OF INVENTION

The present invention relates to a catheter assembly, comprising a flexible tubular catheter body having an inner lumen and a method of use. The catheter further comprises at least one fluid communication structure formed on the catheter body. The at least one fluid communication structure is adapted to permit fluid flow through a biological path. The catheter assembly may be used for medical procedures such as angioplasty or radiation treatment for cancer.

Versatility and multiple uses for the catheter is desired, including the ability to use the catheter in different ways during the same procedure.

The systems for catheter manipulation and structural support can be applied to all types of catheters. In the context of PTCA, the present invention can be applied most readily to guiding catheters.

Guiding catheters are large-lumen catheters that have three important functions: (1) they serve as conduits for the balloon/guide wire system into the coronary artery and provide relatively rigid support for forcing the deflated balloon across a stenosis; (2) they allow for the injection of contrast medium around the balloon catheter into the coronary arteries for visualization; and (3) they allow measurement of pressure at the ostium of the coronary artery by means of the fluid column around the balloon catheter. Like angiographic catheters, the guiding catheters are preshaped to optimize seating in the coronary ostium. In contrast to angiographic catheters, however, guiding catheters are more stiff. Choice of the right type of guiding catheter is critical to the success of the procedure: lack of support by the guiding catheter is a common cause of failure, where attempts to pass the balloon catheter result only in pushing the guiding catheter out of the coronary ostium, an equal and opposite reaction that results from the anatomical relationship of the coronary ostium to the path of the catheter through the aortic arch.

The current invention overcomes two continuing problems that are not addressed adequately in the prior art.

First, the current invention permits the manipulation of a catheter to facilitate its proper placement. In the context of PTCA, the present invention would permit manipulation of the guiding catheter to facilitate the placement of the distal end in the preferred coronary artery.

Second, the current invention provides structural support for the catheter so that it does not become misshapen or dislodged when fluid or objects are passed through the lumen of the catheter. In the context of PTCA, the present invention would provide structural support to the guiding catheter to prevent its dislocation from the selected coronary artery and it would provide structural support for the guiding catheter to facilitate the passage of the balloon catheter.

The present invention is a safer and more secure system for providing local radiation treatment especially with regards to commonly related medical problems. The present invention can be used intravascularly to irradiate areas developing blocks.

A radiation delivery system using a wire with both a radioactive portion and nonradioactive portion to deliver ionizing radiation treatment is described. It is possible, using the wire system of the present invention, to only radiate an intravascular area and avoid performing PTCA. Alternatively, the ionizing radiation treatment can be performed after PTCA.

An object of the invention is to improve catheters.

An object of the invention is to improve catheter components.

An object of the invention is to improve catheter manipulation and support.

An object of the invention is to improve upon systems and methods for delivering ionizing radiation.

An object of the invention is to improve upon wire systems and methods for ionizing radiation treatment.

BEST DESCRIPTION OF DRAWINGS

FIG. 4 shows a side view of an embodiment of the catheter of the present invention which uses balloons.

FIG. 6 shows a catheter with fluid communication structures and a balloon wrapped around the fluid communication structure.

FIGS. 6a–6h show cross sectional views of catheters with various configurations for fluid communication structures with a balloon wrapped around the fluid communication structure.

Figure 6I:
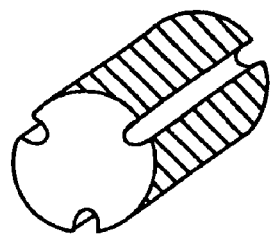
FIGS. 6i–6m show a balloon having longitudinal channels.
Figure 6J:
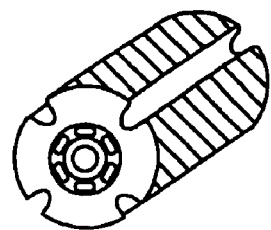
Figure 6K:
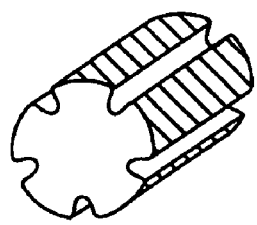
Figure 6L:
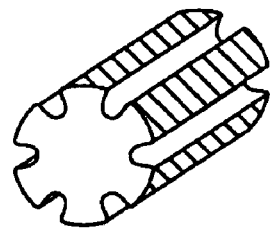
Figure 6M:
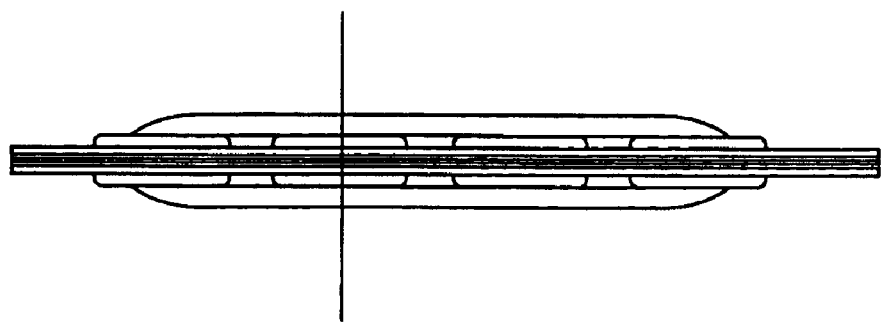
Figure 6N:
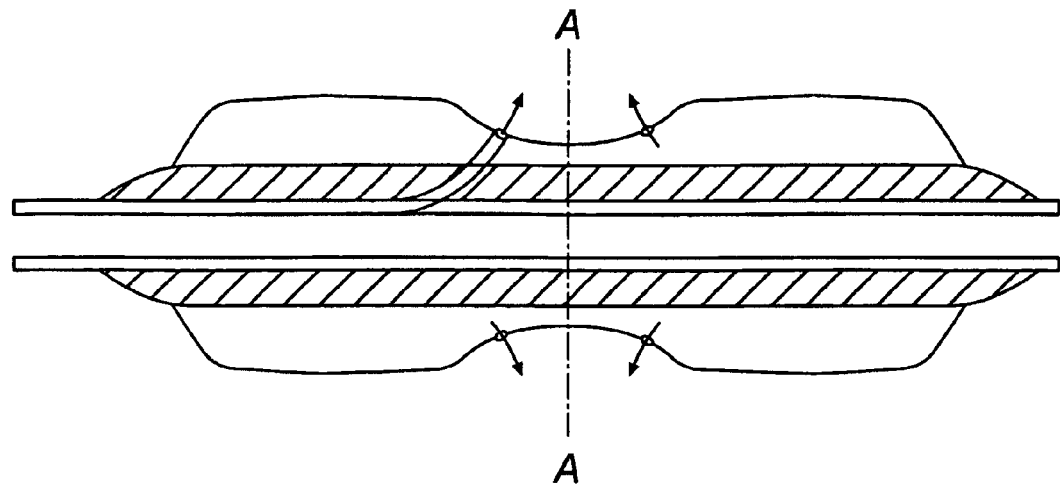
FIGS. 6n–6r show embodiments of a catheter using a local balloon infusion system.
Figure 6O:
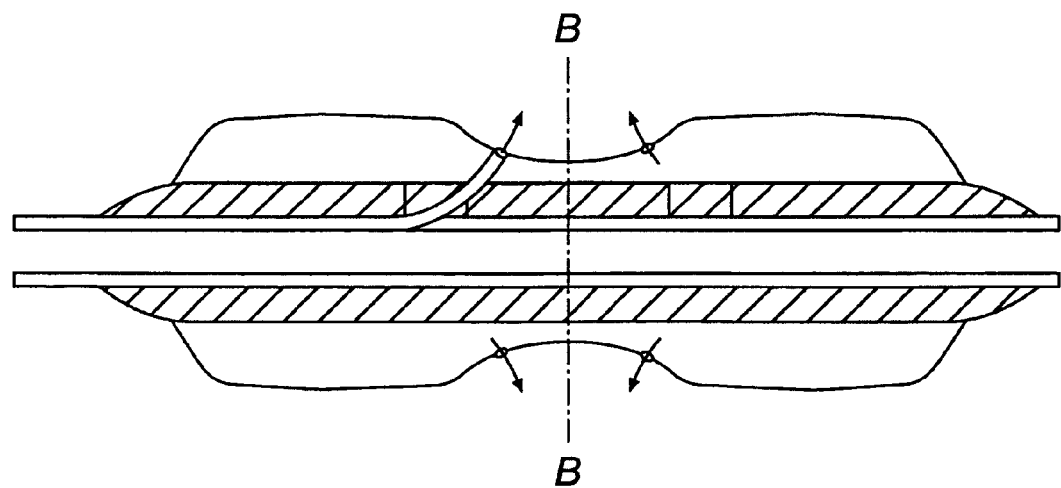
Figure 6P:
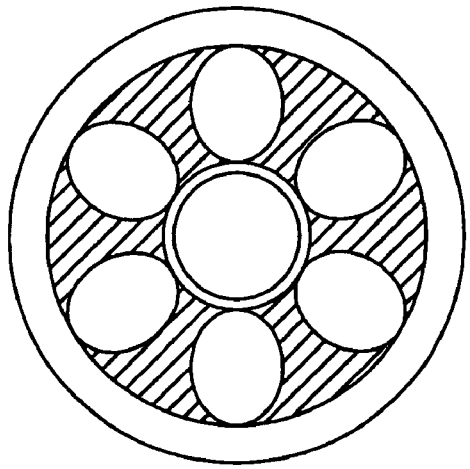
Figure 6Q:
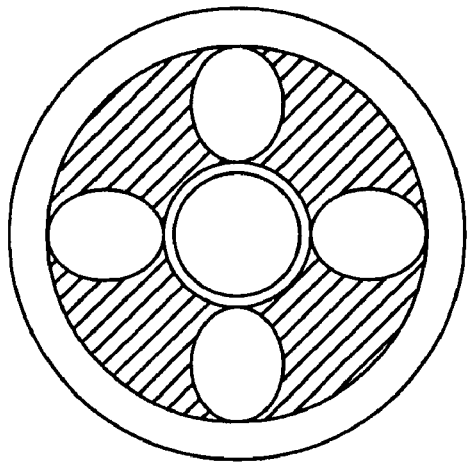
Figure 6R:
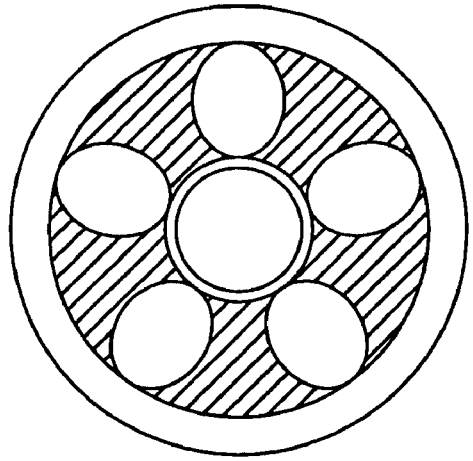

FIGS. 6p, 6q and 6r each show a cross sectional view with microconduits along the line A A or B B of FIGS. 6n and 6r.

Figure 7:
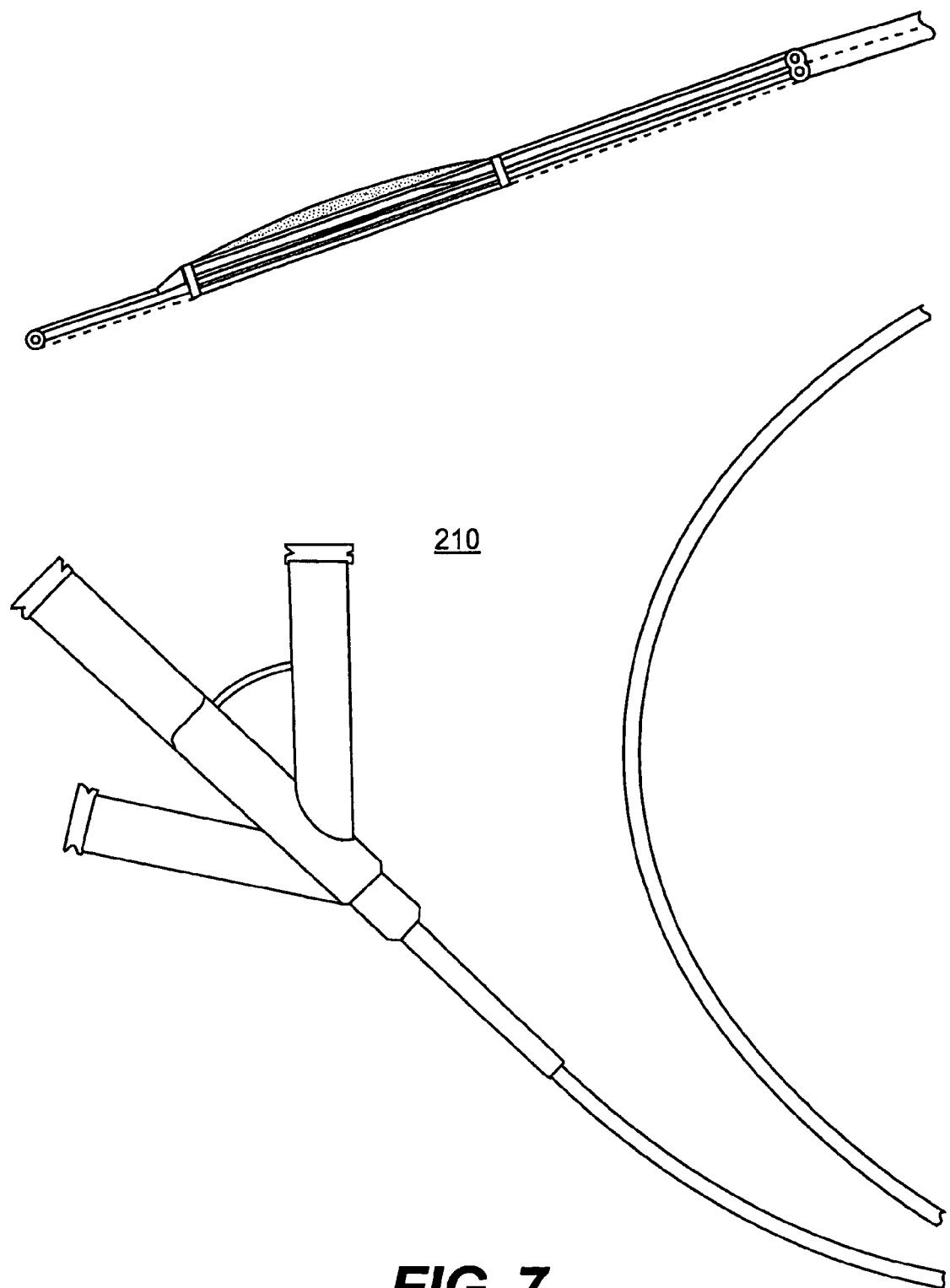

FIG. 7 shows an embodiment of the catheter of the present invention with a wired channel and balloons.

Figure 8:
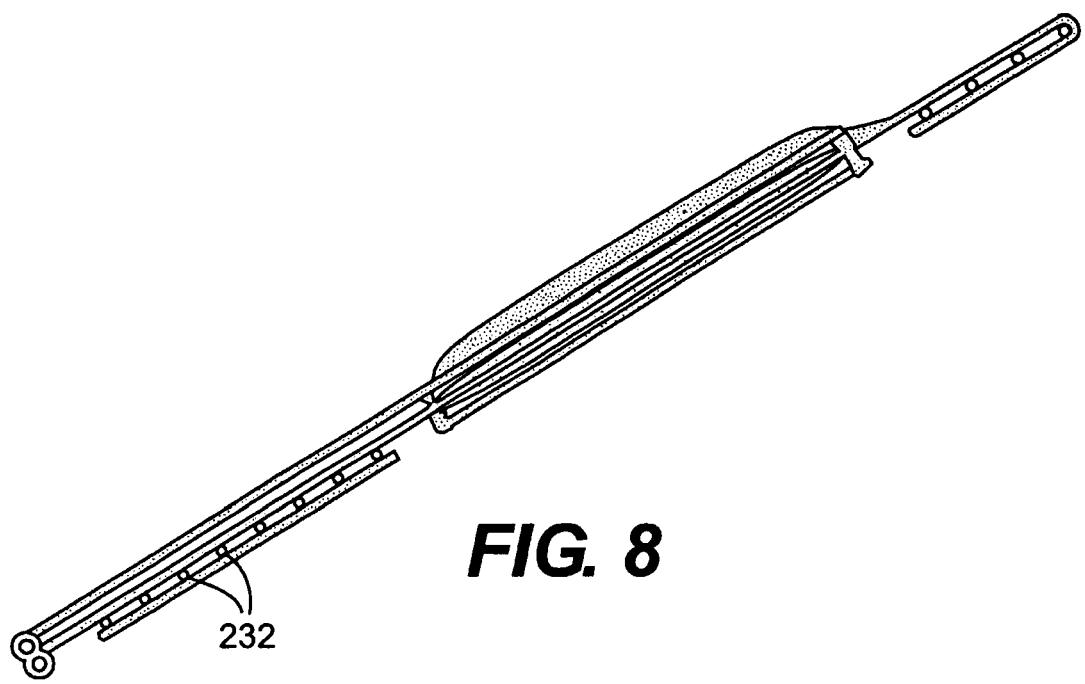

FIG. 8 shows a portion of the embodiment of the catheter shown in FIG. 7 and illustrating the perfusion holes in the catheter body.

FIGS. 9a–9f show various cross sections of a two channel catheter both with balloons and without balloons.

Figure 10A:
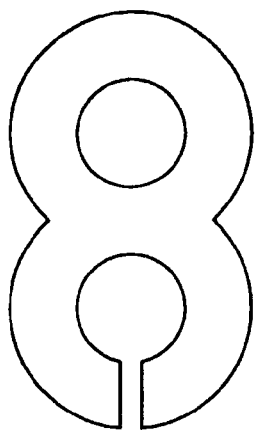
Figure 10B:
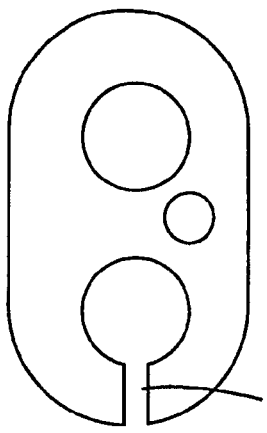
Figure 10C:
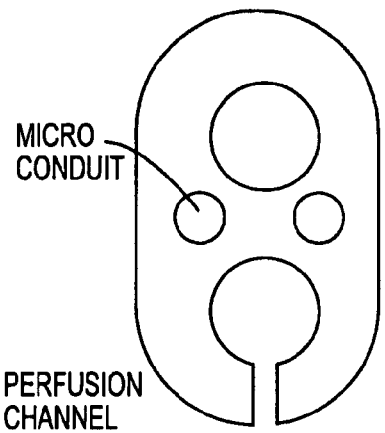
Figure 10D:
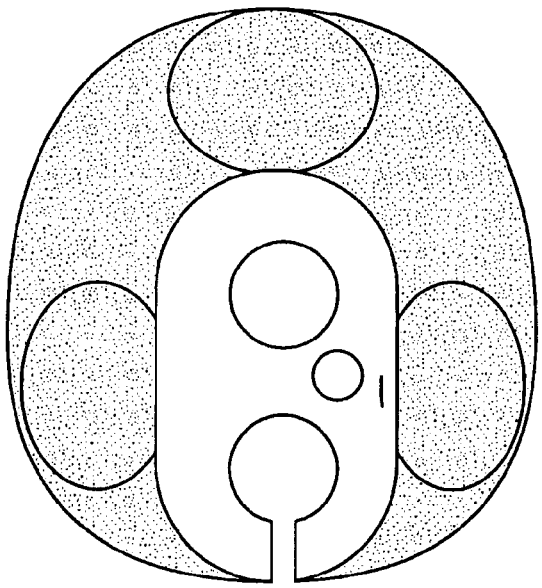
Figure 10E:
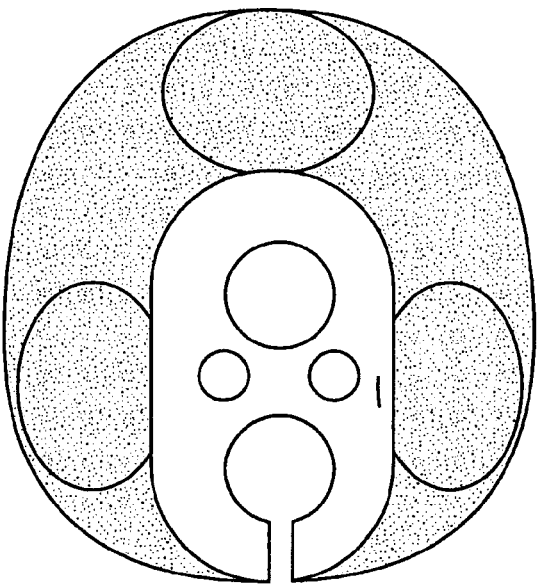
Figure 10:
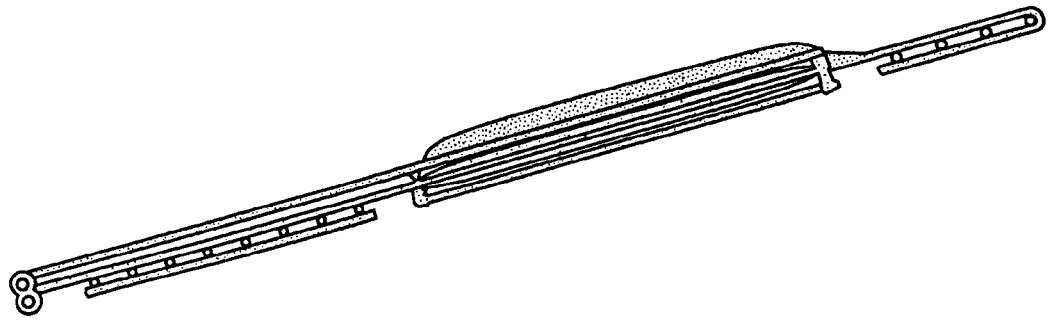

FIG. 10 shows an embodiment of the catheter in which a balloon is wrapped around the embodiment of the catheter shown in FIGS. 8, 9d and 9e.

FIGS. 10a–10e show variations of the catheter shown in FIG. 10.

FIGS. 11a–11e show various embodiments using valves.

FIGS. 12a–12d show a single channel catheter with a valve.

FIGS. 13a–13f show a single channel catheter with a microballoon valve.

FIGS. 14a–14f show a single channel catheter using a reversed valve.

Figure 15A:
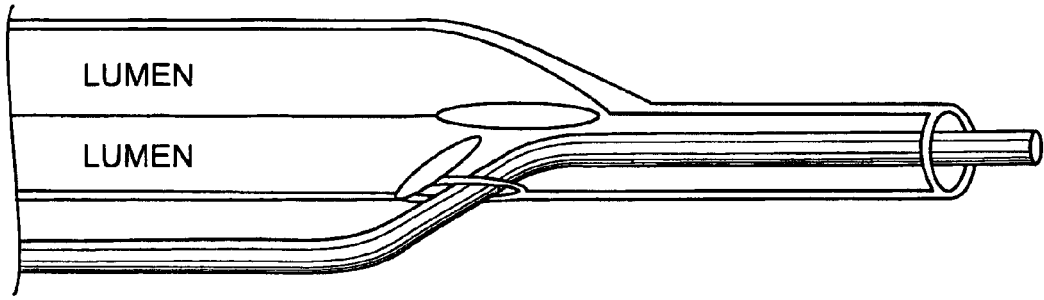
Figure 15B:
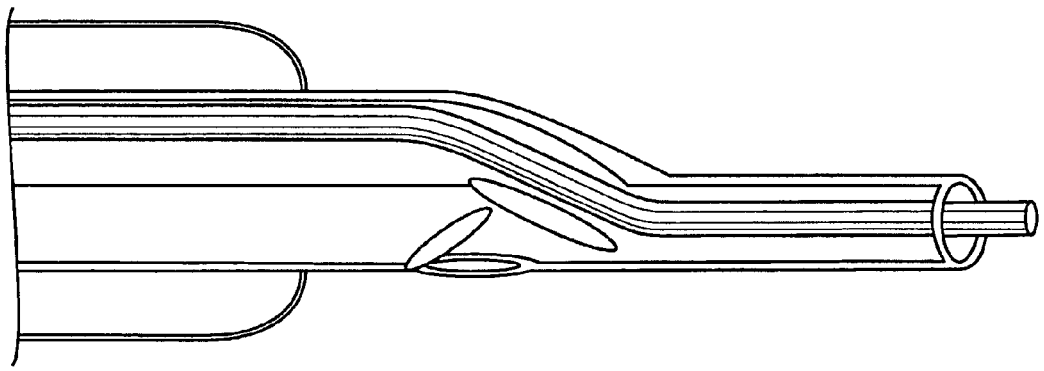
Figure 15C:
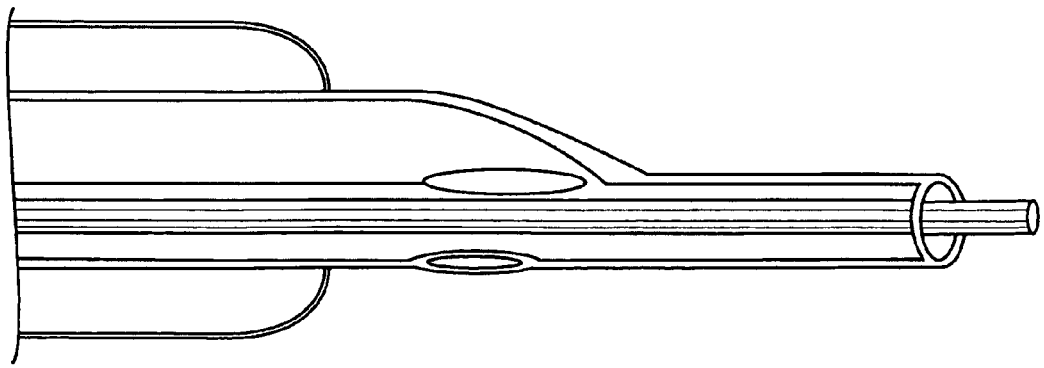
Figure 16A:
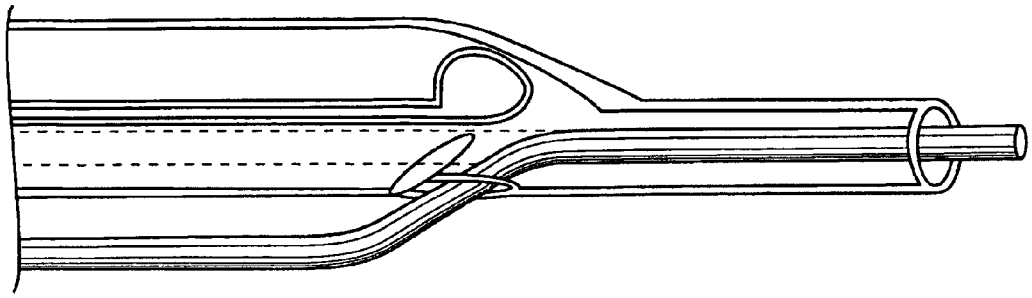
Figure 16B:
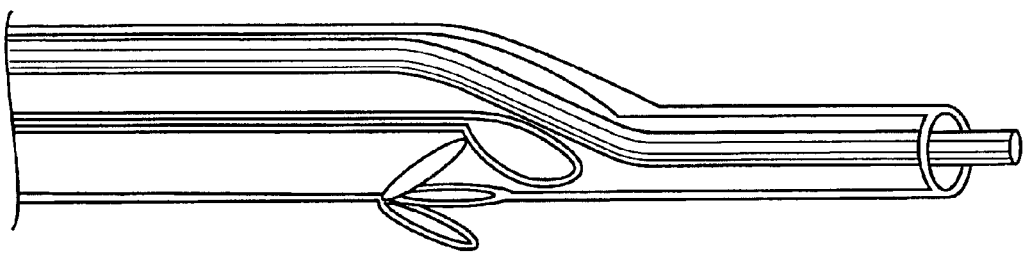
Figure 16C:
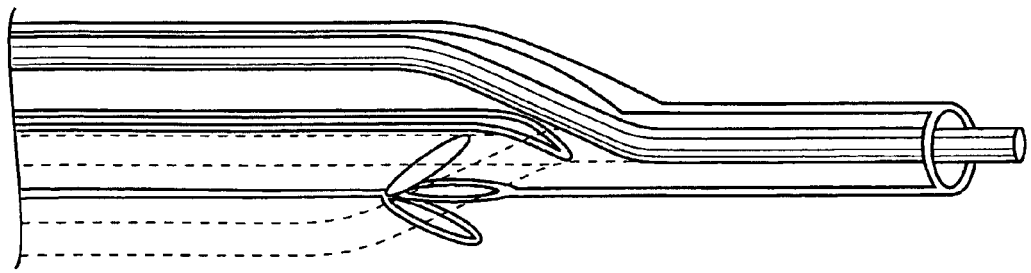

FIGS. 15a–15c show a two channel catheter with two valves FIGS. 16a–16c show a two channel catheter with a balloon valve.

Figure 17:
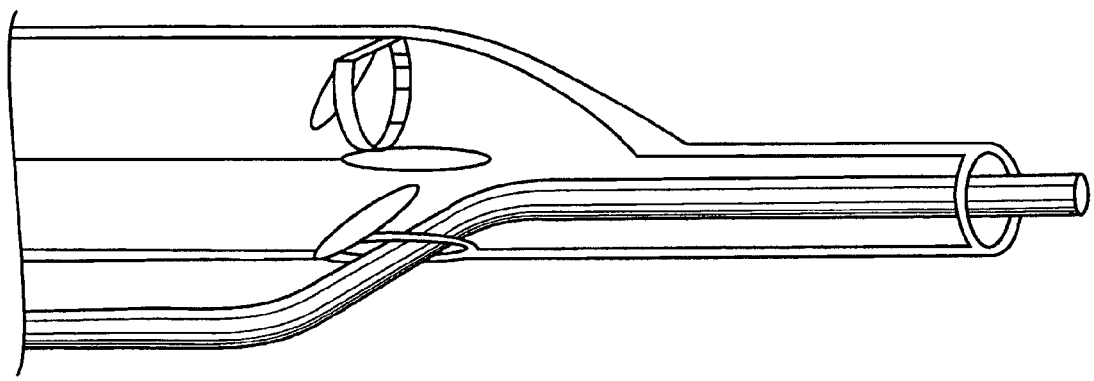

FIG. 17 shows a two channel catheter with an inverted valve.

Figure 18A:
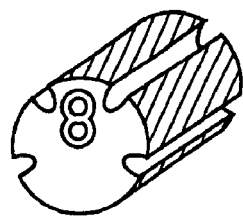
Figure 18B:
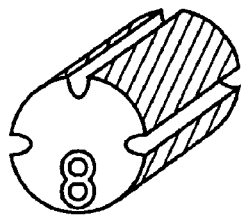
Figure 18C:
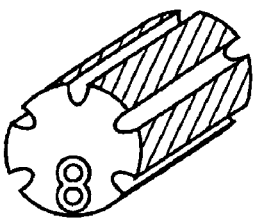

FIGS. 18a–18c show a cross sectional view of a two channel catheter with a balloon having longitudinal channels wrapped around the catheter.

Figure 18D:
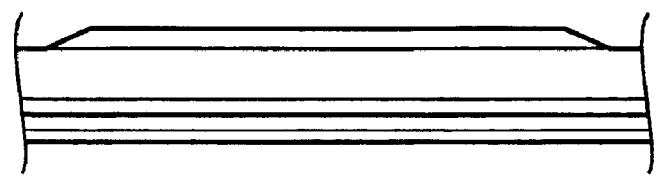

FIG. 18d shows a side view of a catheter with a balloon having longitudinal channels wrapped around a portion of the catheter.

FIGS. 19a, 19b, 19c and 19d show the use of balloons and/or catheter body to center the radiating lumen in a two lumen catheter system.

Figure 20:
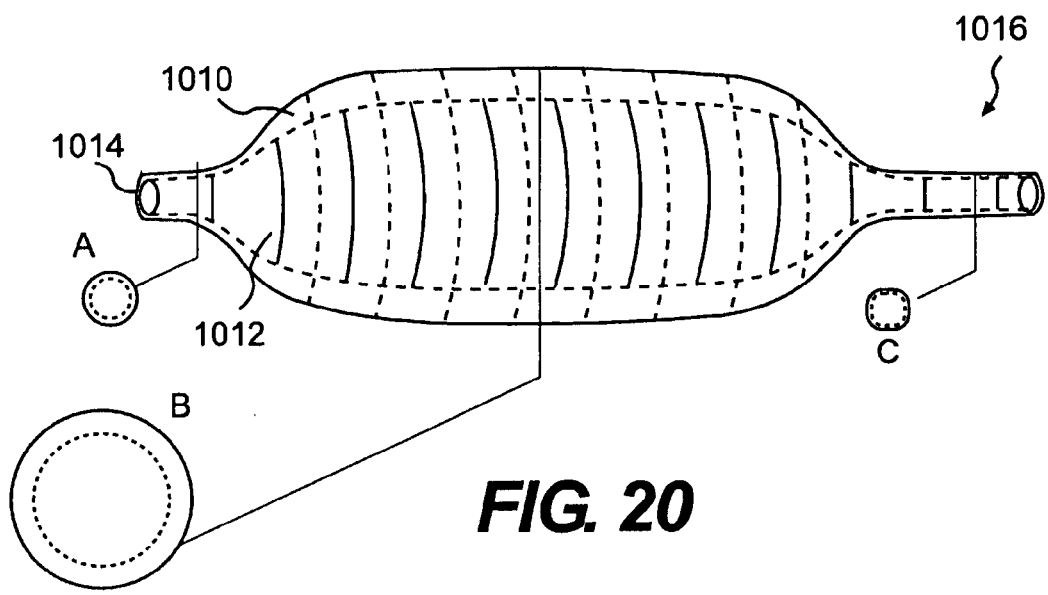

FIG. 20 shows a balloon structure for a catheter having an iner an outer balloon.

Figure 21:
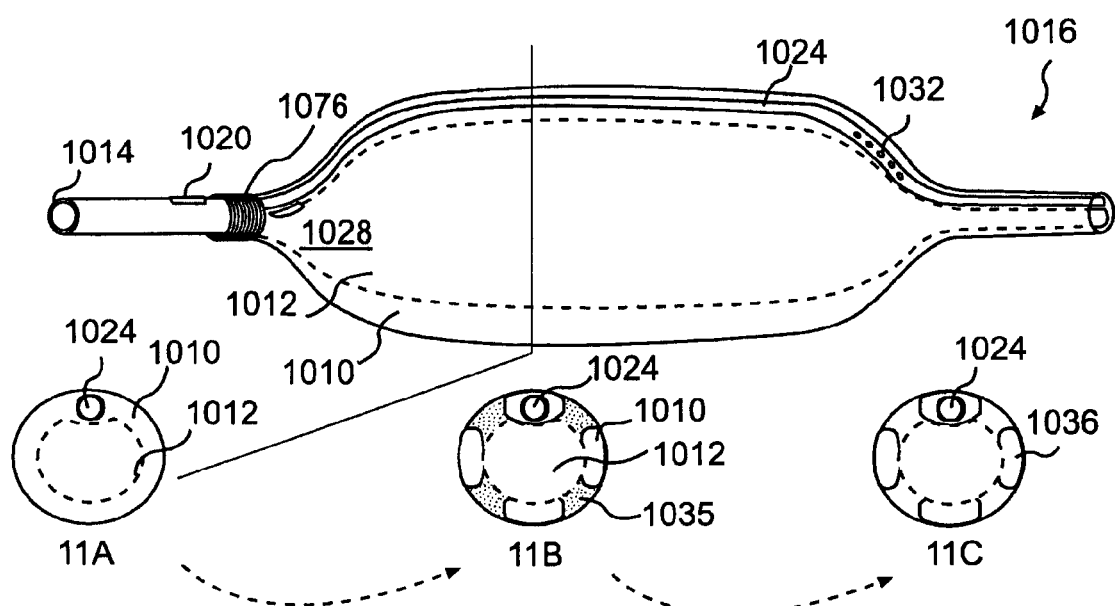

FIG. 21 shows a balloon structure similar to that shown in FIG. 20 with an inflator tube and alternative cross-sections a, b, and c.

Figure 22:
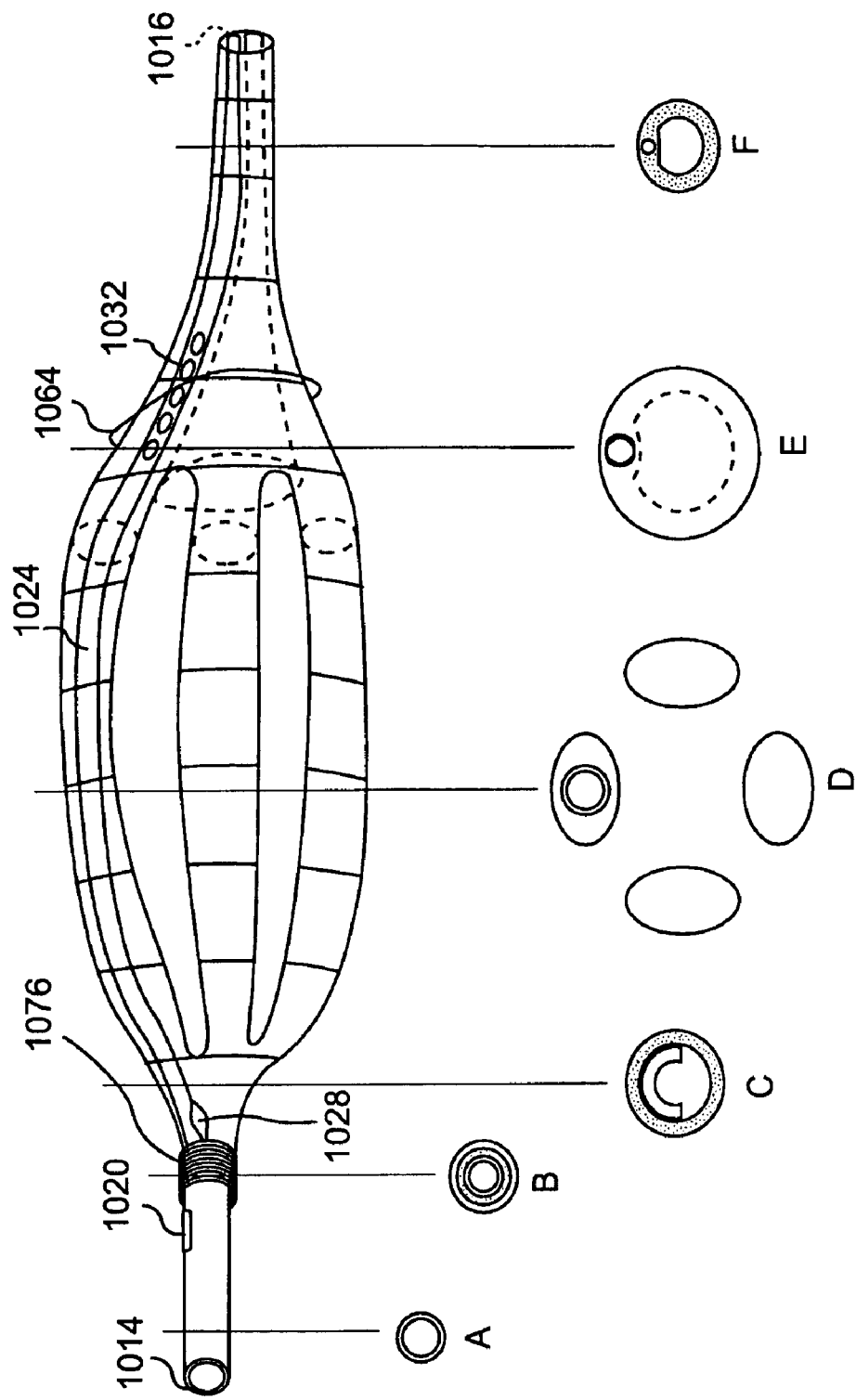

FIG. 22 shows a balloon structure for a catheter with multiple balloon segments or microtubes.

Figure 23:
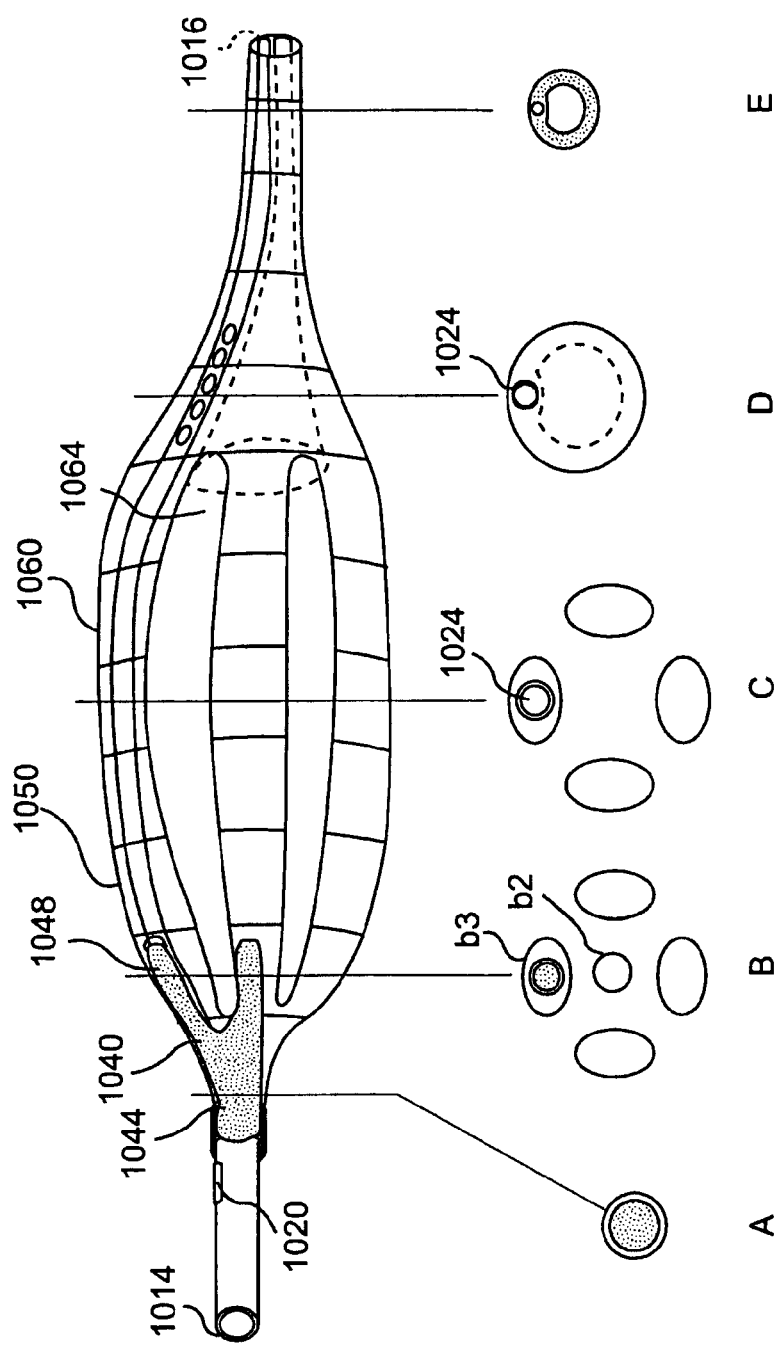

FIG. 23 shows a similar embodimetn to that shown in FIG. 23 but includes a form. Cross-sections a through e are shown.

Figure 24A:
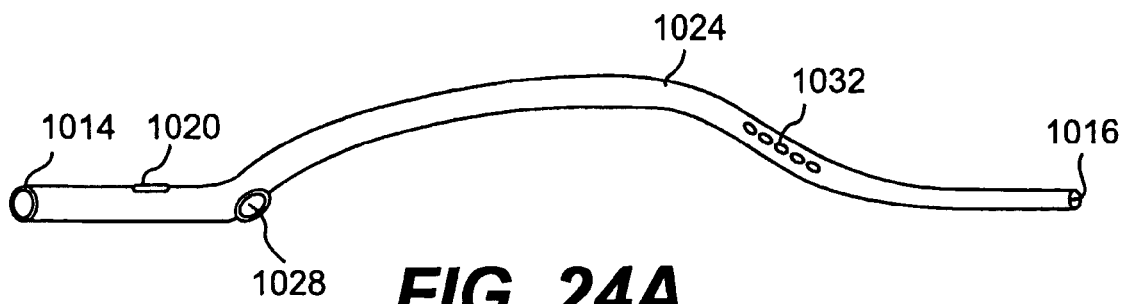
Figure 24B:
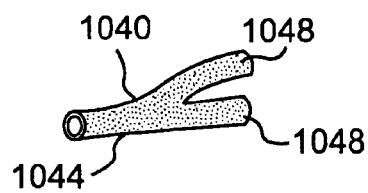
Figure 24C:
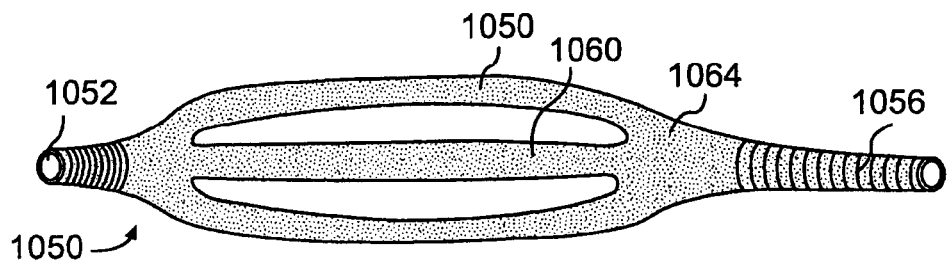

FIGS. 24a–24c show parts of a balloon structure.

Figure 24D:
Figure 24E:
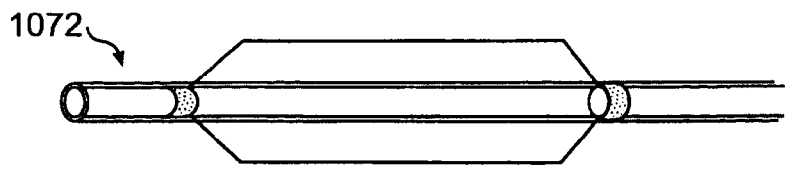

FIGS. 24d through 24e are catheters which can be used with balloon structures.

Figure 25:
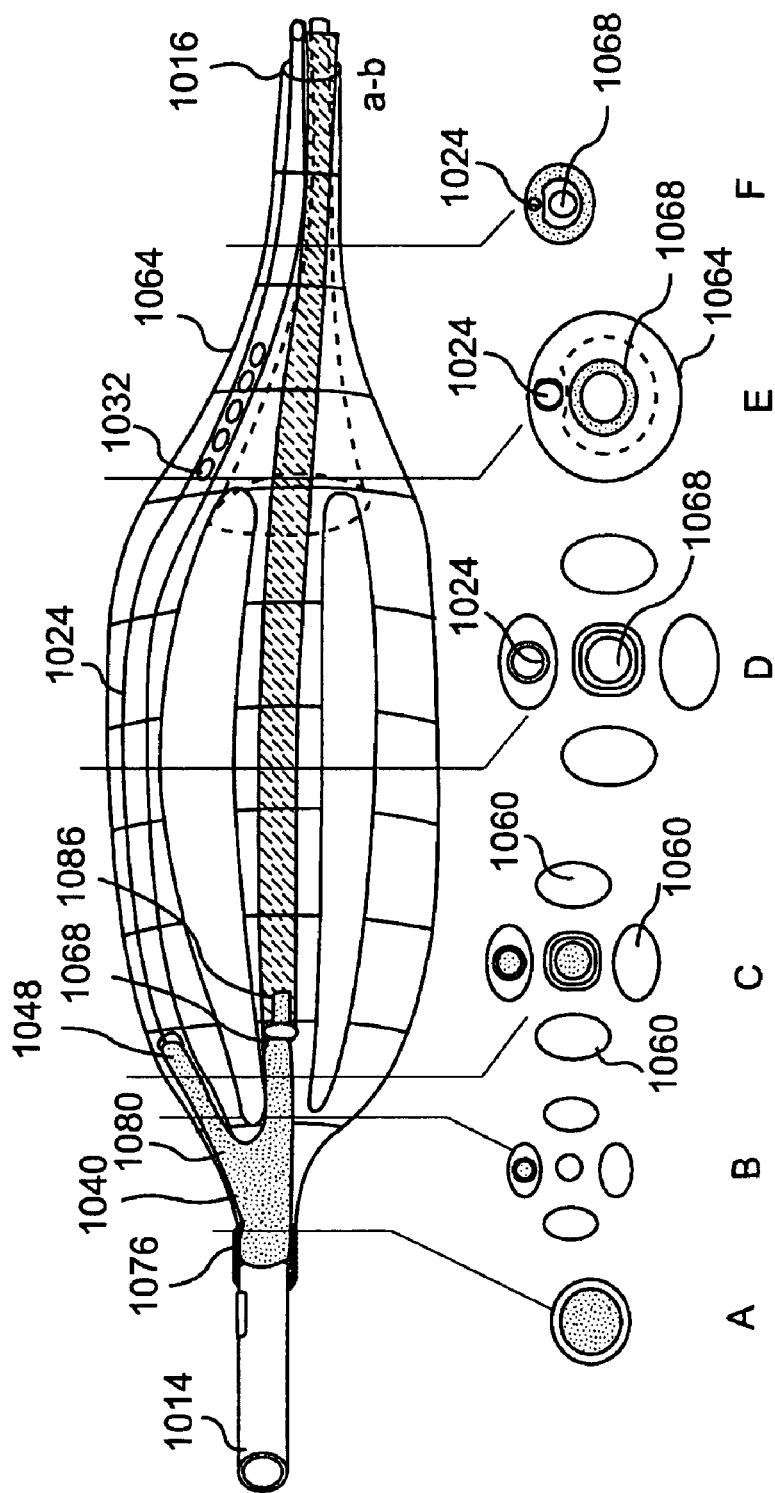

FIG. 25 shows an embodiment of a balloon structure with a simple catheter anchored.

Figure 26:
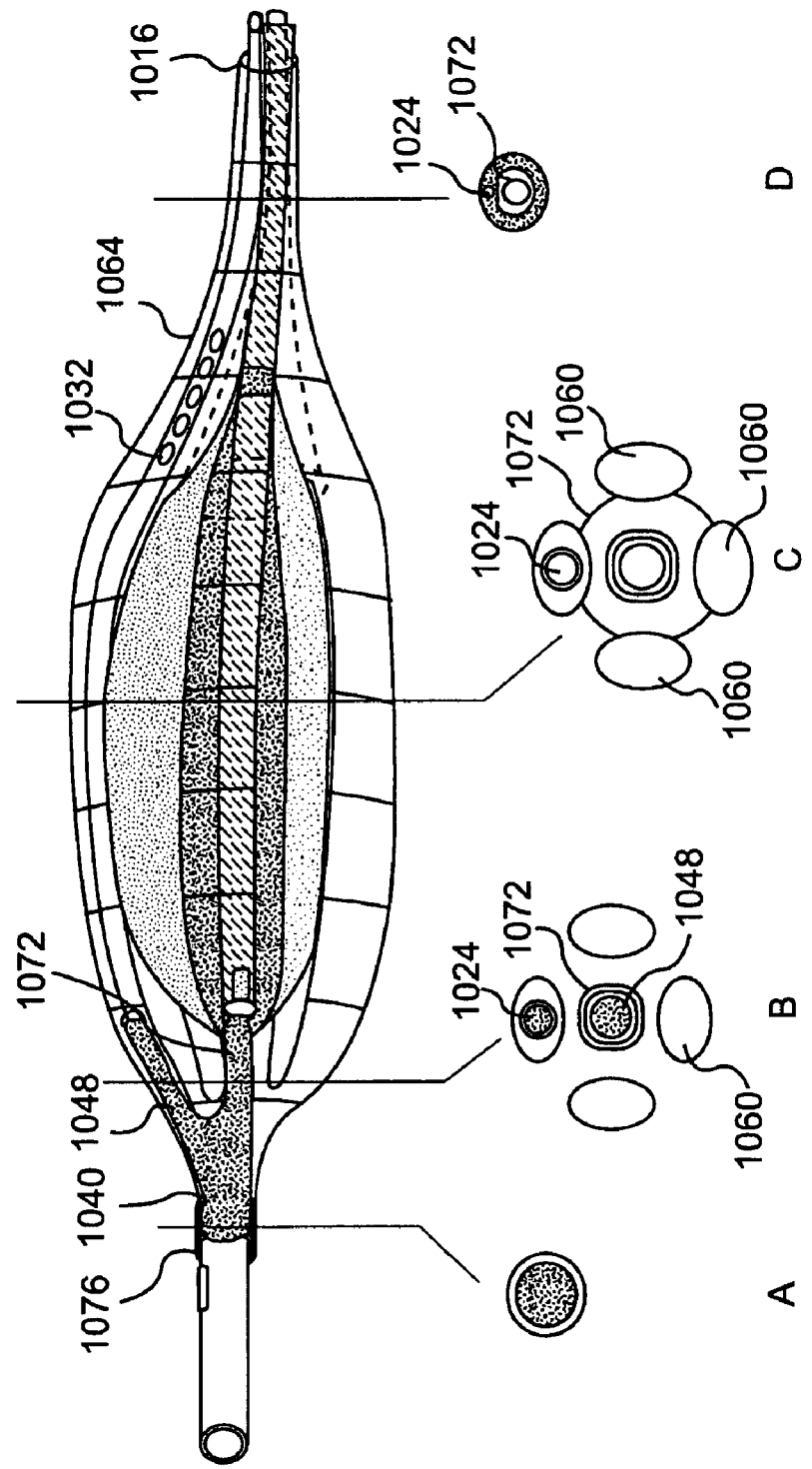

FIG. 26 shows an embodiment9 of a balloon structure with an anchored inflatable catheter.

Figure 27:
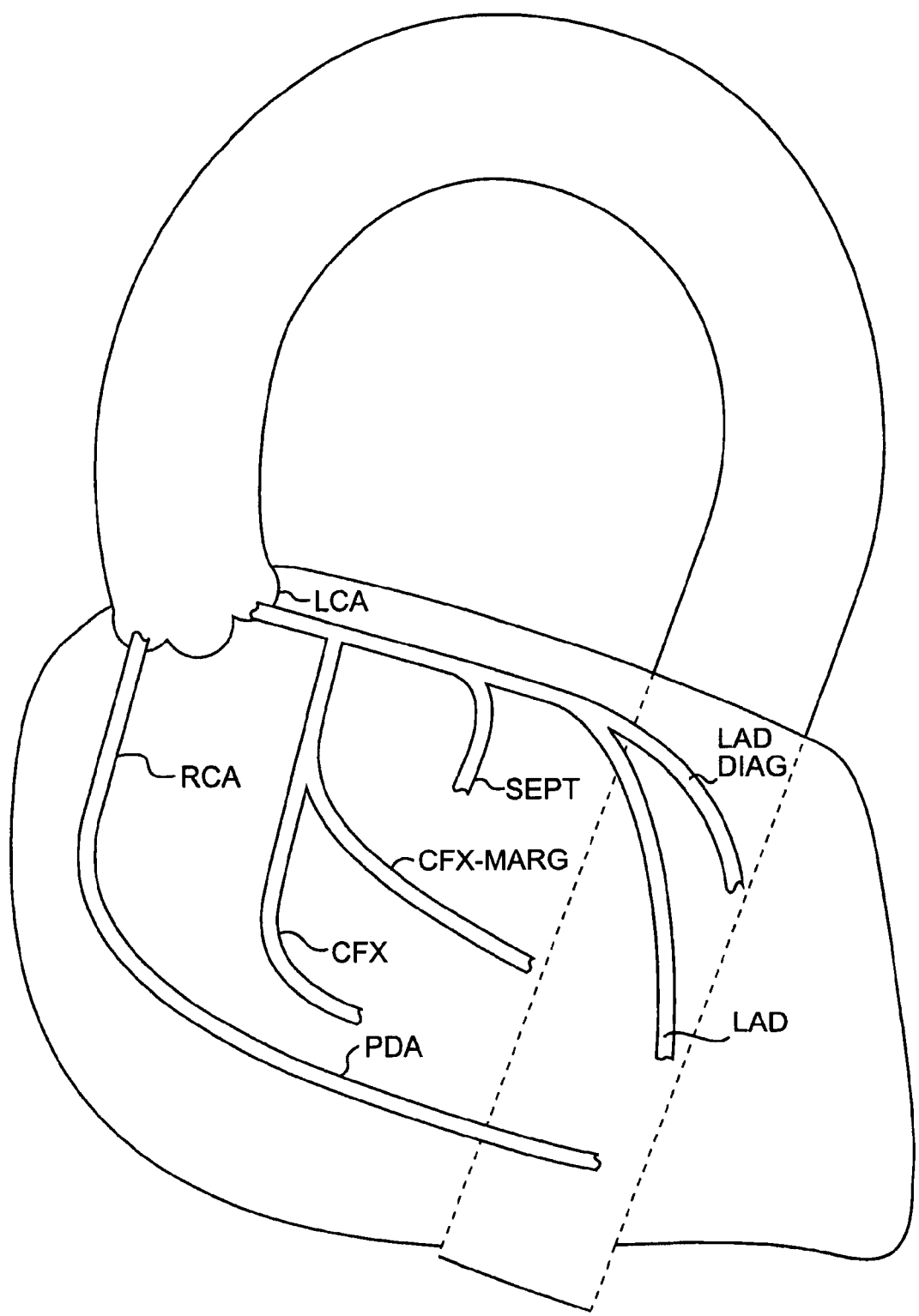

FIG. 27 shows the arteries around the heart.

FIGS. 28A–28D shows a wire system for a left coronary artery entrance.

FIGS. 28E–28I shows a wire system for a right coronary artery entrance.

Figure 29A:
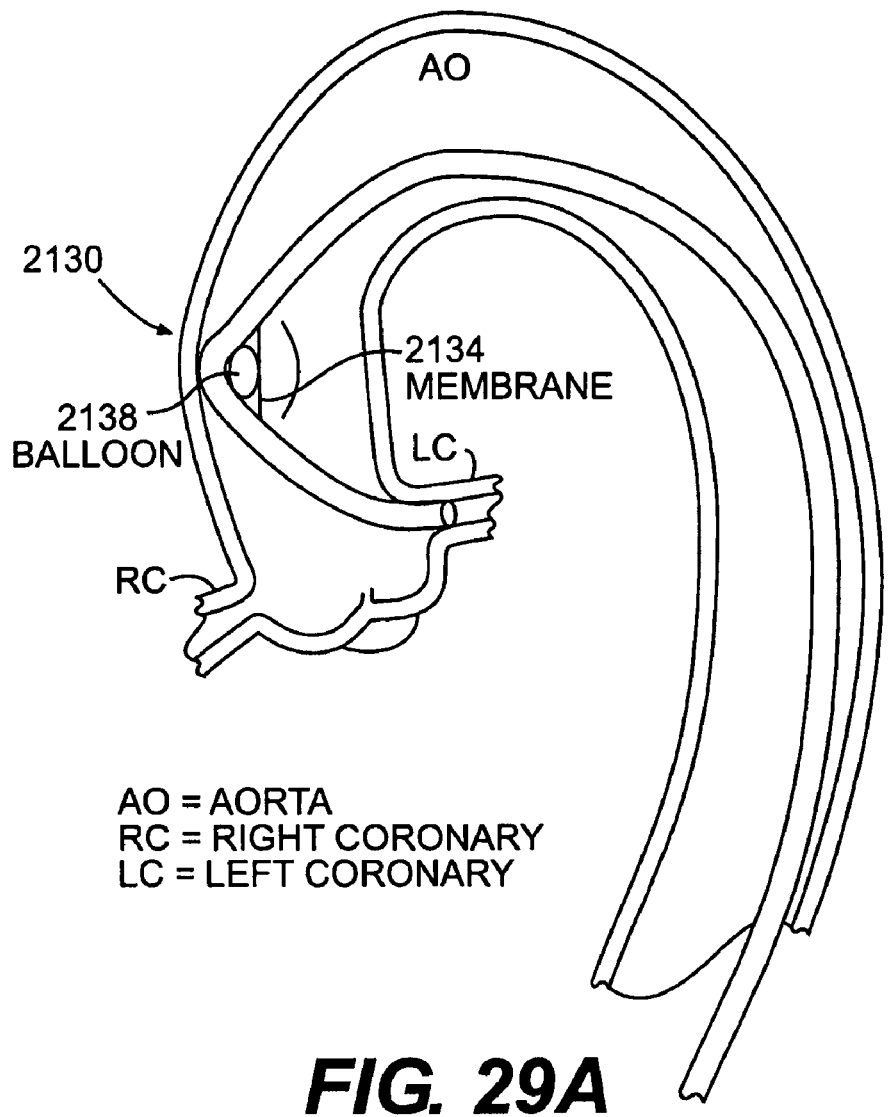
Figures 29B, 29C:
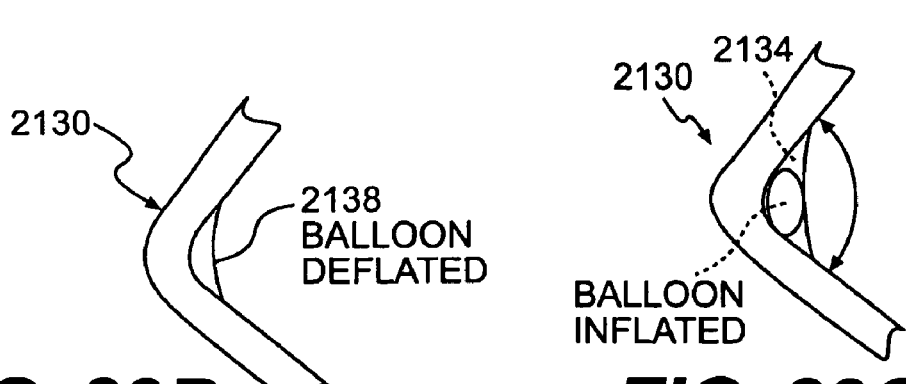

FIGS. 29A–29C shows a balloon system for a left coronary artery entrance.

Figure 29D:
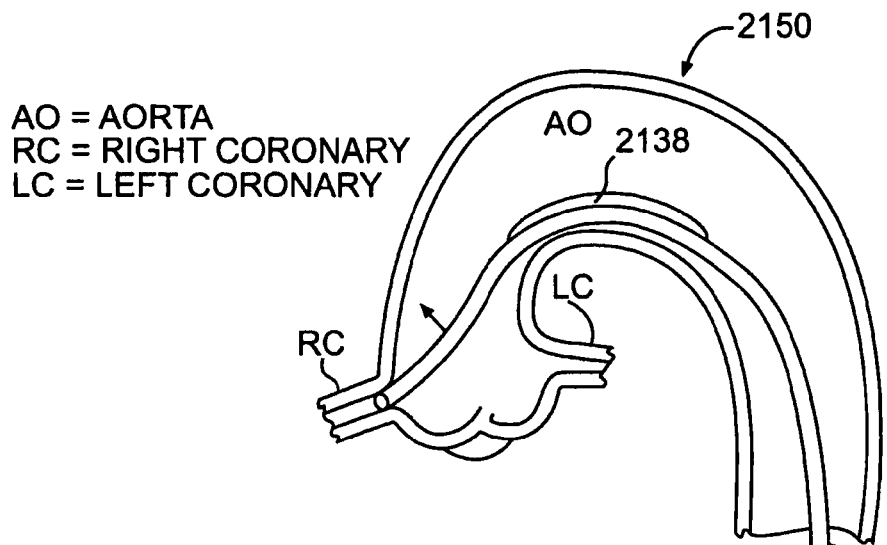
Figure 29E:
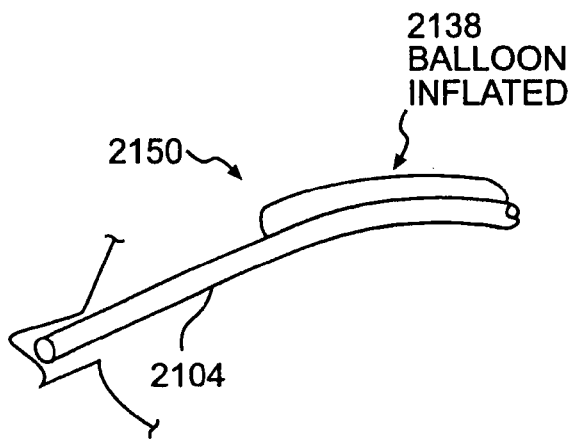
Figure 29F:
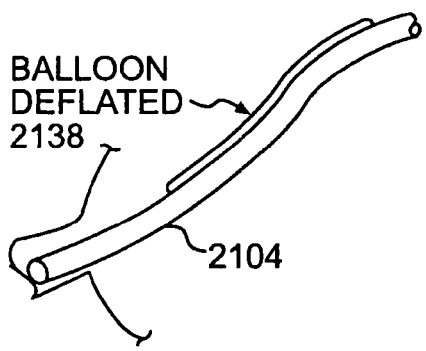

FIGS. 29D-29F shows a balloon system for a right coronary artery entrance.

FIGS. 30a–30c shows a cord system for a left coronary artery entrance.

FIGS. 30d–30g shows a cord system for a right coronary artery entrance.

FIG. 31a is a schematic of a wire system.
FIG. 31b is a schematic of a wire system.
FIG. 31c is a schematic of a wire system.
FIG. 31d is a schematic of a wire system.

FIGS. 32a, 32b, 32c, and 32d are schematics of radiation sources or parts.

Figure 33A:
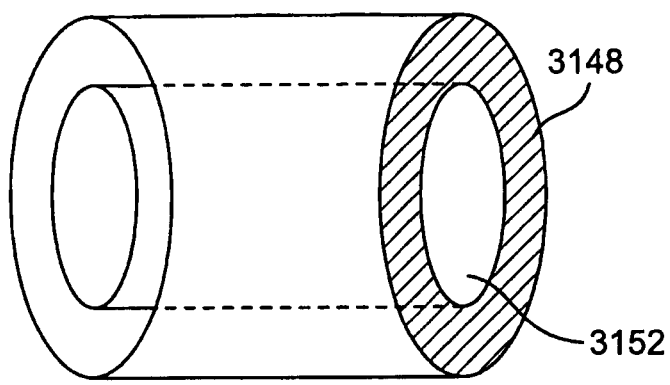
Figure 33B:
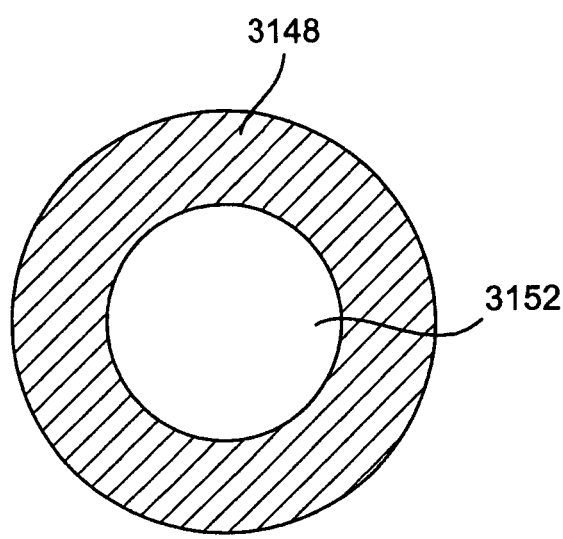

FIGS. 33a and 33b are schematics of a doughnut or washer radiation part. FIG. 33b is a cross-sectional view.

Figure 34A:
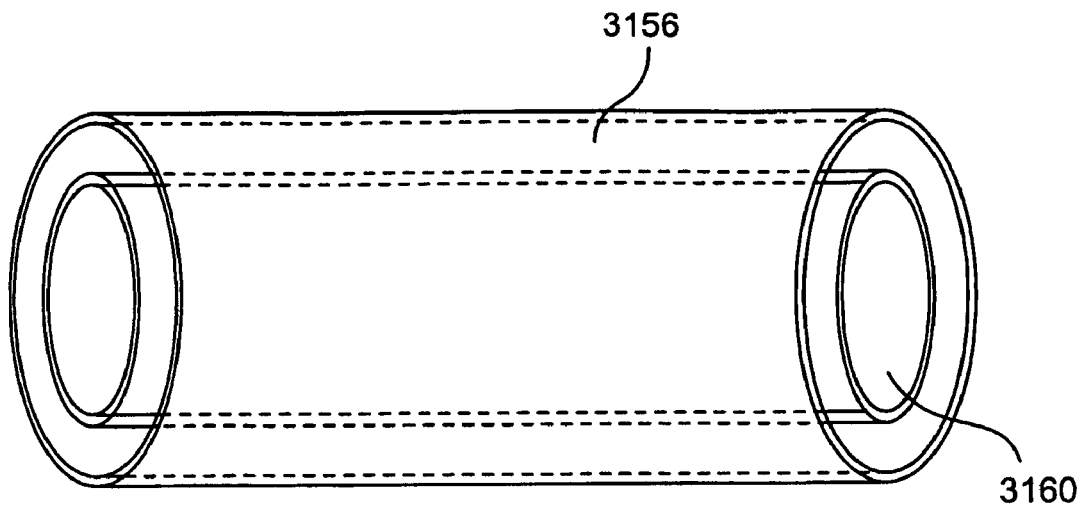
Figure 34B:
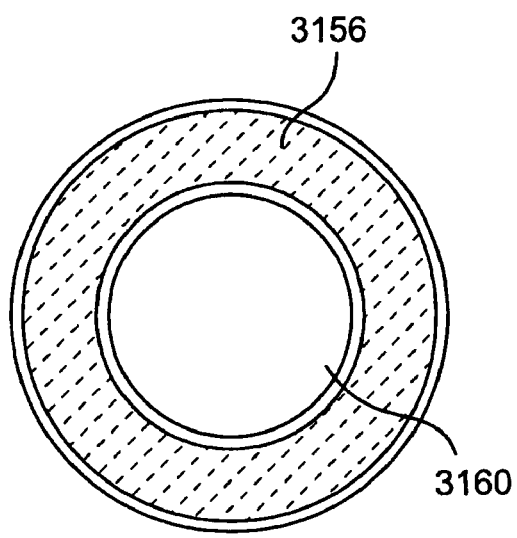

FIGS. 34a and 34b are schematics of a cylinder radiation part. FIG. 34b is a cross-sectional view.

FIG. 35a is a schematic of a wire system with cover using doughnut or washer radiation parts.

FIG. 35b is a schematic of an alternative design for a wire system with cover using a coil radiation part.

FIGS. 36a, 36b, and 36c are schematics of a wire system with cover, each using a coil radiation part.

FIG. 37 is a schematic of a wire system with cover using a doughnut or washer radiation parts.

Figure 38:
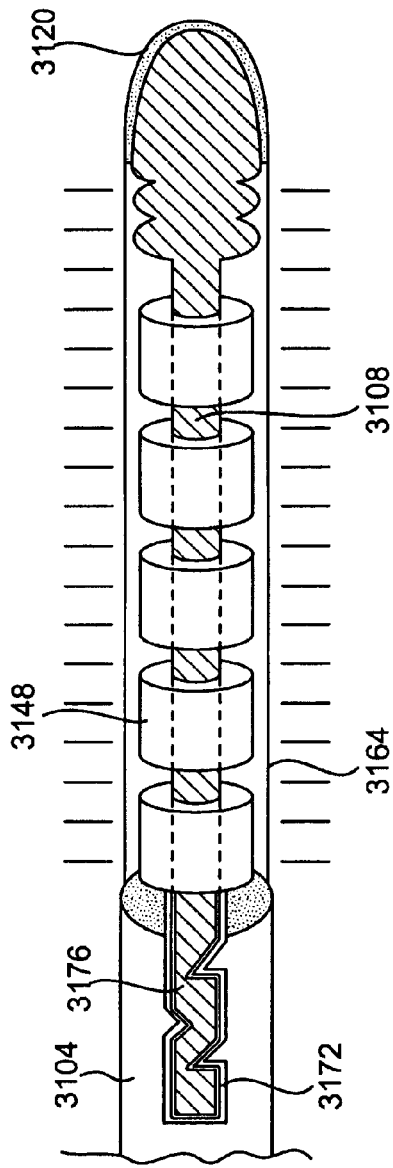

FIG. 38 is a schematic of a wire system using a push in drive cable connection.

Figure 39:
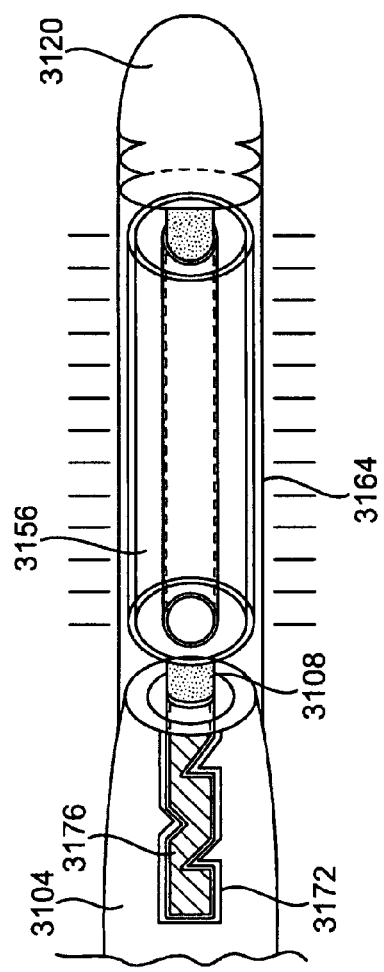

FIG. 39 is a schematic of a wire system using a push in drive cable connection.

FIGS. 40a, 40b, and 40c are schematics of the use of a stopper.

FIGS. 41a, 41b, 41c, 41d, 41e, and 41f are schematics of the use of a split end pin.

FIGS. 42A-42E are schematics of the use of an end pin.

Figure 43A:
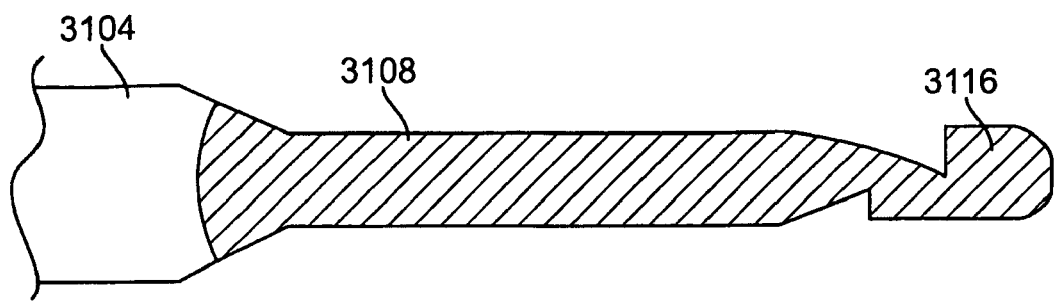
Figure 43B:
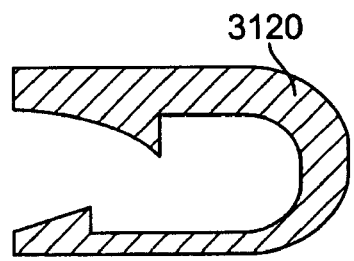
Figure 43C:
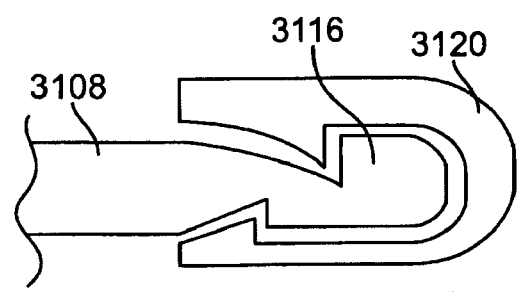

FIGS. 43a, 43b, and 43c are schematics of the use of a stopper.

FIGS. 44a, 44b, 44c, 44d, 44e, and 44f are schematics of an alternative embodiment which does not use a stud.

Figure 45:
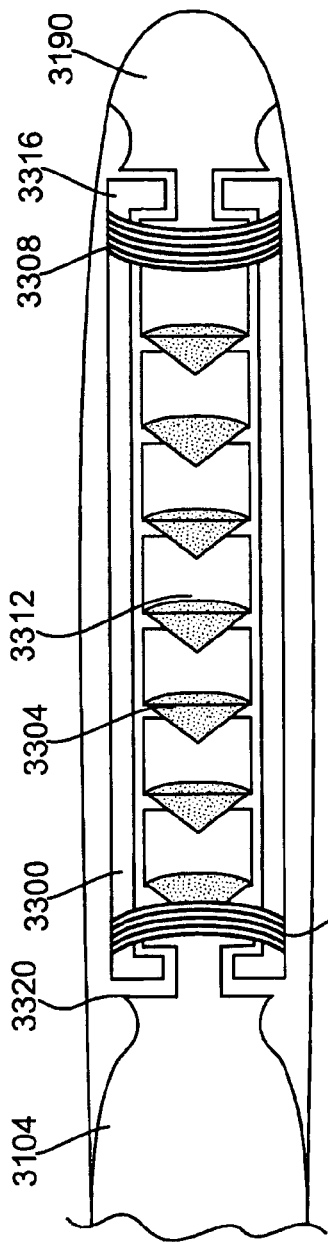

FIG. 45 is a schematic of an alternative embodiment which does not use a stud.

Figure 46A:
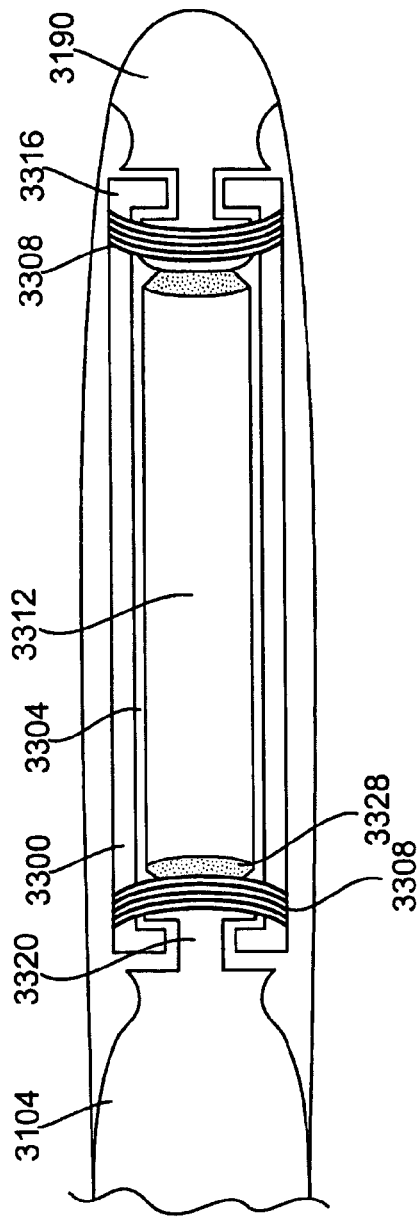

FIG. 46a is a schematic of an alternative embodiment which does not use a stud.

FIG. 46b is an expanded view of a cylindrical radioactive part.

FIGS. 46c, 46d, 46e and 46f are parts for an alternative embodiment which does not use a stud.

Figure 46E:
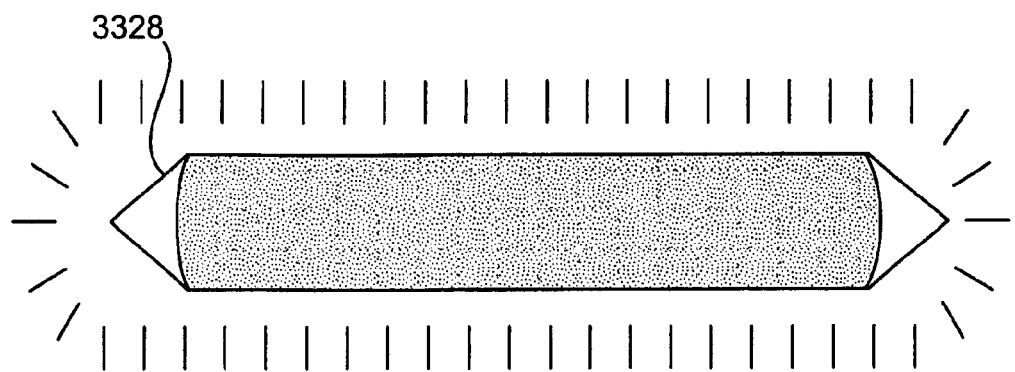
Figure 46F:
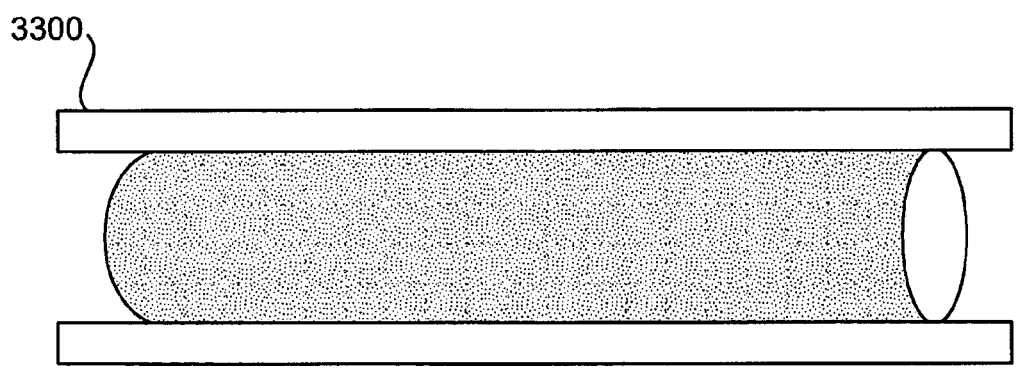
Figure 46G:
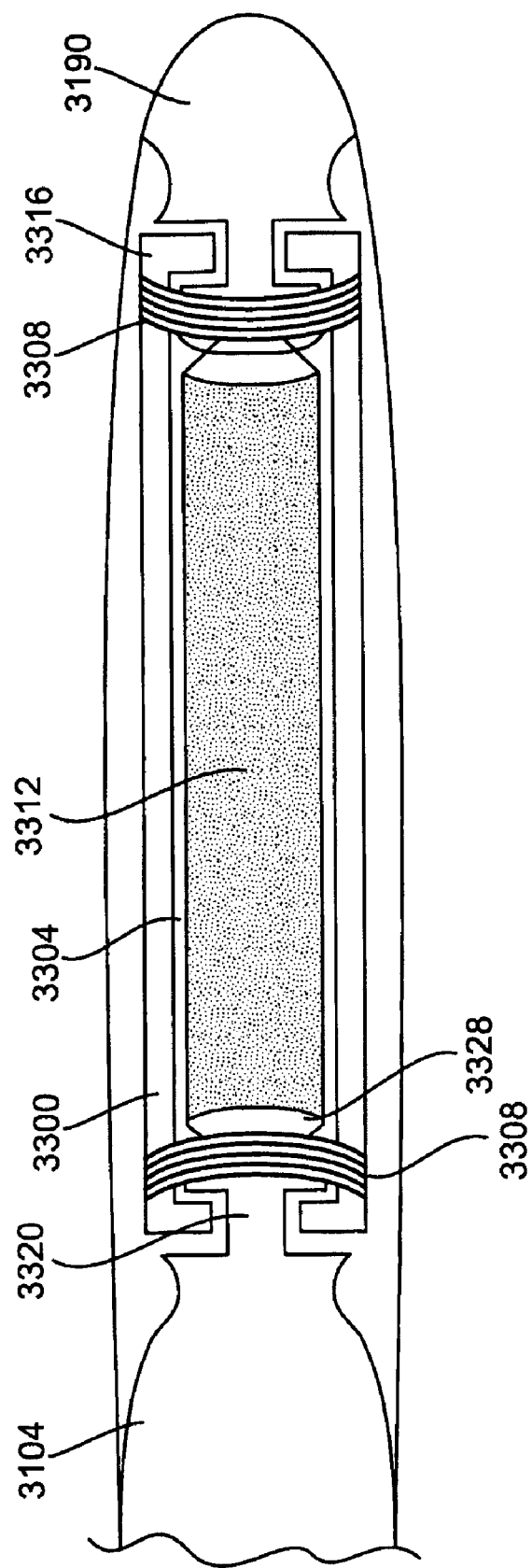

FIG. 46g is a schematic of an alternative embodiment using the parts shown in FIGS. 46c through 46f.

DISCLOSURE OF INVENTION, BEST MODE FOR CARRYING OUT INVENTION, INDUSTRIAL APPLICABILITY, AND DETAILED DESCRIPTION

I. Multi-Purpose Catheters

With reference to FIGS. 1–18, various embodiments of the multi-purpose catheter of the present invention will be described. As will be described in more detail below, the multi-purpose catheter may be used for perfusion of fluids and/or gases during treatment; irradiation of tissue in a biological path; infusion of drugs; and dilation of a biological path.

A. A Catheter with One Inner Lumen and Bulks

Figure 1:
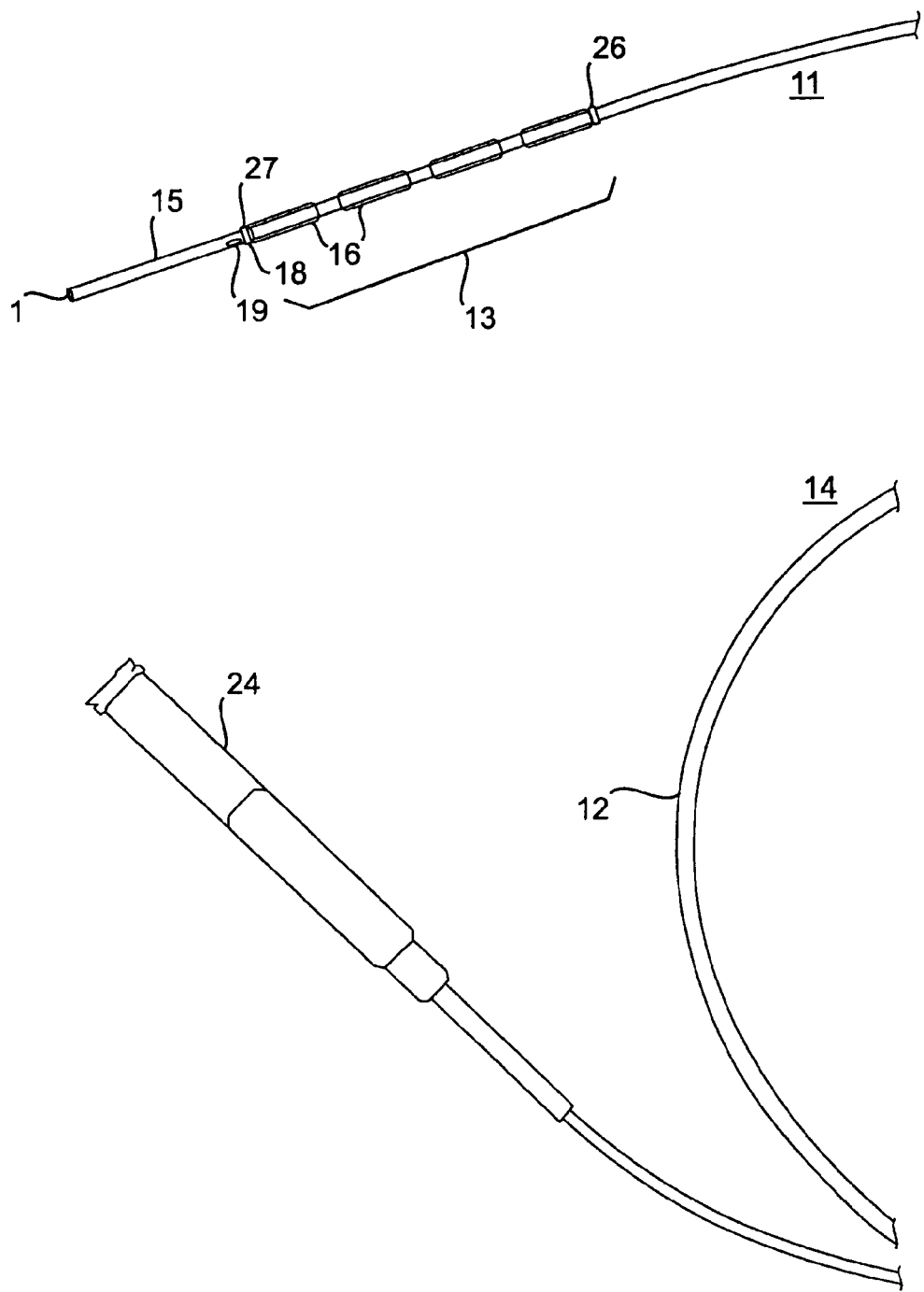
FIG. 1 shows a side view of a novel catheter with fluid communication structure.

With reference to FIGS. 1, 2 and 3A through 3I, a first embodiment of the catheter of the present invention will be described. As shown in FIG. 1, the catheter 10 comprises a flexible tubular catheter body 12 having an inner lumen 14 and at least one fluid communication structure 16 formed on the catheter body 12 adapted to permit fluid flow through a biological path. This catheter may be used for dilation and/or radiation treatment. A distal end 18 of the inner lumen 14 is closed, thereby forming a closed end channel. An irradiation source (not shown), attached to the end of a guide wire, may be placed in the inner lumen 14 and moved through the inner lumen 14 to the end or near the end of the closed channel. A closed conduit port 24 at the proximal end of the catheter body 12 facilitates the introduction of the irradiation source. In addition, radial opaque markers 26, 27 are located at the extremities of the fluid communication structures 16. The most distal marker 27 marks the end of the closed channel formed in the inner lumen 14. These markers 26, 27 along with television monitoring equipment allow a doctor to visually place the irradiation source at the precise location where radiation treatment is required within the biological path. The biological path includes, but is not limited to, urinary tracts, blood vessels, gastrointestinal and biliary ducts, respiratory tracts, arteries, and veins.

Figure 2:
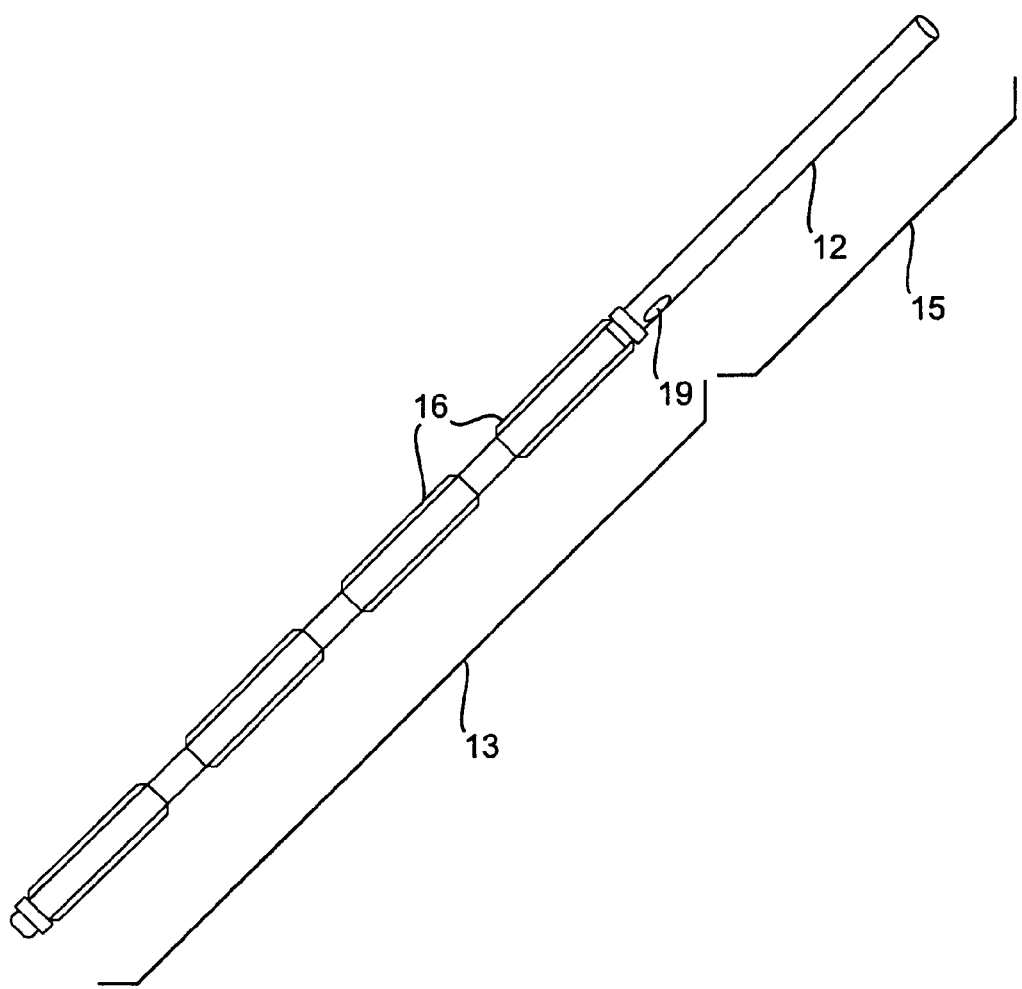
FIG. 2 is an enlarged view of the lower portion of the catheter shown in FIG. 1.

In addition, as shown in FIGS. 1 and 2, the catheter 10 has a guide wire entry port 19 located distally from the fluid communication structures 16. The guide wire exit port 21 allows the guide wire to exit the catheter 10. This guide wire entry port allows for a monorail system in which the guide wire is introduced at this port. A monorail system is one in which the guide wire is partially outside the catheter body.

In the preferred embodiment, (1) the catheter 10 is approximately 120 to 140 centimeters in length 50; (2) the proximal segment length 52, which refers to the portion of the catheter from the closed conduit port 24 to the bulks 16 (referred to as the "proximal segment" 11) is approximately 115 to 135 centimeters; (3) middle segment length 54, which refers to the portion of the catheter which contains the bulks 16 (referred to as the "middle segment" 13), is approximately 3 to 4 centimeters; and (4) the distal segment length 56, which refers to the portion of the catheter 10 that extends beyond the bulks 16 (referred to as the "distal segment" 15), is approximately 1.5 to 2 centimeters and may be as long as 2 to 5 centimeters. The distal segment is soft and has a low profile. In the preferred embodiment, the outer diameter 60, 62, 64 of the catheter 10 in each of these segments (i.e., the proximal segment 11, the middle segment 13, and the distal segment 15) respectively is as follows: (1) the outer diameter 60 of the catheter 10 in the proximal segment 11 is approximately 0.039 to 0.045 inches; (2) the outer diameter 62 of the catheter 10 in the middle segment 13 is approximately 0.065 to 0.069 inches; and (3) the outer diameter 64 of the catheter 10 in the distal segment 15 is approximately 0.039 to 0.045 inches. In the preferred embodiment, in all three segments 11, 13, and 15, the inner lumen 14 has a diameter generally in the range of 0.019 to 0.021 inches. Also, the guide wire exit port 21 has a diameter of approximately 0.25 inches.

With reference to FIGS. 2 and 3A–3I, the fluid communication structure 16 will be described. At least one fluid communication structure 16 is formed on the body 12 of the catheter 10. As shown in FIG. 2, four fluid communication structures are formed. Any number of fluid communication structures 10 may be formed on the body 12 of the catheter 10. The fluid communication structure 16 shown in FIGS. 2 and 3A–3F also referred to as "bulks" may be formed using teflon, polyurethane, polyethylene, or similar materials. In the preferred embodiment, each of the bulk segments 16 have a length between 3 to 7 millimeters. The 3 to 4 bulk segments shown generally span 30 to 40 millimeters of the catheter body 12. Each bulk 16 can be fenestrated or solid perforated polyethylene, teflon, polyurethane, or other similar materials.

Figure 3:
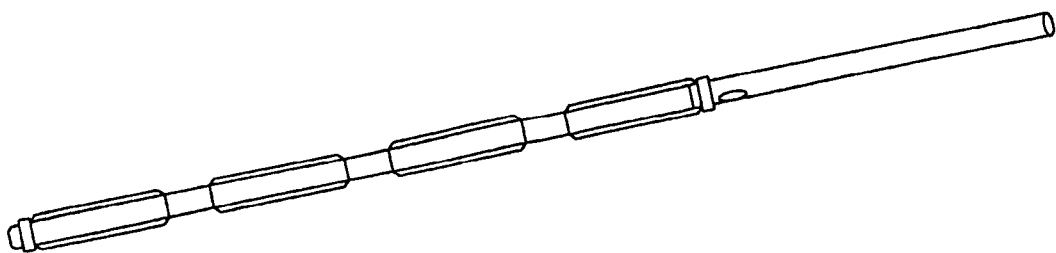
FIGS. 3A-3I show cross sectional views of catheters with various configurations for fluid communication structures.
Figure 3A:
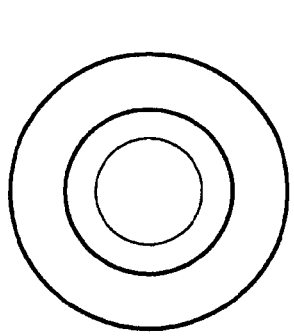
Figure 3B:
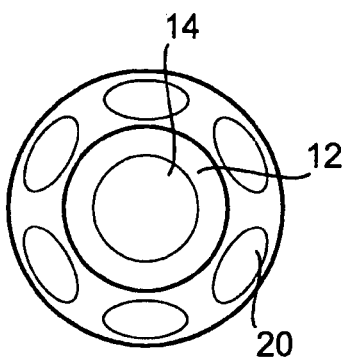

As more clearly shown in FIGS. 3A–3I, each of the fluid communication structures 16 has one or more conduits for allowing fluids and/or gases (hereinafter referred to as fluids) to perfuse across the entire catheter body 12 when inserted in a biological path. Particularly, when the bulk segments 16 meet the duct lumen causing total vessel or duct occlusion, these bulks 16 allow uninterrupted flow of fluids and/or gases through the biological path where the bulk segments 16 meet the duct lumen. FIGS. 3A and 3B show an embodiment of the fluid communication structure 16 in which the catheter body 12 and lumen 14 are centered about the fluid communication structure 16. The fluid communication structure 16 is fenestrated or has a plurality of perforations or micro-conduits 20. The fluid communication structures 16 shown in FIGS. 3A–3I may be used when a doctor desires, or is not concerned with, a partial reduction of flow through the biological path, like for a biological path of small diameter, where a reduction of flow is not considered critical (the catheters may have a diameter of roughly 1.4 mm).

Figure 3C:
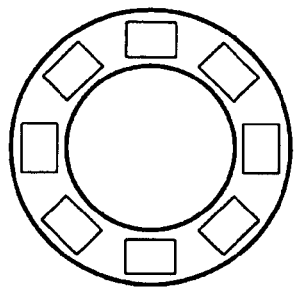
Figure 3D:
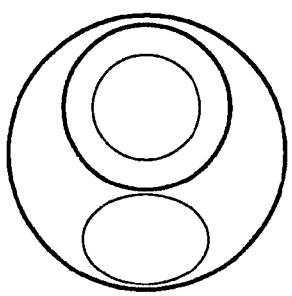
Figure 3E:
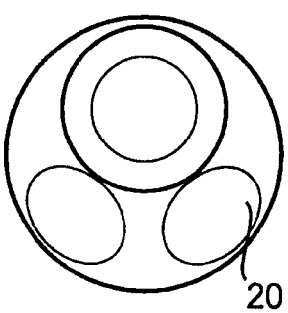
Figure 3F:
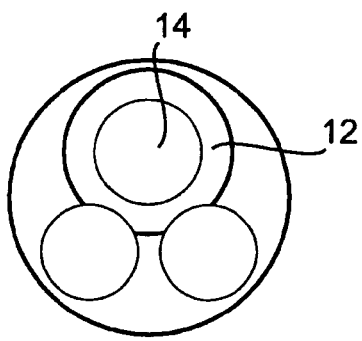
Figure 3G:
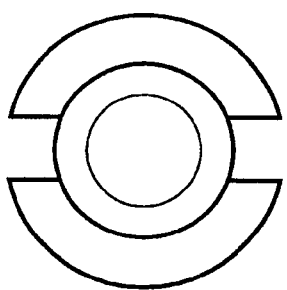
Figure 3H:
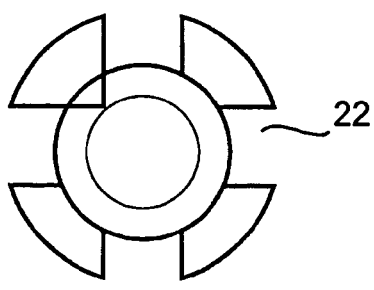
Figure 3I:
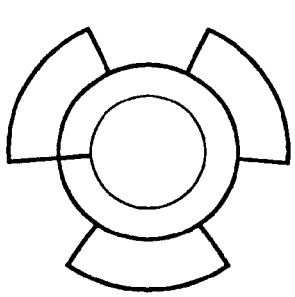

Next, FIGS. 3C–3E show embodiments with different variations in the fluid communication structure 16. In FIGS. 3C, 3D, 3E the catheter body 12 and the inner lumen 14 are not centered within the fluid communication structure 16. The perforations or micro-conduits 20 do not surround the inner lumen 14. These types of fluid communication structures are used when it is desired that the radiation source be placed off center for purposes of providing the proper dosage of radiation to the area to be treated.

FIGS. 3F-3I show three other embodiments of the fluid communication structure 16 which may be used with the catheter shown in FIG. 2. These structures are centered around the catheter body 12 and the inner lumen 14. Channels 22 are formed in the catheter body to allow fluid to flow through the biological path. The embodiments shown in FIGS. 3F-3I are easier to manufacture than some of the alternative perfusion catheter embodiments.

The catheter embodiments shown in FIGS. 3F-3I may be used with or without an additional membrane or stent (not shown) to keep a uniform support to the layers of the biological path (such as the cell walls). The additional membrane may be a netting or other similar material which is used to 1) provide additional support and avoid the prolapse of the tissue of the biological path within the bulks and (2) work as a vehicle for substances to assist in the healing process of the treated (irradiated, drug, and/or dilated) segment (cell wall) after a procedure requiring a catheter has been completed. The membrane, stent [Johnson & Johnson is the leading manufacturer of stents], or netting is introduced into the biological path with the catheter. Preferably, the membrane, stent, or netting surrounds all or a portion of the outside of the fluid communication structure. During the procedure, the membrane, stent, or netting is pressed against the cell wall being treated. When the catheter is withdrawn, the membrane, stent, or netting is left behind to assist the cell wall in healing. Any type of stent, including but not limited to, stents with a sheet cover, stents without a sheet cover, and coil-like stents may be used with the catheter. The disclosure in U.S. Pat. No. 4,733,665 to Palmaz issued on Mar. 29, 1988 entitled "Expandable Intraluminal Graft and Method and Apparatus for Implanting an Expandable Intraluminal Graft" is hereby incorporated by reference.

Referring generally to FIGS. 2, and 3A through 3I, an example of the catheter in operation is provided. A guide wire is placed into the biological path and beyond the place where the treatment is to occur. Then the catheter 10 is placed into the biological path using a rail system attached to the distal end of the closed channel. If the doctor desires, a guide wire is placed in the closed channel formed in the inner lumen 14 to assist the introduction of the catheter in the biological path. The guide wire is then removed and an irradiation source is placed in the closed channel or inner lumen 14. The irradiation source may be attached to the distal end of a metallic wire or other different irradiation source systems (seeds, isotopes, liquid, etc).

Various types of guide wires may be used. For example, a metal wire generally made of nickel preferably with 0.018" diameter or smaller may be used. Guidewires may be removed and replaced during the procedure.

Various irradiation sources such as seeds may be used of varying radiation strengths, sizes, and materials such as strontium 90 or iridium 192. Also, various types of radiation delivery methods may be employed with the multi-purpose catheter. For example, beta or gamma radiation may be used with radioactive fluid, or one or multiple seeds, delivered by guide wire, fluid pressure (water) or other delivery means. In the preferred embodiment, an automatic delivery system with multiple seeds and a wire are used. A guide wire is used to move the irradiation source to the distal end 18 of the closed channel of the inner lumen 14 (or near the end). Usually an automatic machine is used to move the irradiation source to the distal end of the channel using a guide wire. Once the catheter body 12 is in place at the biological path, the fluid communication structures 16 through the perforations or micro-conduits 20 or the channels 22 allow fluids or gases to flow over the catheter body 12, thereby preventing an occlusion at the biological path where treatment is occurring. In this manner, if the biological path is an artery with an occluded or partially occluded area, blood may flow from a point before the occlusion to a point beyond the occlusion.

Also, a guide wire may be used via the over-the-wire system to perform other procedures.

The catheter described above with references to FIGS. 1, 2 and 3A–3I is better suited for smaller arteries in the 1.5 mm to 2 mm range. The catheters are generally disposed after use.

An automatic radiation source delivery in the catheter 10 is preferred since it allows hospital staff to leave the patient during the procedure. Preferably, the radiation is delivered in a closed lumen of the catheter. Furthermore, depending on whether and how well the irradiation source needs to be centered for a particular medical procedure, and the size of the biological path, a catheter 10 having an appropriate fluid communication structure 16 may be chosen.

The larger the biological path the more movement the catheter 10 may have within the path. In alternative embodiments of the catheter 10, a blood pressure monitor is located in communication with the catheter body to determine the blood pressure at the location in the biological path being treated.

To measure blood pressure with the multi-purpose catheter preferably a blood pressure monitoring system is connected to the catheter. Although it is possible to monitor blood pressure with a single lumen catheter, preferably a two lumen catheter is used and one of the lumen's is used to measure blood pressure. The lumen that is used to monitor pressure may have one or more valves which are described below. This lumen is attached to a blood pressure monitoring system using a connection such as a tube, for example, a "K-50" connection. Once the monitor is connected, a sensor such as a drum-like member or transducer of the blood pressure monitor assists in generating blood pressure readings.

As shown in FIGS. 12A–12D, another feature which is used in certain alternative embodiments is a valve 500 for the inner lumen. The valve allows for the opening and closing of the inner lumen. For example, a U-shaped valve may be used in the catheter 10 to open and close the channel in the inner lumen 14. In particular, using a U-shaped valve, provides the user with the flexibility of having a closed or open channel, depending on the position of the U-shaped valve. A U-shaped valve is preferred because it allows for a wide opening, as opposed to a shutter or pivoting valve which will allow approximately half the width of the opening of a U-shaped valve. With a wide opening, guide wires or other tools may be enter and exit at the valve opening. Also, fluids such as drugs or blood may flow through a valve. This allows the valve to be used for dosing a certain specific area with drugs or allowing additional blood flow. While a closed channel catheter may be used to receive a radiation source, an open channel catheter may used to receive other instruments to treat areas of a biological path and for pressure monitoring in the biological (in the path where the catheter exists or beyond the catheter). The valve may be made of various materials such as metal or plastics. A variety of valves may be used with the catheter, for example, a free leaflet or an internal in-channel balloon which can be inflated to close the channel as desired. The U-shaped valve may be retrofit into existing catheters, thereby making the catheters more versatile.

Infusion of drugs is an important use for the valve structure. Vessel changing drugs or intravascular drugs can be infused through the catheter to a selected site. In this manner, a smaller amount of drug will have the desired effect, and the drug affects the selected site and not the entire biological system. For example, continuous infusion of anti-coagulant drugs to a selected site is possible.

Figure 12A:
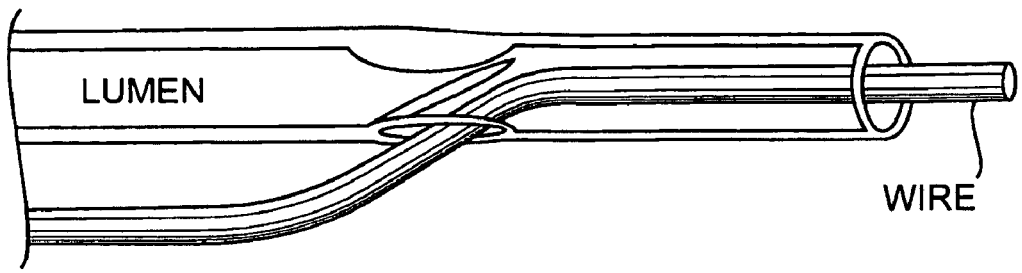
Figure 12B:
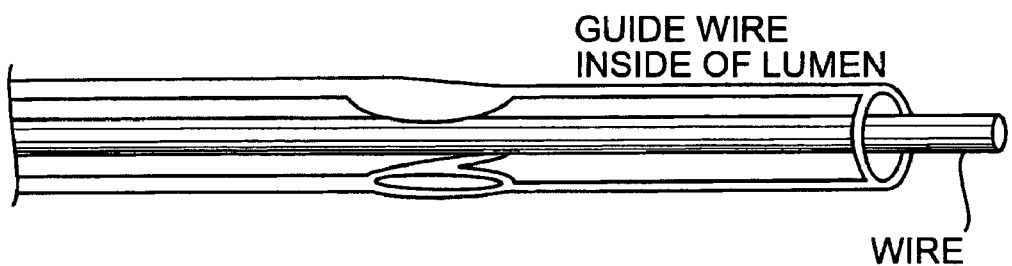
Figure 12C:
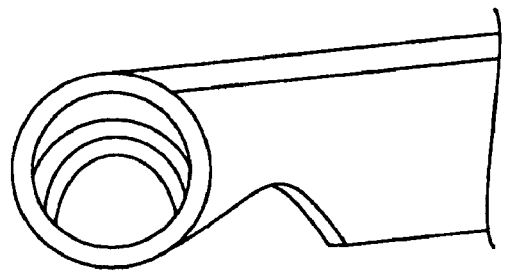
Figure 12D:
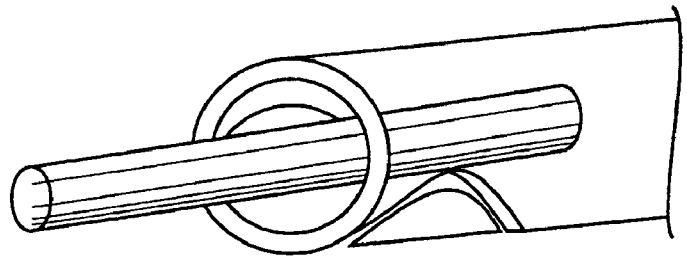

As shown in FIG. 12A, when the valve closes the channel, a guide wire may be introduced through a guide wire entry located distal to the valve. This forms a monorail system. The guide wire exit port allows the guide wire to enter the catheter 10. In the preferred embodiment, the diameter of the guide wire exit port is approximately 0.025 inches. The guide wires are preferably smaller than 0.018 inches. Also, when the valve is open (see FIG. 12B), the guide wire may be introduced through the inner lumen 14, thereby forming an over-the-wire system catheter.

Alternatively, as shown in FIGS. 13A–13F, a microballoon may be used as a valve. The balloon is inflated and deflated through a microconduit formed in the inner lumen. Also, as shown in FIGS. 14A–14F, an inverted or reverse valve may be used. The inverted valve comprises a circular ring with a flat flap hingedly connected to the circular ring.

B. A Catheter with Bulks and Balloons

With reference to FIGS. 4, 5, and 6A through 6H, a second embodiment of the catheter of the present invention will be described. As shown in FIG. 4, the catheter 110 comprises a flexible tubular catheter body 112 having an inner lumen 114, at least one fluid communication structure 116 formed on the catheter body 112 adapted to permit fluid flow through a biological path, and at least one balloon 130 wrapped around the fluid communication structure 116 of the catheter 110. A distal end 118 of the inner lumen 114 is closed, thereby forming a closed end channel. An irradiation source (not shown) may be placed in the inner lumen 114 moved through the inner lumen using a guide wire to the end or near the end of the closed channel. A closed conduit port 124 at the proximal end of the catheter body 112 facilitates the introduction of the irradiation source. In addition, radial opaque markers 126, 127 are located at the extremities of the fluid communication structures 116. The most distal marker 127 marks the end of the closed channel formed in the inner lumen 114. These markers 126 allow a doctor to visually place the irradiation source at the precise location where radiation treatment is required within the biological path.

Figure 5:
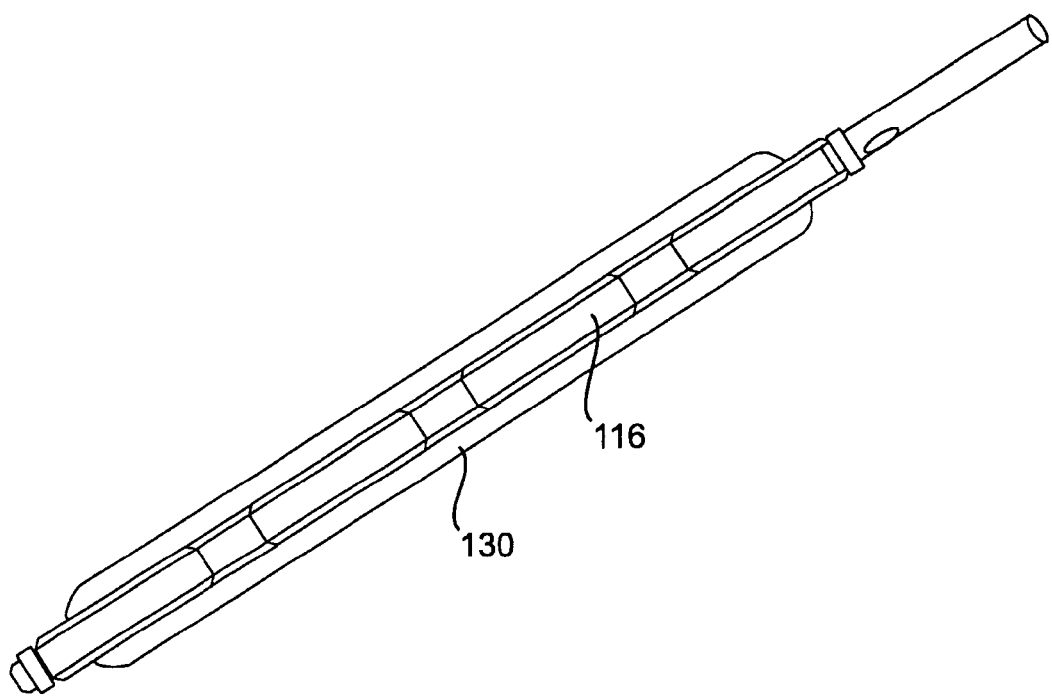
FIG. 5 is an enlarged view of the lower portion of the catheter shown in FIG. 4.

As shown in FIG. 5, the balloon 130 is attached to the catheter body 12 such that the balloon brackets the fluid communication structures 16. This attachment permits the fluids and/or gases flowing through the biological path the flow under the balloon 130. Also, a separate balloon control 150 at the proximal end of the catheter 110 facilitates inflation and deflation of the balloon 130. Various methods of balloon control may be used including microconduits with fluid or gas flow to the balloon. Preferably, this second embodiment with balloon is used in biological path of small diameter when the balloon is deflated or in biological path of larger diameter by inflating the balloon (can be used for larger arteries and blood vessels than the earlier embodiment of FIGS. 1–4). This system works best for arteries of approximately 2 mm to 3 mm. The balloon assists with dilation of the biological path and centering of the radioactive source.

This embodiment also has a guide wire entry port or gate 121 located distally from the balloons and links introduction of a guide wire in the distal end of the catheter. This guide wire entry port allows the catheter to be a monorail system. In addition, gates may be formed proximal to the balloons.

Gates may be formed anywhere on the catheter. If the gate is distal to the balloons, then the guide wire must be pulled out before inflation of the balloons.

In the preferred embodiment with balloon, (1) the catheter 110 is approximately 120 to 140 centimeters in length 150; (2) the proximal segment length 152, which refers to the portion of the catheter from the closed conduit port 124 to the bulks 116 (referred to as the "proximal segment" 111) is approximately 115 to 135 centimeters; (3) middle segment length 154, which refers to the portion of the catheter which contains the bulks 116 and balloons 130 (referred to as the "middle segment" 13), is approximately 3 to 4 centimeters; and (4) the distal segment length 156, which refers to the portion of the catheter 110 that extends beyond the bulks 116 and balloons 130 (referred to as the "distal segment" 15), is approximately 1.5 to 2 centimeters. In the preferred embodiment, the outer diameter 160, 162, 164 of the catheter 110 in each of these segments (i.e., the proximal segment 111, the middle segment 113, and the distal segment 115) respectively is as follows: (1) the outer diameter 160 of the catheter 110 in the proximal segment 111 is approximately 0.039 to 0.045 inches; (2) the outer diameter 162 of the catheter 110 in the middle segment 113 is approximately 0.066 to 0.070 inches, when the balloons are deflated; and (3) the outer diameter 164 of the catheter 110 in the distal segment 115 is approximately 0.039 to 0.045 inches. In the preferred embodiment, in all three segments 111, 113, and 115, the inner lumen 114 has a diameter generally in the range of 0.019 to 0.021 inches. Preferably, this catheter is used in small to medium sized biological paths in the range of 2 mm to 6 mm. With large balloons the catheter may be used even with 10 mm diameter biological paths.

With reference to FIGS. 5 and 6A–6H, the fluid communication structure 116 will be described. At least one fluid communication structure 116 is formed on the body 112 of the catheter 110. As shown in FIG. 5, four fluid communication structures are formed. Any number of fluid communication structures 116 may be formed on the body 112 of the catheter 110. The fluid communication structure 116 shown in FIGS. 5 and 6A–6F also referred to as "bulks" may be formed using teflon, polyurethane, polyethylene, or similar materials. In the preferred embodiment, each of the bulk segments 16 have a length between 3 to 7 millimeters, and the 3 to 4 bulk segments generally span 30 to 40 millimeters of the catheter body 12. The bulk 16 can be fenestrated or solid perforated polyethylene, teflon, polyurethane, or other similar materials. The balloon 130 surrounds the fluid communication structures. This balloon 130 can be inflated and deflated.

As more clearly shown in FIGS. 6A–6H, each of the fluid communication structures 116 has one or more conduits for allowing fluids and/or gases perfuse across the entire catheter body 112 when inserted in a biological path. FIGS. 6A and 6B show an embodiment of the fluid communication structure 16 in which the catheter body 112 and lumen 114 are centered about the fluid communication structure 116 and the balloon 130 surrounds the fluid communication structure. The fluid communication structure 116 is fenestrated or has a plurality of perforations or micro-conduits 120. The fluid communication structures 116 shown in FIGS. 6A and 6B are preferably used when the radiation source needs to be centered within the biological path for purposes of providing the proper dosage of radiation to the area to be treated. The balloon assists in (1) preventing changes in the diameter of the biological path being treated due to mechanically induced spasm or other movement in the biological path; and (2) providing support for or dilation of the walls of the biological paths under treatment. The balloon can additionally be used as (1) a dilation device and as (2) an endoprotesis delivery system.

Next, FIGS. 6C–6E show another embodiment of the fluid communication structure 116. In FIGS. 3C, 3D, 3E the catheter body 112 and the inner lumen 114 are not centered within the fluid communication structure 116 and the balloon 130 surrounds the fluid communication structure. The perforations or micro-conduits 20 do not surround the inner lumen 14. These types of fluid communication structures are used when the radiation source needs to be placed off center for purposes of providing the proper dosage of radiation to the area to be treated.

FIGS. 6F, 6G, and 6H show three other embodiments of the fluid communication structure 16. These structures are centered around the catheter body 112 and the inner lumen 114 and the balloon 130 surrounds the fluid communication structure. Channels 122 are formed in the catheter body to allow fluid to flow through the biological path. The balloon surface forms one side of the channel 122. The embodiments shown in FIGS. 6F–6H are easier to manufacture.

All of the embodiments shown in FIGS. 6A–6H may be used with or without an additional membrane or stent (not shown) to keep the cell walls uniform. This additional membrane would be a rigid or semi-flexible membrane such as netting. The membrane is left in the cell wall to assist the cell wall with healing. The disclosure in U.S. Pat. No. 4,733,665 to Palmaz issued on Mar. 29, 1988 entitled "Expandable Intraluminal Graft and Method and Apparatus for Implanting an Expandable Intraluminal Graft" is hereby incorporated by reference.

Also, as shown in FIGS. 6I–6M, the outer surface of the balloon 130 may form a wavy surface. The wave front is perpendicular to the principal axis of the catheter 110. The number of longitudinal channels formed on the outer surface of the balloon 13 may vary. These longitudinal channels on the outer surface of the balloon allows for fluids or gases to flow through the biological path. In this "wave" embodiment, one or more balloons 130 may be used without the bulks 116. This "wave" embodiment with balloons having longitudinal channels may be formed using a balloon material that has at alternate positions a non-expandable material. Some or all of this non-expandable material is then attached, directly or indirectly, to the catheter body. The difference in expansion between the expandable and non-expandable balloon material helps form the wave shaped outer diameter of the balloon.

Referring to FIGS. 6N through 6R, an alternative embodiment, a local infusion balloon system is shown. One use for the local infusion balloon system is to directly treat a localized area of a biological path with drugs.

In a local infusion balloon system, one or more balloons on a catheter are used to trap or enclose an open area adjacent to the wall of a biological path. This trapped or enclosed area is wholly or partially filled with a substance such as a drug. Preferably, the substance is substantially or completely isolated from other fluids in the biological path (e.g., blood). Various methods may be used to infuse or deliver the substance to the local area including ports, lumens and/or valves.

As shown in FIGS. 6N to 6R, the outer surface of the balloons may form a transverse wavy surface. The number of transverse channels created by the balloon may vary. The transverse channels on the outer surface of the balloon create a "ring" shaped closed area or trap between the outer surface of the inflated balloon and the biological path wall. The closed area is connected to one or more separated proximal infusion ports. The closed area allows the infusion of substances that can exert a local action in a "ring" fashion in the treated segment. Preferably this treatment occurs without interference from the flow through the biological path and without interrupting the flow through the biological path. This transversal wave balloon having transverse channels may be formed using a balloon material that has a ring of a non-expandable material. Some or all of this non-expandable material is then attached, directly or indirectly, to the catheter body. The difference in expansion between the expandable and non-expandable balloon material helps form the wave shaped ring in the outer diameter of the balloon.

Alternatively, two or more balloons may be used to create a closed area or trap. For example, two ring shaped balloons spaced sufficiently apart to create a ring shaped trap along the catheter may be used. The infusion ports are preferably located between the balloons. Preferably, in the local infusion balloon system embodiments, fluids flowing through the biological path flow through microconduits in the catheter body (as shown in FIGS. 6P, 6Q and 6R) and/or through the second lumen leaving the trap undisturbed by biological fluid flow. The local infusion balloon system may be used in combination with other alternative embodiments disclosed.

Examples of the catheter in operation follow. A guide wire is placed into the biological path and beyond the place where the treatment is to occur. Then the catheter 10 is placed into the biological path using a rail system attached to the distal end of the closed channel. If the doctor desires, a guide wire is placed in the closed channel formed in the inner lumen 114 to assist the introduction of the catheter in the biological path. When the fluid communication structure is placed in the area to be treated the balloon is inflated. The guide wire is then removed and an irradiation source is placed in the closed channel or inner lumen 14. The irradiation source may be attached to the distal end of a metallic wire or other different irradiation source systems (seeds, isotopes, liquid). An over-the-wire, monorail, or other approach to using the guidewires may be deployed. After reaching the treatment area, the balloon 13 is inflated. Inflation of the balloon may be used to dilate the biological path as well as centering the closed channel lumen. Usually, the guide wire is then removed and an irradiation source or seed is placed in the inner lumen 114 (or near the distal end). A guide wire is used to move the irradiation source to the distal end 18 of the closed channel of the inner lumen 114. Usually an automatic machine is used to move the irradiation source to the distal end of the channel. Once the catheter body 112 is in place at the biological path, the fluid communication structures 116 (through the perforations or micro-conduits 120 or the channels 122) allow fluids or gases to flow over the catheter body 112, thereby preventing an occlusion at the biological path where treatment is occurring. Furthermore, depending on such factors as whether and how well the irradiation source needs to be centered, size of the biological path, amount of desired flow around the treatment area, a catheter 110 having an appropriate fluid communication structure 116 (and profile) may be chosen. After treatment, the balloon 130 is deflated and the catheter 10 is removed from the patient's body. If a cell wall membrane or netting is used over the balloons, the membrane or netting is left behind in the cell wall.

More than one guidewire may be used with the multi-purpose catheters. Use of multiple wires simultaneously allows for greater manipulation and movement of the catheter during insertion and increases the pushability of the catheter through the biological path. Wires may also be withdrawn and replaced using the catheter.

Alternatively, although FIGS. 4 and 5 show one balloon which extends the entire length of the fluid communication structures 116, several balloons may be used. Several balloons may be attached at desired locations along the entire length and around the total periphery of the catheter body and/or communication structures. Using a series of shorter balloons facilitates the ability to guide the catheter to the location in the biological path that needs to be treated. Several smaller balloons, instead of one or two larger balloons, allow a doctor to more easily maneuver the catheter through the turns required in properly positioning the catheter at the appropriate location. The use of several smaller balloons provides greater flexibility to the catheter than one large balloon.

Furthermore, regardless of the type of balloon used, if several balloons are used, each of the balloons may be inflated and deflated separately from the other balloons. This may be accomplished in a variety of way, including multiple controls or filing the balloons in series instead of in parallel. This ability to independently inflate a balloon allows a doctor to manipulate the distance between a radiation source in the inner lumen 114 and the biological path wall.

Valves may be used in conjunction with the catheter, for example, a U-shaped valve (see FIGS. 12–14) may be used in the catheter 110 to form the closed channel in the inner lumen 114. In particular, using a U-shaped valve, provides the user with the flexibility of having a closed or open channel, depending on the position of the U-shaped valve. While a closed channel catheter may be used to receive a radiation source, an open channel catheter may used to receive other instruments or fluids to treat areas of a biological path, as well as pressure monitoring through the biological path. A variety of valve devices may be used, for example, a free leaflet or an internal balloon which can be inflated to close the channel as desired. With a valve, the catheter can accommodate infusion of drugs and over-the-wire guide wire techniques. When the channel is closed, the guide wire must be introduced through a gate, thereby forming a monorail catheter. When the channel is open, the guide wire may be inserted through the lumen. It should be noted that the U-valve may be retrofit into existing catheters.

C. Two Channel Catheter

With reference to FIGS. 7, 8 and 9A–9F, a third embodiment of the catheter 210 of the present invention will be described. As shown in FIG. 7, the catheter 210 comprises a flexible tubular catheter body 212 having an inner lumen 214, a guide wire channel 215, and a balloon 230 attached to the catheter body 212. A distal end 218 of the inner lumen 214 is closed, thereby forming a closed end channel. An irradiation source (not shown) may be placed in the inner lumen 214. A closed conduit port 224 at the proximal end of the catheter body 212 facilitates the introduction of the irradiation source. In addition, radial opaque markers 226 are located on the body of the catheter. The most distal marker 227 marks the end of the closed channel formed in the inner lumen 214. Through the use of visual monitoring equipment, these markers 226 allow a doctor to visually place the irradiation source at the precise location where radiation treatment is required within the biological path. A guide wire port 229 and a balloon control port 250 are attached to the proximal end of the catheter body 12. The guide wire port 229 facilitates use of the guide wire and the balloon control port facilitates inflation and deflation of the balloon 230. Also, in the length of the catheter one or more guidewire gates may be used.

Figure 19A:
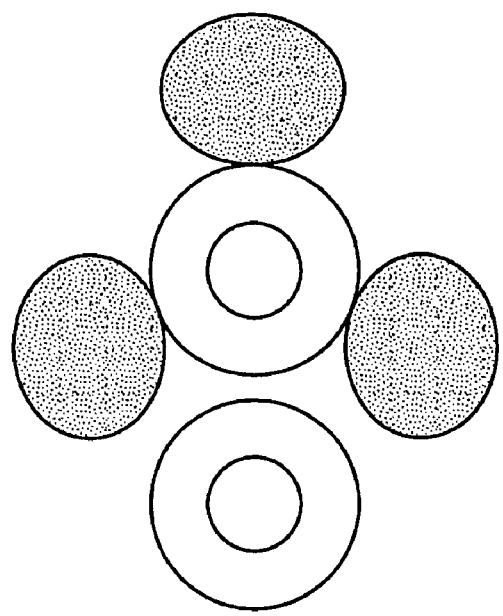
Figure 19B:
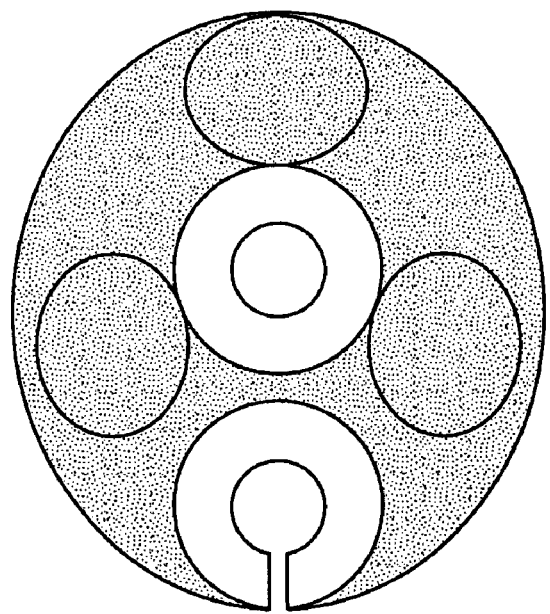
Figure 19C:
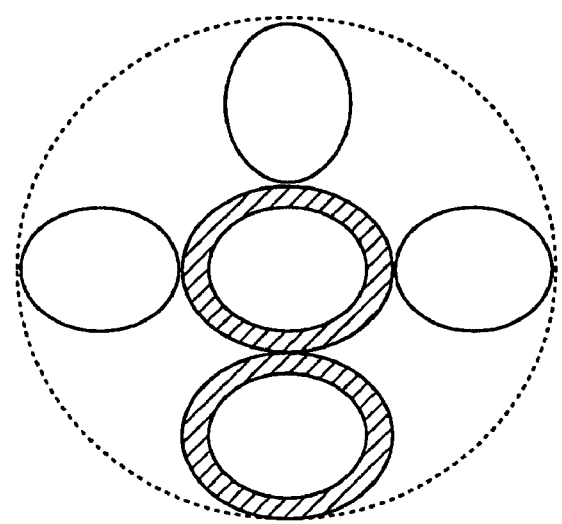
Figure 19D:
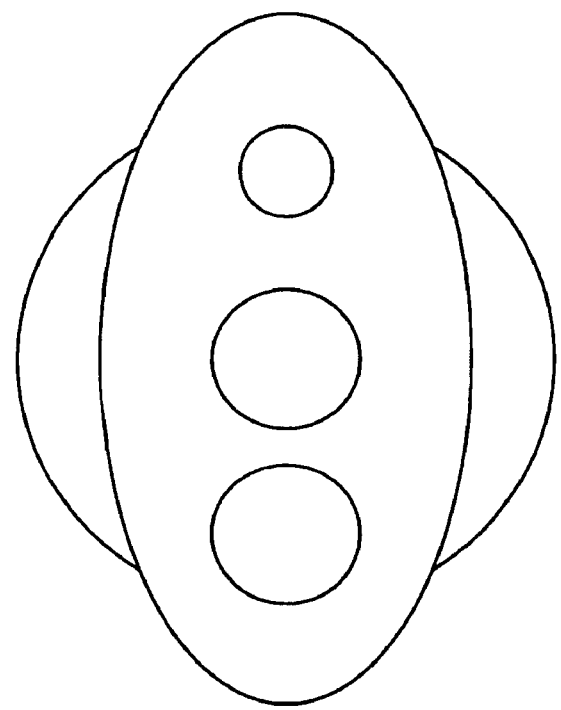

FIGS. 19A, 19B, 19C and 19D show examples using balloons in a two lumen catheter to center one of the lumens in the catheter. The two lumens or channels may be split in the balloon segment of the catheter, allowing the closed end channel to be easily centered within the biological path when the balloons are inflated (in the segment to be treated). In this manner, the radiating source placed in the closed end channel is centered in the catheter. In the embodiment shown in FIGS. 19A, 19B, and 19C, the preferred positioning of the closed end channel is accomplished with three balloons strategically located about the closed end channel. Preferably, one of the balloons is located adjacent to the closed end channel but 180° from the second channel and is roughly the same size as the second channel to center the closed end channel within the walls of the biological path. The catheter body itself may also be used for centering, as shown in FIG. 19D.

With reference to FIG. 8, the perfusion mechanism for this embodiment will be described. As shown in FIG. 8, there are a plurality of perfusion holes 232 in the guide wire channel along the body of the catheter. Also, distal to the balloon 230, there are a plurality of perfusion holes or openings 234. In the preferred embodiment, three perfusion holes in distal to the balloon 230 are aligned with the guide wire exit port 229. In operation, when the catheter is positioned in the area to be treated and the balloon 230 has been inflated, the biological path is not occluded because fluid and/or gas may flow (1) through the perfusion holes 232 located in the guide wire channel 215 or the microconduits (shown in FIGS. 9B–9D) and (2) the area between the balloons 237 and (3) the microconduits 238 formed on the body of the catheter. There are two guide wire exit ports at the extremes of the perfusion holes. Also, this embodiment also has a guide wire entry port (or gate) located distally of the balloons, thereby forming a monorail system. Several guide wire entry ports or gates may be located along the catheter. The guidewire entry ports are particularly useful on either side of the balloons or balloons segment.

As shown in FIGS. 9A–9F, the catheter 10 may be constructed without perfusion holes. As more clearly shown in FIGS. 9A–9F, there are various perfusion configurations possible using this two channel catheter. The shape (i.e. the figure "8" in FIG. 9A) or the microconduits in FIGS. 9B and 9C allow perfusion of fluid. The microconduits permit fluid flow along the body of the catheter. Furthermore, in FIGS. 9D and 9E, the balloons for paths that allow for fluid perfusion. The balloon configuration shown in FIGS. 9D and 9E enable centering of the radiation source in the biological path. Centering the radiation source is important to obtain optimal and proper dosage of the radiation. The configuration of FIG. 9A may be implemented without perfusion holes. However, when microconduits are used to allow fluid perfusion, at least one perfusion hole in either side of the middle segment is needed to channel fluid into the microconduits.

Also, with regard to the positioning of these perfusion holes, the perfusion holes may form a straight line on the catheter body. However, in the preferred embodiment, the perfusion holes should not be in a straight line.

In the preferred embodiment, (1) the catheter 210 is approximately 120 to 140 centimeters in length 250; (2) the proximal segment length 252, which refers to the portion of the catheter from the closed conduit port 224 to the balloons 230 (referred to as the "proximal segment" 211) is approximately 115 to 135 centimeters; (3) middle segment length 254, which refers to the portion of the catheter which contains the balloons 130 (referred to as the "middle segment" 213), is approximately 3 to 4 centimeters; and (4) the distal segment length 256, which refers to the portion of the catheter 210 that extends beyond the balloons 230 (referred to as the "distal segment" 215), is approximately 1.5 to 2 centimeters and can be as long as 2 to 5 centimeters. Also, the distal segment is soft and has a low profile (i.e. a diameter smaller than the rest of the catheter). In the preferred embodiment, the outer diameter of the catheter 210 in each of these segments (i.e., the proximal segment 211, the middle segment 213, and the distal segment 215) respectively is as follows: (1) the outer diameter 260 along the long axis 270 of the catheter 210 in the proximal segment 211 is approximately 0.068 to 0.078 inches; (2) the outer diameter 261 along the short axis 272 of the catheter 210 in the proximal segment 211 is approximately 0.039 inches; (3) the outer diameter 262 along the long axis 270 of the catheter 210 in the middle segment 213 is approximately 0.068 to 0.078 inches, when the balloons are deflated; (4) the outer diameter 263 along the short axis 272 of the catheter 210 in the middle segment 213 is approximately 0.039 inches; and (5) the outer diameter 264 of the catheter 210 in the distal segment 215 is approximately 0.039 to 0.045 inches. In the preferred embodiment, in all three segments 111, 113, and 115, the inner lumen 114 the guide wire channel have a diameter generally in the range of 0.019 to 0.021 inches. The perfusion holes have a diameter of approximately 0.013 inches. Finally, the guide wire exit port has a diameter of approximately 0.025 inches. Although this catheter will be employed in procedures for larger biological paths, it is still preferred that the profile of the catheter be low profile or small, preferably 2 mm or less.

For example, in operation, a guide wire is placed into the biological path and beyond the place where the treatment is to occur. Then the catheter 10 is placed into the biological path using a rail system attached to the distal end of the closed channel. If the doctor desires, a guide wire is placed in the closed channel formed in the inner lumen 14 to assist the introduction of the catheter in the biological path. When the fluid communication structure is placed in the area to be treated the balloon is inflated. The guide wire is then removed and an irradiation source is placed in the closed channel or inner lumen 14. The irradiation source may be attached to the distal end of a metallic wire or other different irradiation source systems (seeds, isotopes, liquid). Over-the-wire, monorail, multiple wire, and other wire insertion/removal techniques may also be employed. An irradiation source, seed, liquid, etc. is placed in the inner lumen 214 and a guide wire may be used to move the irradiation source to the distal end 218 or near the distal end of the closed channel of the inner lumen 214. Usually, an automatic machine is used to move the irradiation source to the distal end of the channel. Once the catheter body 212 is in place at the biological path, the perfusion holes 232 and 234 allow fluids or gases to flow through the catheter body 12, thereby preventing an occlusion at the biological path where treatment is occurring. Furthermore, depending on whether the irradiation source needs to be centered a catheter 10 having an appropriate fluid communication structure 16 may be chosen.

The two channel, two lumen catheters, are easily configured with two guide wires to provide greater versatility during insertion and maneuvering. These two channel catheters may be used in larger arteries and veins. The two channels provide the user with the flexibility to use two guide wires to position the catheter. The stiffer the guide wire, the more "pushable" is the catheter. However, for maneuverability a more flexible guide wire is preferred. With two wires, the user can control the stiffness and flexibility as desired in order to more effectively position the catheter.

As with the other embodiments described previously, a membrane, netting, or stent may be used to cover the catheter prior to insertion.

Figure 11A:
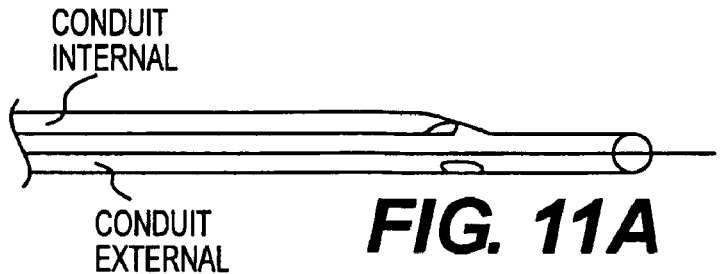
Figure 11B:
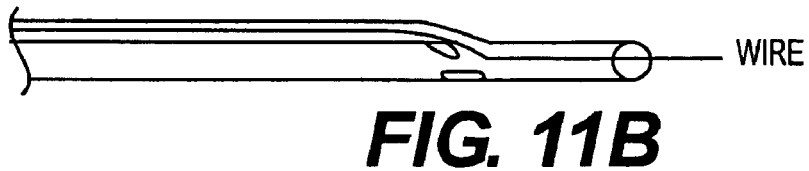
Figure 11C:
Figure 11D:
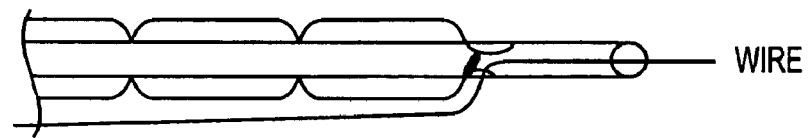
Figure 11E:
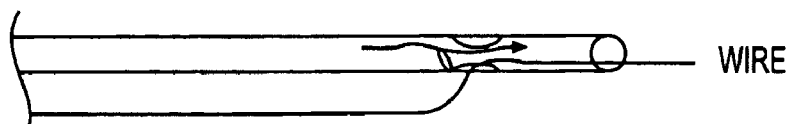

Also, as with the other embodiments, valves may be used in the catheter. Preferably, a U-shaped valve shown in FIGS. 15A–15C, 16A–16C, and 17 may be used in the catheter 210. The valve permits the inner lumen 214 or the guide wire channel to act as a closed or open conduit. As shown in FIG. 15A, the valves may close both channels. The guide wire is introduced through the guide wire entry port located distally to the valves. This is an over-the-wire system. When a channel is open, the guide wire may be introduced in that channel. In this embodiment, the closed channel may be used for irradiation and the channel may be used for perfusion, dilation, and/or infusion of drugs. As shown in FIGS. 10A–10C and 17, a balloon or an inverted valve may be used as valves for the two channel system. As shown in FIGS. 11A and 11B, the valve has means to close the conduit when the guide wire is introduced in the guide wire channel or as shown in FIG. 11C, the valve can open when the guide wire is introduced in the inner lumen 214 from the distal to the proximal segment. The valve system can be any valve means as for example a free leaflet or an internal balloon which can be inflated to close the channel as desired. Various metallic microvalves may be used. Also, the valves may be retrofit into existing catheters. The valve is a retrograde system such that the U-valve may be used in existing catheters to provide the versatility described above.

The second lumen or channel in a two lumen catheter can be used for a variety of procedures, for example, a) infusion of drugs in localized segments of a biological path, b) monitor pressure (blood pressure) at a particular location in biological path, c) allow for blood flow (perfusion) around an occluded area, d) use with wire, and e) changing the guide wire [for example, the wire in the first lumen]. Valves and holes maybe used in one or both lumens to accommodate various uses. For example, for blood perfusion around an occluded or partially occluded area using a second lumen or channel, a valve or holes in the second channel upstream of the occlusion and a valve or holes downstream of the occlusion allow blood to flow past the occluded area. The first lumen may remain sealed in such an embodiment so that a closed system may be used for simultaneous radiation treatment. In this manner, one catheter may be used for dilation, radiation, perfusion around an occlusion and even infusion of drugs.

FIG. 10 shows another embodiment of the present invention in which another layer of balloons is wrapped around the catheter shown in FIGS. 7–9. Also, FIGS. 10A–10D show the microconduits and a perfusion channel to allow the flow of fluids through the catheter body. In the preferred embodiment, the perfusion holes are not in a straight line. Moreover, the perfusion holes in the distal segment are not in line with the perfusion channel. As shown in FIGS. 18A–18D, the outer surface of the balloon 230 may form a wavy surface. The wave front is perpendicular to the principal axis of the catheter 210. The number of longitudinal channels formed on the outer surface of the balloon 230 may vary. These longitudinal channels on the outer surface of the balloon allow fluids or gases to flow through the biological path. This embodiment with the balloons having longitudinal channels may be formed using a material that has at alternate positions a non-expandable material. Some or all of this non-expandable material is then attached, directly or indirectly, to the catheter body.

In addition, a membrane, netting, or stent may be wrapped around the balloon. This membrane is then deployed against the cell walls during the procedure.

FIGS. 20 to 26 show a versatile alternative embodiment for a catheter system and structure that can be used for a variety of procedures including radiation treatment.

Referring generally to FIGS. 20 to 26, a versatile alternate embodiment is described. The following alternative system or structure for a multi-purpose catheter has the versatility to be used with other conventional catheters (for example, angioplasty catheters), is able to create a closed system which can be used to introduce encapsulated wires with radioactive sources, permits catheters which transport the source of the radioactivity to be a simple fixed tube, or it can create a system of veins and conveying canals for the displacement of fluids which transport the radioactive material.

The object of this embodiment is to maintain profusion during the necessary time to effectuate radiation treatment either vascularly or across a biological canal. It is also an object of this catheter to accurately and precisely place a radioactive source with a high degree of security, in a particular location within a body for radioactive treatment. It is also an object of this alternative embodiment to avoid traumas and spasms and be stable during any traumas or spasms in the area of treatment.

This alternative structure uses a system of tubes or canals. The tubes or canals can be balloons, microtubes, and/or can allow for the passage of wires, catheters or other canals within them. Generally, the design consists of a single tube (or one tube concentrically located within another tube) which then branch out into a system of two or more canals for a relatively short distance and then these separate canals recombine into a single canal or a single canal containing within it other canals. It can also be described as a single tube or canal branching out into two or more tubes reconnecting or joining into a single tube. Each canal or tube may also contain other canals or tubes within them.

Generally speaking, this embodiment can be described as having three basic parts.

FIGS. 20, 21, 22, and 23 show the overall structure of the alternative embodiment of a catheter system. Specifically, FIG. 20 shows the outside of the system along with cross-sectional views of certain portions of the system. More specifically, FIG. 20 shows an inner portion 1012 and an outer porter 1010. This depicts a system where you have an inner tube or balloon 1012 and an outer tube or balloon 1010. Cross-sections A, B, and C of FIG. 20 show the inner and outer diameters of the two tube or two balloon configuration. This configuration has an entry end 1016 and a distal end 1014. FIG. 20 is a relatively simple configuration which allows a catheter to pass through from the entry end 1016, and through the inner balloon or tube to the distal end 1014. Various types of catheters may be used which can pass through the system shown in FIG. 20. Alternatively, the catheter may be attached at either the entry end 1016 or distal end 1014.

FIG. 21 shows a somewhat more intricate variation of the system shown in FIG. 20. FIG. 21 shows four openings or passages: an opening in the distal end 1014, a second opening 1020 near the distal end, an opening 1028 at the balloon structure, and an opening at the entry end 1016. In FIG. 21 we see a similar inner area 1012 and outer area 1010 configuration as seen in FIG. 20. However, in FIG. 21 there is an inflator tube 1024 (or catheter) which extends from the entry end 1016 to the distal end 1014. The inflator tube 1024 includes two openings in the tube 1020, 1028 and a series of micropores 1032. Towards the distal end 1014 there is an opening 1020 which can be used for guide wires and the like. There is an opening 1028 which can be used for a form, explained below. And, there is also a series of micropores 1032 toward the entry end 1016.

FIG. 21 also shows three alternative cross-sectional views of the center of the structure which may be used with the system. In cross-section inflator tube 1024 passes through the outer section or outer tube 1010 outside of inner tube 1012. In cross-sections B and C various configurations for an outer tube or balloon 1010 are shown. Various configurations for microtubes or microballoons 1036 are possible within the outer tube structure 1010. The inflator tube may pass inside or outside (within or outside) of other microtubes or balloons, as is shown in FIG. 21, cross-sections B and C.

Before describing the variations shown in FIGS. 22 and 23 in detail, a brief description of the components used for the structure of the system (shown in FIGS. 24a, 24b and 24c) follows.

FIG. 24a depicts the inflator tube by itself. The inflator tube 1024 includes distal end 1014, entry end 1016, an opening 1020 near the distal end 1014 which can be used as a guide wire opening, the form opening 1028, and the micropores shown as 1032.

Preferably the inflator tube 1024 has a slight bend or archway in its path so that it will rest towards the walls of the biological path rather than in the center of the biological path. The shape or form of the inflator tube 1024 can be provided by its inherent shape or by one or more forms which may be placed towards the entry end 1016 and or towards the distal end 1014. One such form is shown in FIG. 24b.

The micropores 1032 of the inflator tube 1024 are used to fill or inflate balloons or tubes in the system. Preferably, the micropores 1032 allow for passage of fluid from the inflator tube 1024 directly to the inflatable tubes. Alternatively, or additionally, provisions are made for a tube, catheter or other device which may enter from an opening (for example, distal opening 1020) and pass through the inflator tube 1024 to the micropores 1032. Fluids, air or the like may be forced through the micropores 1032 to fill tubes or balloons. Preferably the microtpores 1032 are smaller than any wires used in the inflator tube 1024, for example in the range of 0.005 to 0.013 inches.

A catheter or catheter-like device may be used as an inflator tube 1024 or conduit instead of a specially constructed tube or conduit. If that is the case, and the inflator tube 1024 is to run the entire distance necessary in the biological path, then the catheter is preferably long enough to be positioned in any biological path of the body. The system should allow for the passage of angioplasty equipment, such as a standard wire used in angioplasty. Typically these wires are metal of approximately 0.014 to 0.018 inches. The inflator tube canal or inner portion of the inflator tube can run the entire length of the catheter. When a wire is introduced into this canal which runs the entire length of the catheter, the stiffness of the wire increases support for the catheter. The support is helpful when the catheter and catheter system is being introduced and when it is being moved around. The wire also changes the flexibility of the catheter and can be withdrawn when a different flexibility is desired. This inflator tube canal is used to fill the system of balloons or tubes which are used in the catheter system.

FIG. 24b is the form 1040. The form has a body 1044 and arms 1048. Angles are formed between the body 1044 and arms 1048. Preferably, the angles are shallow. The particular embodiment shown in FIG. 24b has two arms 1048. It is preferred that the form 1040 have one body 1044 which can fit in the canal of the inflator tube 1024 at either the entry end 1016 or the distal end 1014. The form 1040 may have as many arms 1048 as a designer feels necessary to maintain the general shape and relative position of the various inflatable tubes to the inflator tube 1024. Each arm 1048 preferably enters or slides into a balloon or tube. The form helps to maintain the overall shape and structure of the system, particularly when the catheter system is deployed in a biological pathway and the tubes are filled. Preferably the form 1040 is made of material which is slightly stiffer or firmer than the remaining material which is used for the catheter. Plastics or metals may be used for the form 1040. Various other materials known in the art of manufacturing catheters may be used for the form and the various parts described for this system.

In addition, the form 1040 can act as the radiological mark or marker for the system, being viewed on a television screen during use. In this manner, the form 1040 can be used to align the catheter system to the appropriate place in the biological path where treatment is to occur.

Also, if the micropores 1032 of the inflator tube 1024 (located in the vicinity of the entry end 1016) and the form 1040 towards the distal end 1014 (using hole 1028), are used, then the form 1040 can serve the additional purpose of being the block or closing point of the inflatable balloons, inflatable tubes, or inflatable canals. The inflatable components can be inflated using the micropores 1032. In this way, the inflatable tubes will be inflated from the entry end 1016 towards the form 1040 located near the distal end 1014 where the tubes are blocked by the form 1040.

In alternative system configurations, forms 1040 may be used on either the entry end 1016 or distal end 1014 or forms 1040 may be used on both ends.

FIG. 24c shows a balloon system 1050 made up of multiple balloons or a single balloon system which is formed with segments 1060 in the center. The balloon structure 1050 has a short end 1052, a long end 1056, segments 1060 and union 1064. The short end 1052 is typically where the balloon structure 1050 meets the distal end of a catheter. The segments 1060 form the largest or fattest part of the multiple balloon system 1050. Each of these segments 1060 can be a separate balloon, connected balloon, tube, or microtube. Alternatively, if this is a single balloon system the segments 1060 are all joined and inflated in unison.

The number of segments desired depends on factors, such as the procedure involved, the size of the biological path, whether stents are being used, whether there is profusion or passage of fluids and how much, and other possible factors such as the size of the segments 1060 or balloons. Therefore, the number of segments 1060 used can be adjusted or adapted to the situation.

The union 1064 is a union of the segmented balloons in which the balloons all join. In a configuration where all the segments 1060 are inflated simultaneously, the union 1064 allows the passage of the inflating gases or fluids. The union 1064 also allows the passage of catheters, wires, radioactive sources and the like through the balloon system. The longer end 1056 preferably corresponds to the entry end 1016 of the catheter and, if used, inflator tube 1024. Both ends 1052 and 1056 can be wrapped with material, shrunk, and/or filtered and attached to a catheter. Various methods for attaching the balloon structure 1050 are possible.

If the balloon system is of a single balloon structure 1050 then only one inflation device or one micropore 1032 is needed. If each of the segments 1060 are individually filled then each segment 1060 may have its own micropore 1032. Each segment would then be connected in some manner to a micropore 1032 either through additional tubing or directly connected to the micropore 1032. In a multi-balloon configuration each of the segments 1060 would be an inflatable tube or inflatable microtube. The system can also be configured with one micropore 1032 to fill or service each inflatable tube. With one micropore 1032, a device to maneuver to and fill each inflatable tube is used.

Preferably the balloon structure 1050 is made with a central conduit or canal for a wire or a catheter to pass through the balloon structure 1050 with relative ease. Preferably one of the segments 1060 can perform this function and provide the centrally located canal in which to pass catheters, wires, radioactive sources through the balloon structure 1050.

FIGS. 24*d* and 24*e* show catheters which can be used with the system structure shown in FIGS. 20 through 26. The catheter shown in FIG. 24*d* is a simple catheter, while the catheter shown in FIG. 24*e* is a balloon catheter 1072. The catheters shown, and others, can be used with this system and which the structures shown in FIGS. 24*a*, 24*b* and 24*c* can be attached to the catheter. Both the simple catheter 1068 of FIG. 24*d* and standard balloon catheter 1072 of FIG. 24*e* can include radiological markers.

Having described the individual or component parts of the system, referring back to FIG. 21, other features of the system will be described.

FIG. 21 demonstrates the assembly of the parts, inflator tube 1024, form 1040, balloon system 1050 and catheter 1068. In FIG. 21 the inflator tube 1024 is assembled with a balloon structure having an inner area 1012 and an outer balloon area 1010. When a catheter is used with the system, the catheter may pass through entry end 1016 to enter the system.

A connecting means 1076 is used to assemble the components. This connecting means 1076 may be a wrap or a melt or other connection devices described herein. The connecting means connects the inflator tube 1024 to the balloon system 1050. Using this type of connection the catheter can then pass through openings 1028 and 1020 relatively unimpeded and unattached to the system structure.

In the embodiment of FIG. 21, it is preferred that a catheter is used as the inflator tube 1024. The catheter (inflator tube 1024) is shown inbetween the inner and outer balloon structures 1010 and 1012 and can be attached to the inside walls of the balloons. The catheter as the inflator tube 1024, exits the distal end 1014. Cross-cut A depicts the catheter and the room created between balloons 1010 and 1012. Other than in the area of opening 1028, the inner and outer balloon areas may be loosely connected or may be free from attachments to each other.

FIGS. 22 and 23 show variations to the basic system shown in FIGS. 20 and 21. In particular, FIG. 21 shows an inner opening 1012 of a balloon structure which is generally one opening or tube. FIG. 22 and FIG. 23 show embodiments having multiple tubes or multiple segments 1060 which are inflatable.

FIG. 22 and FIG. 23 differ in two primary ways. They differ in the use of the form 1040 and in the type of union 1064 that is used. Specifically, no form is used in the embodiment of FIG. 22 and the union 1064' is larger and encompasses each of the tubes. While in the embodiment shown in FIG. 23 a form 1040 is used with three arms 1048 and a narrower or single union 1064" is used. In FIG. 22 the union 1064' is used to maintain the shape in relative positions of the balloon segments 1060. While in FIG. 23, the form 1040 is used to maintain the shape and relative position of the segments and not the union 1064".

FIG. 22 shows cross-sections A, B, C, D, E and F. Cross-section A at the distal end 1014 depicts the cross-section at the area prior to the distal opening 1020. Cross-section B depicts the cross-section at the area of the means for attaching 1076. Cross-section C depicts the cross-section at the opening 1028. Cross-section D depicts the cross-section at the center of the structure and includes a cross-section of the inflator tube 1024 in one of the balloon segments 1060. Cross-section E shows the cross-section at the area of the union 1064' and micropores 1032 and cross-section F shows a cross-section located near the distal end 1016.

FIG. 23 shows similar cross-sections to FIG. 22 but the cross-sections also depict the form 1040 with its arms 1048.

The cross-sectional view D of FIG. 22 shows the tubular shape of the balloon segments or microtubes 1060.

A catheter can be run through and within the inflator tube 1024 of the system and out the distal end 1014. Alternatively, a catheter can be run through and within the inflator tube 1024 to the micropores 1032. By maneuvering the catheter through the inflator tube 1024 to the micropores 1032 the catheter can then be maneuvered to inflate or deflate particular balloon segments or inflatable microtubes 1060.

FIG. 23 best depicts the use of form 1040 with the system. In particular, it demonstrates the use of a form 1040 with three arms 1048 and a body 1044. In the embodiment shown in FIG. 23 the form arms 1048 are used to position certain of the balloon segments 1060 or microtubes but not all. It is possible to configure the form to have an arm 1048 for each particular segment or microtube 1060. Using the embodiment of FIG. 23, a catheter may enter the structure or system, at entry end opening 1016 and pass through the balloon structure 1050.

FIG. 25 shows use of the novel system or structure with a simple catheter 1068. In this embodiment the distal end of the catheter 1080 is shown anchored to the system or structure. More specifically, the catheter 1068 is shown anchored at its distal end 1080 to form 1040. In this specific embodiment, one of the arms 1048 of form 1040 is used to anchor the catheter to the system or structure. The catheter passes through the structure entry opening 1016, passes through the union 1064 and through the center of the structure to arm 1048 of form 1040.

Several cross-sections are shown of the structure in FIG. 25. A cross-section A is shown at the attachment area 1076 where the form 1040, inflator tube 1024, and balloon structure 1050 are attached and shown. Cross-section B of FIG. 25 shows two arms 1048 of form 1040, including a center arm which anchors the catheter. Cross-section C of FIG. 25 shows the catheter anchored in the center arm 1048 as well as an arm 1048 which is in the inflator tube 1024. Using this configuration, the form 1040 maintains the position of the inflator tube 1024 and the catheter relative to each other. Preferably, the inflator tube and the anchored catheter form an arch with a shallow angle. Other microtubes are shown which assist to center the catheter in the biological path.

Cross-section D shows the middle of the structure with the catheter in the center and the inflator tube 1024 at the top. Cross-section E shows the positioning of the inflator tube 1024 and the catheter 1068 at the union 1064. In cross-section F at end 1016 of the structure shows the positioning of the inflator tube 1024 and the catheter 1068 exiting the novel structure of the invention.

Also in this alternative embodiment, a radio marker 1086 is shown used on the simple catheter 1068 to help with the precise and accurate placement of the catheter and structure in the area of treatment in the biological pathway. Alternatively, the form 1040 can be used as a marker. Once the structure shown in FIG. 25 with the anchored catheter is accurately placed in a section of the biologically pathway to be treated, the micropores 1032 may be used to inflate the balloon segments or inflatable microtubes 1060. The microtubes or segments 1060 can be inflated until the structure rests snugly against the walls of a biologically pathway. This positioning will limit the movement of the catheter structure and center the catheter within the biological pathway. It is also possible to use stents with this embodiment and structure shown in FIG. 25.

FIG. 26 is a similar embodiment to FIG. 25. More specifically the novel additional structure and system which is added or anchored onto the catheters in FIG. 25 and FIG. 26 can be identical. The difference between FIG. 25 and FIG. 26 is that FIG. 26 uses a balloon catheter 1072 rather than the simple catheter 1068 of FIG. 25. The embodiment shown in FIG. 26 is likely to be more useful in larger biological pathways.

Again, as shown in FIG. 25, the catheter 1072 shown in FIG. 26 is anchored to the novel system and structure. The catheter is anchored on an arm 1048 of form 1040 like being anchored on one finger of a glove.

Both embodiments shown in FIG. 25 and FIG. 26 can be used for radiation treatment within biological pathways. The embodiment shown in FIG. 26 is more likely to occlude a greater portion of the biological pathway and partially occlude or prevent the passage of fluids.

FIG. 26 shows a cross-section A at the attachment point 1076 which shown the form 1040 body 1044. Cross-section B is shown at the point where the catheter is anchored to the arm 1048. This cross-section shows the relationship positioning and angle of the inflator tube 1024, catheter 1072 and arm 1048. Cross-section C is taken in the relative center of the novel structure and shows the inflatable catheter 1072 in an inflated state. Each of the balloon segments or microtubes 1060 are positioned around the outside of the inflated catheter 1072. Cross-section D shows the inflator tube 1024 and catheter as both exit the novel structure.

Again, micropore 1032 can be connected to the microtubes or segments 1060 to allow for the inflation of the segments 1060. Alternatively, a catheter or other device can pass within the inflator tube 1024 to the micropores 1032 and be maneuvered or manipulated to reach the segments or inflatable microtubes 1060 through the union 1064 and the segments or microtubes 1060 can then be filled with a device that has been maneuvered through the micropores and to the individual segments.

Thus, this novel structure or system can be added to a simple catheter 1068 or an inflatable catheter 1072 which are commonly available. By adding this novel system or structure to an existing catheter a user can benefit from additional features without redesigning the catheter. This add-on system or structure can be easily used and retrofitted to currently available equipment.

Various multipurpose and versatile catheters and catheter systems for biological paths have been described. One and two lumen catheters with various fluid communication structures and balloon structures have been described. Many different types and configurations of fluid communication structures, including bulks, micro-conduits, micro-balloons, channels and balloons have been described. Various methods of controlling the fluid communication structures have been described. Combinations of valves, stents, balloons, and guide wires as well as visual and pressure monitoring devices may be used to form numerous embodiments. Various insertion techniques and medical procedures including radiation treatment may be accomplished with the catheters and systems described. All of these apparatuses and methods are within the scope of this invention.

II. Systems for Catheter Manipulation and Structural Support

Various systems using wires, balloons, cords and combinations thereof may be used for catheter manipulation and structural support.

A. Systems of Catheter Manipulation and Structural Support with a Wire.

One or more preformed metallic wires can facilitate the manipulation and enhance the structural support of catheters when introduced into the vascular systems or other body tracts. The structural support wires may be made of materials other than metal.

Manipulation. The use of preformed angiographic catheters for the purpose of manipulating the catheters into the coronary arteries for angiography has been known for several decades.

Although the use of preformed guiding catheters can be used to facilitate the placement of guiding catheters in PTCA, operators continue to encounter difficulty in placing these guiding catheters into the opening of the selected coronary artery. The anatomical relationship of the left coronary artery to the retrograde approach of the catheter through the aorta makes positioning in the left coronary artery particularly difficult.

By adding a preformed metallic wire to the catheter, greater structural support is provided to the operator. This additional structural support would facilitate the insertion of the guiding catheter into the preferred coronary artery.

A wire may be passed through the principal lumen of the guiding catheter. Alternatively, a wire could be passed through an accessory lumen of the guiding catheter. Similarly, the advantages of the invention might be achieved by incorporating metal wires into the wall of the guiding catheter or in a channel or rail system attached to the wall of the guiding catheter.

Structural Support. A guiding catheter that is already situated in the selected vascular structure or other lumens (with or without the assistance of the present invention) can achieve additional structural support by the insertion (or further insertion) of one or more metal wires. The insertion of one or more metal wires would help to maintain the position of the guiding catheter (or a guide wire) during manipulation or the passage of an object through the lumen, such as a balloon catheter.

The metal wires can be passed through the principal lumen of the catheter or through an accessory lumen. In addition, the advantages of the present invention might be achieved by incorporating metal wires into the wall of the guiding catheter or in a channel or rail system attached to the wall of the guiding catheter.

B. Systems of Catheter Manipulation and Structural Support with a Balloon.

A set of inflatable balloons can facilitate the manipulation and enhance the structural support of catheters when introduced into the vascular system or other body lumens. Preferably, these balloons are strategically located on the catheter.

Manipulation. One or more inflatable balloons may be placed on the acute and/or obtuse angles of preformed catheters. When it is desirable to increase the curve or a preformed curve in a catheter, a balloon attached to the acute angulation, when inflated, can stretch the angle of the curve. The angle of the curve is increased by, for example, the balloon pushing out a cord or nondistensible membrane attached to both sides of the angulation. When the balloon is deflated, it decreases the (pushing) pressure on the cord or membrane and the angle returns to the preformed shape of the catheter. When it is desirable to increase the obtuse angulation of a preformed curve in a catheter, the inflation of a balloon attached along the angulation of the catheter may help attenuate the curve of the catheter. This effect is reversed by deflating the balloon attached along the angle of the catheter. The proper combination and amount of inflation and deflation will facilitate the manipulation and proper placement of the catheter.

Structural Support. A catheter that is already properly situated in the selected vascular structure (with or without the use of the present invention) can achieve additional structural support by the inflation or deflation of eccentrically located balloons located in acute and/or obtuse angles of the catheter. When it is desirable to increase a curve (or a preformed curve) in a catheter, a balloon attached to the acute angulation, when inflated, can stretch the angle of the curve by pushing out a cordate or non distensible membrane attached to both sides of the angulation. When the balloon is deflated, it decreases the (pushing) pressure on the cordate or membrane, and the angle returns to the preformed shape of the catheter. When it is desirable to increase the angulation of a preformed curve in a catheter, the inflation of a balloon attached along the obtuse angulation of the catheter may help attenuate the curve of the catheter. This effect is reversed by deflating the balloon attached to the catheter. The inflation or deflation of the balloons would help to maintain the position of the catheter during manipulation or the passage of an object through the lumen, such as a balloon catheter.

C. Systems of Catheter Manipulation and Structural Support with Cords.

One or more cords attached to the distal arm of an angulation in a curved catheter can facilitate the manipulation of the catheter and enhance the structural support of a catheter when introduced into the vascular system or in other body lumens.

Manipulation. One or more cords may be attached to the proximal and distal arm of angulation on preformed catheters. These cords may be placed on acute or obtuse arms of angulation. By manipulation by the operator, the length of the cord or pressure on the cord may be increased or decreased, to change the shape of the preformed catheter. When it is desirable to keep the angle of a preformed curve in the body of the catheter, the system includes a cord attached to the distal arm of the acute angulation, which then travels along the inner aspect of the catheter curve to reach a proximal cord port. The pulling or pulling out of the cord by the operator, can keep or close the angle of the curve, while decreasing the pull on the cord permits the catheter to return to the preformed angulation. When it is desirable to open the angle of a preformed curve, a cord attached to the distal arm of the obtuse angulation, which travels along the external aspect of the catheter curve can be used to pull open the angle of the catheter. The proper combination of shortening and extension or pulling of one or more cords will facilitate the manipulation and proper placement of the catheter.

Structural Support. A catheter that is already properly situated in the selected vascular structure (with or without the assistance of the present invention) can achieve additional structural support by the shortening or lengthening of the distance between the proximal and distal attachment of a cord. When it is desirable to keep the angle of a preformed curve in the body of the catheter, the system may include a cord attached to the distal arm of the acute angulation. This cord travels along the inner aspect of the catheter curve to reach a proximal cord port. The pulling or pulling out of the cord by the operator, can maintain or close the angle of the curve. While decreasing the pull on the cord permits the catheter to return to the preformed angle. When it is desirable to open the angle of a preformed curve, a cord attached to the distal arm of the obtuse angulation (which preferably travels along the external aspect of the catheter curve) can be used to pull open the angle of the catheter. The shortening or lengthening of the cord (or pressure on the cord) would help to maintain the position of the catheter during manipulation or the passage of an object through the lumen, such as a balloon catheter, or other manipulation.

The systems of manipulation discussed can be used separately or combined. Each system of manipulation can also be used as a system of structural support independently or in combination.

Similarly, the systems of structural support discussed can be used separately or combined. Each system of structural support can also be used as a system of manipulation independently or in combination.

Moreover, it would be clear to those skilled in the art that the systems of manipulation and structural support could be combined and used in all available combinations.

Several embodiments of the invention are described below.

FIG. 1 shows the coronary circulation including RCA=right coronary artery, LCA=left coronary artery, SEPT=septal perforator, CFX=left circumflex artery, PDA=posterior descending artery, CFX-MARG=circumflex marginal branch, LAD=left anterior descending, LAD DIAG=diagonal branch.

The following embodiments shown in FIGS. 28a through 30g are for use primarily in the right and left coronary artery. These embodiments may have uses in other locations within the body and the invention may be used in various locations in the body. FIG. 27 shows the aorta and the left and right coronary artery, along with various other blood vessels in which the invention may be used.

D. Wire Systems.

FIGS. 28A through 28D and FIGS. 28E through 28I show embodiments using a wire system.

Figure 28A:
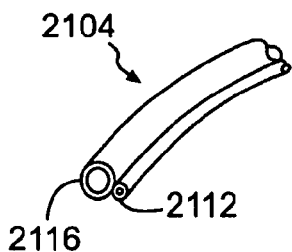
Figure 28B:
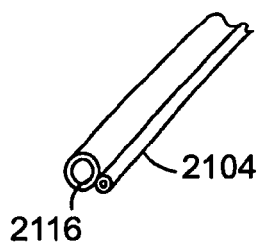
Figure 28C:
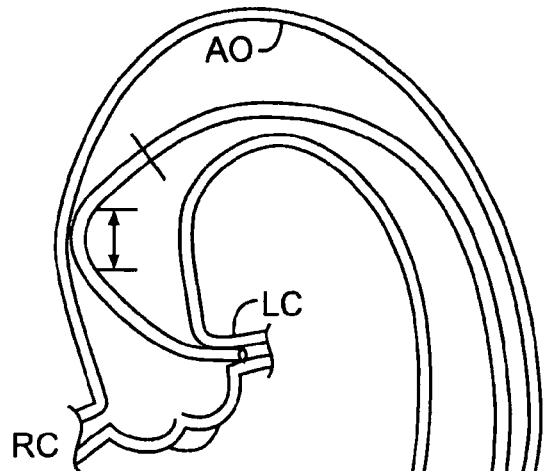
Figure 28:
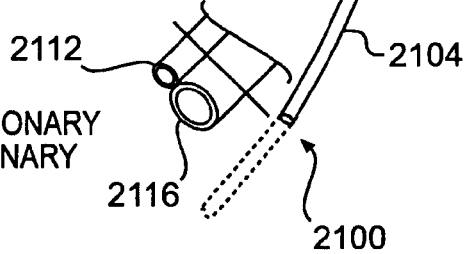
Figure 28D:
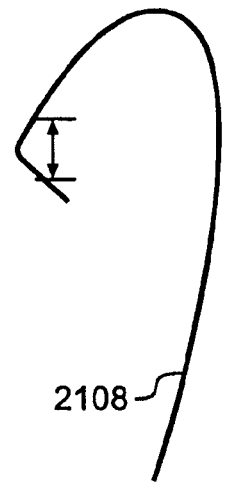

FIGS. 28A through 28D show an embodiment of a wire system 2100 for use in accessing the left coronary artery or blood vessels that are accessible through the left coronary artery such as those shown in FIG. 27. Specifically, FIG. 28c shows a guiding catheter 2104 which has been led or is being led through the coronary aorta to the left coronary artery. FIG. 28d shows a preformed left coronary wire 2108 which is a flexible metal material preformed with the hook and bend as shown in FIG. 28d. The preformed left coronary wire 2108 makes it easier for the user to guide the catheter 2104 to the left coronary artery (beyond the aorta arch) and more importantly to maintain the position of the catheter 2104 in the left coronary artery.

This embodiment may be used with a (1) guiding catheter 2104 that was initially placed with no wire, (2) with a guiding catheter 2104 that already has a wire (e.g., monorail or wire in the lumen system) in which after the preformed left coronary wire 2108 is added will have two wires, or (3) can be used with a catheter 2104 in which a first guiding wire (not shown) is removed and the preformed left coronary wire 2108 is inserted replacing the first guiding wire. The preformed left coronary wire 2108 may be inserted in the catheter 2104 either inside of a lumen or inside of a monorail.

Figure 28E:
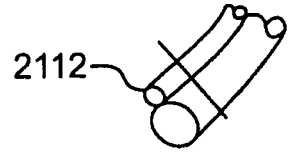

FIGS. 28a and 28e show a cross-section of a monorail embodiment wherein there is an opening for a channel 2112 in addition to the lumen 2116. FIG. 28b shows a lumen 2116 for an embodiment in which a preformed left coronary wire 2108 would be inserted inside of the lumen 2117.

By using the preformed left coronary wire 2108, a doctor or user is able to assist the catheter 2104 in bending at the important location a small distance before the entrance to the left coronary artery. The preformed left coronary wire 2108 can also be used to facilitate bends at other locations of the catheter 2104. As described earlier, the ability to bend the catheter 2104 around the curve (aorta arch) and into the left coronary artery can be difficult at times. Also, it can be difficult to maintain the guiding catheter 2104 in the left coronary artery while introducing guidewires or balloons through the guiding catheter 2104 to be passed on through into the left coronary arteries or blood vessels after the left coronary artery.

FIGS. 28E through 28I show an embodiment for a wire system 2100 to be used for entrance into the right coronary artery.

Maneuvering or maintaining in place a guiding catheter 2104 in the right coronary artery is somewhat different than moving or maintaining a guiding catheter in the left coronary artery because the angles and curves to reach the right and left coronary artery are different. Generally speaking, the right coronary artery is easier in that it does not require as sharp a turn or bend in the guiding catheter 2104 to be made or maintained as that which is necessary for the right coronary artery.

Figure 28F:
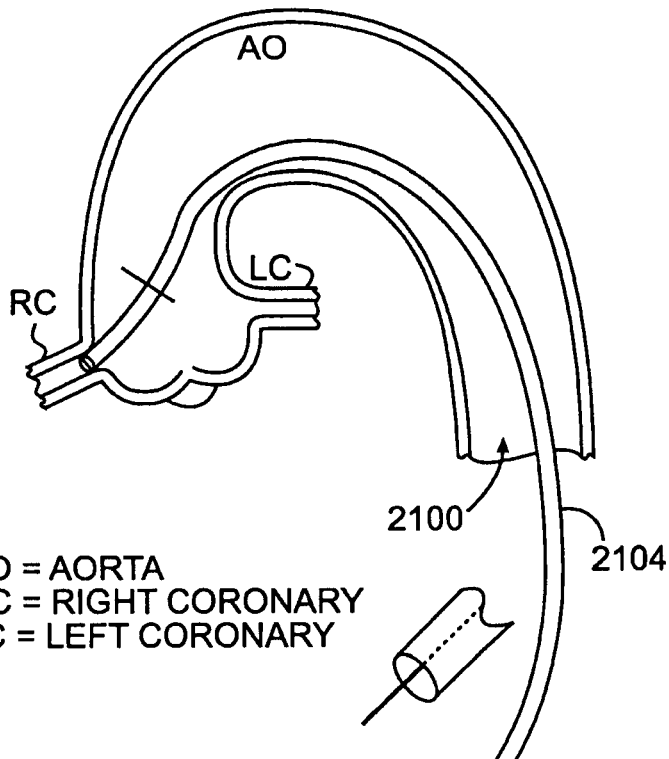
Figure 28G:
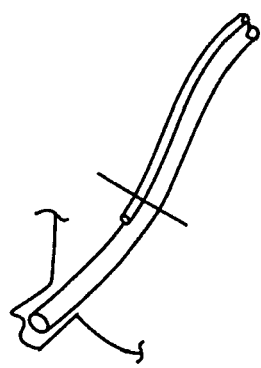
Figure 28H:
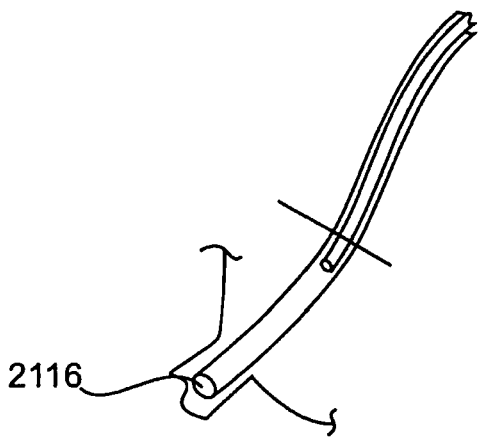

FIG. 28F generally shows a guiding catheter 2104 in place in the right coronary artery. The guiding catheter 2104 of FIG. 28E may be either a monorail, as shown in FIG. 28E and FIG. 28G, or may be an open lumen 2116 as shown in FIG. 28H. Again, as described in FIGS. 28A through 28D, the preformed wire, in this case a preformed right coronary wire 2120, may be placed either in the monorail track 2112 shown in FIGS. 28E and 28G or may be passed through the lumen 2116 as shown in FIG. 28H.

Figure 28I:
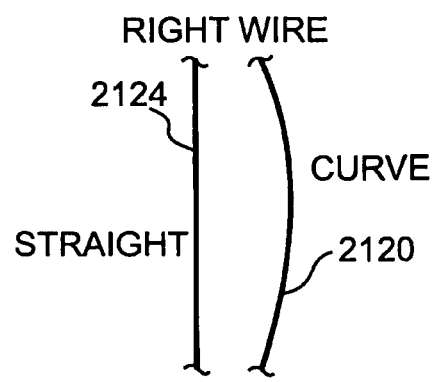

FIG. 28I shows a piece of wire 2124 which is not preformed, as well as the preformed wire 2120. The preformed right coronary wire 2120 has a left curve, enabling the guiding catheter to be led or held in place at the entrance of the right coronary artery. In the preferred embodiment, this right coronary wire 2120 is made of flexible metallic material which is then preformed. The preformed right coronary wire 2120 can be used to maintain the positioning of the guiding catheter 2104 in the right coronary artery while another wire or balloons are passed through the guiding catheter 2104 into the right coronary artery or arteries which lead from the right coronary artery.

The novel method for guiding a catheter to a coronary artery and around curves or bends in the artery using the wire system comprises guiding a guiding catheter to the vicinity of a coronary artery, inserting a preformed coronary wire into the catheter, and guiding the guiding catheter around or passed the curve or bend in the coronary artery. Additionally, the step of guiding the catheter can be performed with a guide wire. This guide wire may remain in the catheter or be removed prior to insertion (or replacement) by the preformed wire. This method of using the preformed wire catheter is particulary useful for the aorta arch of the left coronary and the entrance to the right coronary artery.

E. Balloon Systems.

FIGS. 29A through 29F show embodiments of the present invention utilizing a balloon system 2130 to change the shape or deform, or maintain the shape and position of a catheter. More particularly, a balloon system 2130 may be used to assist in bending a catheter 2104 around a curvature in a biological vessel (e.g., aorta arch), or bending a catheter 2104 in order to facilitate a change in direction or turn in the direction of a catheter 2104. These balloon systems 2130 may be used either to maintain the position of the catheter 2104 to avoid movement or dislocation of the catheter 2104 while the catheter 2104 is being used to pass other items through the catheter 2104, or may be used to facilitate in the guiding of the catheter 2104 into place.

FIG. 29a shows the use of a balloon system 2130 of the present invention on a catheter placed in the left coronary artery. Specifically, FIG. 29a shows a membrane 2134 connected to two points on the catheter 2104 which is engaged by a balloon 2138 to cause the bending of the catheter 2104 or the maintenance of a bend in the catheter 2104 while the catheter 2104 is in the left coronary artery. Preferably, the balloon is attached at two different longitudinal positions along the length of the catheters, but with the same radial measurements (or location).

FIG. 29b shows the membrane 2134 connected at two places (active locations) along the path of the catheter 2104 with the balloon 2138 deflated. When the balloon 2138 is deflated, the membrane 2134 allows the catheter more flexibility and does not "hold" the bend in the catheter 2104 or maintain the catheter in the bent position that occurs when the balloon is inflated.

FIG. 29c shows the balloon 2138 inflated, and the distortion in the shape of the membrane 2134 and the bending or maintaining of a bend in the catheter 2104 that is caused by the inflation of the balloon 2138 against the membrane 2134. Preferably, the balloon 2138 is positioned between the outer wall of the catheter 2104 and the inner wall of the membrane 2134. The balloon 2138 can be inflated using commonly known techniques and those described herein. As the balloon 2138 is inflated it will apply pressure on the membrane 2134 and cause the catheter 2104 to take a bent position. Various materials may be used for the balloon 2138 and for the membrane. As shown in FIG. 29a, the membrane 2134 and balloon 2138 combination is located prior to the guiding catheter's 2104 entrance into the left coronary artery.

Generally, the membrane 2134 shown should be attached radially in the same position or same side of the catheter so as to make the catheter bend rather than twist (however, under certain circumstances twisting may be desired). The membrane 2134 should be made of a flexible material that is stiff enough to cause bending and flexible enough not to tear.

FIGS. 29d through 29f show an embodiment of a guiding catheter 2104 utilizing a balloon system 2150 to enter or maintain the guiding catheter's position in the right coronary artery. FIG. 29d shows the guiding catheter 2104 making essentially a left curve and then a right curve to enter into the right coronary artery (a two dimensional pictorial of the actual positioning of the guiding catheter in the right coronary artery). Near the apex of the left curve shown in FIG. 29d, an inflated balloon 2138' is shown. A magnification of the inflated balloon 2138' is shown in FIG. 29f while a deflated pictorial of the balloon 2138 and the guiding catheter 2104 is shown in FIG. 29e.

By inflating the balloon 2138' shown in FIGS. 29d, 29e and 29f, the flexion of the catheter 2104 is changed. By changing the flexion of the catheter 2104, specifically making the catheter 2104 change directions after its left curve, it facilitates the guiding of the catheter or maintenance of the catheter in the right coronary artery.

It is preferred that the balloon 2138' be attached to the catheter 2104 and follow along a length of the catheter. Preferably, the length of the balloon 2138' is longer than the curve of the bend being negotiated by the catheter 2104.

The balloons 2138' may be inflated and deflated using commonly known techniques. The catheter 2104 used in the balloon system 2150 may be a guiding catheter 2104 or other type of catheter 2104. The cather 2104 may be of the monorail type and include a wire.

F. The Cord System.

Figure 30D:
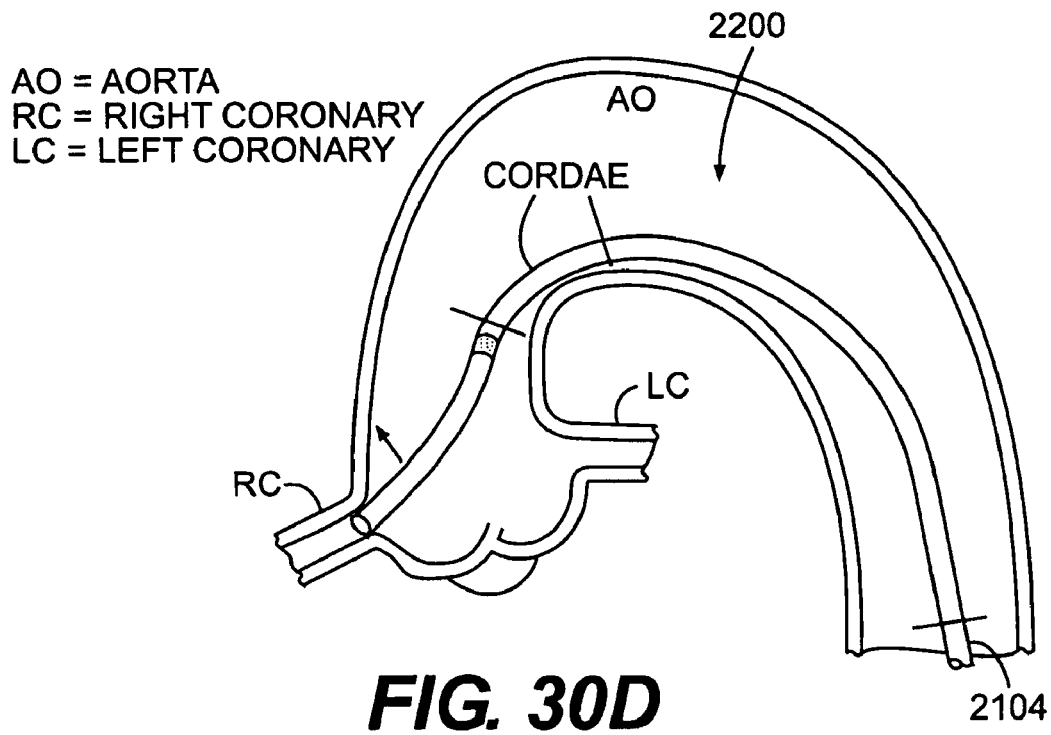

Referring to FIGS. 30a to 30c, similar to the preformed wire system 2100 and balloon systems 2150 described earlier, the cord system 2200 is another apparatus and method (using a cord), to facilitate the positioning of a catheter 2104 or the maintenance of a catheter 2104 in a particular position. In the cord embodiments 2200, a cord is used instead of a balloon 2138 or wire 2108, 2120 to change the direction and shape or maintain the shape of a catheter 2104 which has been inserted into a biological path. A cord or other object similarly positioned and attached may be used in the embodiments shown in FIGS. 30a to 30g. The cord can be made from a variety of materials, for example nylon, plastic and/or biodegradable materials.

As can be seen by an examination of the location of the cord 2204 in FIGS. 30a through 30d, the active cord locations are somewhat similar to the locations of the membrane 2134 for the balloon system 2150 embodiment. As with the membrane 2134, the active cord locations may be located at other positions along the catheter 2104. Preferably, the cord 2204 is anchored at one longitudinal location (first location) towards the distal end of the catheter 2104 and makes contact with the catheter at a second longitudinal location further from the distal end of the catheter. It is preferred that the cord not be anchored at the second location but be free to move or travel through the location. The cord 2204 may enter (or exit) the catheter at this second location thereby providing the contact with the catheter necessary to cause flexing but still allow for the code to be pulled through the second location.

FIGS. 30a through 30g depict embodiments using a cord system 2200. Specifically, FIGS. 30a through 30c relate to the use of a cord system 2200 and a guiding catheter 2104 which is being used to access the left coronary artery while FIGS. 30d through 30g depict a guiding catheter 2104 with cord 2204 which is being used to access the right coronary artery.

FIG. 30a shows that a cord 2204 is attached to the guiding catheter 2104 at a location which is before the entrance of the catheter 2104 to the left coronary artery. At this point, the cord 2204 is attached to the catheter 2104 and sits on the outside of the catheter 2104 and winds its way back to the catheter (or inside the catheter) and through the length of the catheter 2104 until it reaches a position outside the body (not shown). Other methods of attaching the cord 2204 are apparent to persons skilled in the art. Preferably the cord is either inside the lumen 2116 in the catheter 2104 or inside a monorail 2112 in the catheter 2104 from a point outside the body along the length of the catheter 2104 to a point past the left curve (aorta arch) which the catheter 2104 makes in FIG. 30a. At some point after the left curve but prior to the counter-clockwise bend in the catheter, the cord 2204 exits the body of the catheter 2104 and proceeds in a slack or loose fitting manner to its point of connection to the catheter 2104. The cord 2204 can be attached to the catheter 2104 in a variety of fashions. For example, the cord 2204 can be tied to the catheter, melted onto the catheter, or placed within the platic of the catheter during manufacture.

FIG. 30b shows a cross-section of the guiding catheter shown in FIG. 30a. In particular, FIG. 30b is a depiction of a monorail guiding catheter 2104' which is a preferred catheter for use with a cord system 2200.

FIG. 30c shows a cross-sectional view of a bent catheter 2104 in a different location in the aorta (shown in FIG. 30a) than the cross-section view of FIG. 30b. FIG. 30c is also a depiction of a cross-section of a monorail catheter 2104. Preferably the cord 2204 passes through the monorail 2112 shown in FIGS. 30c and 30b.

In operation, the cord 2204 functions by being pulled or tugged so as to take up the slack in the cord 2204 from the position that it exits the catheter 2104 to the point that is connected to the catheter 2104. When this slack is taken up, and the cord 2204 is pulled taught, the catheter 2104 will bend or flex. The cord 2204 is pulled and the catheter 2104 is bent to the point where the doctor or user needs, as necessary, to ensure the guiding or placement of the catheter 2104 into the left coronary artery. Therefore, by tightening the cord 2204 and removing the slack in the cord 2204 that would normally exist, the guiding catheter 2104 is bent or maintained in a bent position.

Figure 30E:
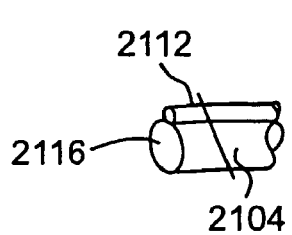
Figure 30F:
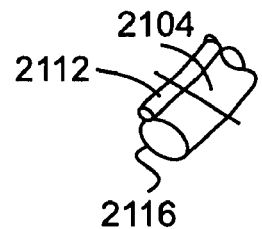
Figure 30G:
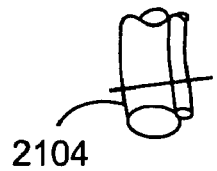

FIGS. 30d through 30g show another embodiment of the cord system 2200 for use with a monorail guiding catheter preferably for use with a monorail guiding catheter 2104' entering the right coronary artery. FIG. 30d depicts the guiding catheter 2104 making a left curve followed by a right curve prior to entering the right coronary artery (a 2 dimensional picture of a 3 dimensional situation). FIG. 30d shows the cord 2204 attached to the catheter 2104 prior to the catheter 2104 entering the right coronary artery. In this particular embodiment, the cord 2204 may either be within the monorail track 2112 of the guiding catheter 2104 or may exit the monorail track 2112 of the guiding catheter 2104 at a point shortly before its end or connection to the catheter 2104. FIGS. 30e, 30f and 30g show cross-sections of the guiding catheter 2104 or 2104' with the cord 2204.

In operation, when the cord 2204 is pulled taught it will change the flexion of the catheter 2104 particularly with respect to that portion of the catheter 2104 towards the end of the catheter 2104. By pulling on the cord 2204 and changing the flexion, it is easier to maintain the catheter 2104 in place or guide the catheter 2104 into the right coronary artery. The cord 2204 can be attached to a variety of locations on the catheter 2104 depending upon the location of the desired flexibility in the catheter 2104.

Although this embodiment shows that the cord is generally within the catheter 2104, it is possible to have the cord located outside of the catheter and still achieve generally the same results.

While a wire system 2100, balloon system 2150 and cord system 2200 were described separately, it is possible to use one or more of these apparatuses or methods in combination. The apparatuses and methods described here may be used on many different catheters 2104, including multi-purpose catheters. For example, the apparatuses and methods described for supporting or tracking a catheter 2104 may be used in connection with the multi-purpose catheters described herein.

III. Systems and Methods for Delivering Radiation

The present invention is a safer and more secure system for providing local radiation treatment especially with regards to commonly related medical problems. The present invention can be used intravascularly to irradiate areas developing blocks. It is possible, using the wire system of the present invention, to only radiate an intravascular area and avoid performing PTCA.

The present invention relates to a wire, more particularly a wire system to carry or transport a radioactive source in a medical procedure. The wire system has a nonradioactive portion and a radioactive portion. The wire system may include a drive cable and an internal support, such as a stud.

Preferably, the wire system is used with a special catheter having a closed end channel. During a medical procedure, this catheter is introduced into a biological pathway which contains and/or is in the vicinity of tissue to be treated with an ionizing radiation. The catheter may be introduced into the patient in various way including by puncture or surgical incision. The wire is introduced into the closed end channel of the catheter. Using the preferred wire and catheter, a radioactive source can be configured, deployed, positioned, moved, retrieved, changed, etc.

There are many radionuclide sources that can be used with the present invention in a biological pathway. Generally, the sources are categorized as beta or gamma emitters and as high energy or low energy emitters. Beta emitters deliver doses within a well defined range. Typically, beta emitters deliver doses of radiation that penetrate less than one centimeter of tissue. Gamma emitters can deliver doses that penetrate longer distances. The fall-off of the dose rate from gamma emitter point source generally follows the inverse square law and is effected by the tissue absorption.

Since the radiation from gamma emitters can penetrate tissue for longer distances (even while a high energy gamma emitter (such as Iridium 192) is in the patient), it may pose an irradiation hazard to the nearby medical staff. Also, a beta emitter which has been deployed shallowly or near the skin of a patient can pose a hazard to nearby medical staff.

The radiation dosing needed to cause a particular biological effect on a tissue depends upon several factors including: (a) the capability of the primary radiation source to emit radiation (energy level of emitter), (2) the time the tissue is exposed to the radiation, and (3) the distance from the radiation source to the targeted tissue.

These factors should be considered when choosing a wire system and radiation source for a particular medical procedure. In addition to the various types of radiation sources that can be used such as Iridium 192 (gamma), strontium 90 (beta), Yttrium 90 (beta), Phosphorous 32 (beta), and combinations thereof, these sources may take a variety of sizes, shapes and forms and may be delivered to the targeted tissue are in a variety of methods. For example, the radioactive source may take a liquid or a solid form. Also, the source may, for example, be formed within a metal wire, formed around a metal wire, or formed within a catheter. The present invention includes new sizes, shapes, forms and new delivery methods for the radioactive sources used in biological paths.

Wire delivery methods and wire systems are preferred over other types of methods. Various catheters may be used in combination with wire delivery methods. Preferably, the wire is flexible enough so that it will smoothly follow the curves in a biological path, but stiff or sturdy enough to accurately transmit precise mechanical motions without buckling.

The radioactive portion of the wire may range from a length of roughly 1 mm to 55 mm. Different lengths are preferred for different medical procedures primarily depending upon the size of the area to be treated. Generally, wires with between 3 mm to 30 mm radioactive lengths are preferred. For safety reasons, the radioactive portion or sources of the wire system should be secured or locked to the nonradioactive portion.

The non-radioactive portion or drive cable portion of the wires can be made from a variety of metals. However, the non-radioactive or drive cable portion is preferably made from Nitinol (Nickel-Titanium), Titanium, or steel. Preferably, the wire is radiopaque and has a diameter of between 0.009–0.020 inches (0.02–0.5 mm).

In the preferred embodiments, the radioactive portion of the wire delivery system can be separated from the non-radioactive portion of the wire. For example, the radioactive portion may be interchangeable with other radioactive portions to allow greater ease in manufacturing of variations. More specifically, different interchangeable radioactive portions using different sources, sizes, strengths, or shapes of radioactive material may be constructed. This provides the medical staff greater flexibility in choosing a particular radioactive wire delivery system and source for a particular procedure. The radioactive portions or sources may be interchangeable, removable, replaceable, etc. It is preferred that the radioactive portions and sources be locked or secured into position to avoid the radioactive portions or sources detaching, slipping, unwinding, or being lost during a medical procedure. It is also preferred that the radioactive portions or sources be covered or wrapped during the procedure.

As explained further below, even the sources themselves can be constructed in blocks or parts and therefore, many variations in sources, size, strength and or shape of the radioactive sources are possible. Using a building block type approach, the radioactive portion and sources can be constructed in a nearly infinite number of variations. Each block or radioactive portion of the tip can be a separate interchangeable and/or lockable piece which when combined form the radioactive portion for a wire delivery system. There are numerous useful variations in size, shape, radioactive strength and material for the radioactive building blocks. Some of the preferred pieces or blocks are described below.

Several wire system embodiments are described below.

FIGS. 31*a*, 31*b*, 31*c* and 31*d* show embodiments of a wire for use with the present invention. The wire 3100 in FIGS. 31*a* through 31*d* comprises a drive cable 3104 and a stud 3108. The drive cable 3104 and stud 3108 may be connected in a variety of fashions. For example, the drive cable 3104 and stud 3108 may be formed from a single piece of metal, the drive cable 3104 and stud 3108 may be glued, threaded, push-in connected, push-in and lock connected, or bolted. Typically the drive cable 3104 is made of nitenol nickel, titanium, steel or other metallic material. Preferably the drive cable 3104 is a radiopaque wire with a diameter roughly in the range of 0.009–0.020 inches, 0.02–0.5 mm. The stud will usually have a smaller diameter than the drive cable 3104 as shown in FIGS. 31*a* through 31*d*. Although, under certain circumstances, it may be desirable to have a stud of equal or greater diameter.

The stud may have a smooth finish such as shown in FIG. 31*a*, a rough finish such as that shown in FIGS. 31*b* and 31*d* and/or a coiled finish, such as that shown in 31*c*. The finish or surface of the stud 3108 depends primarily upon the type of radioactive source or radioactive container which will be used with the stud. For example, if a coiled radioactive source will be used with the stud 3108, a coiled finish or surface, such as that shown in FIG. 31*c* is preferred.

It is preferred that the stud 3108 be provided with a head 3116 which is larger than the length or body of the stud 3108. The stud head 3116 is used to assist in fixing or connecting the radioactive source on the stud 3108. Also, a stopper 3120 may be used with, on, or over the stud head 3116. The stopper 3120 also helps to hold the radioactive sources in place, fixed, connected or on the stud 3108.

FIG. 31*d* shows an example of a stopper 3120 fitting over the stud head 3116.

The drive cable 3104 is nonradioactive or substantially nonradioactive. The stud portion of the wire 3100 can itself be radioactive but preferably is nonradioactive and carries radioactive sources, parts, or material. It is preferred that the stud 3108 be the radioactive portion of the wire system and that this radioactive portion be lockably connected to the drive cable 3104. This is most easily accommodated by having the stud 3108 lockably connected to the drive cable 3104. Generally, the drive cable 3104 will have a significantly greater length than the radioactive portion of the wire system.

FIGS. 32, 33*a* and 33*b*, 34*a* and 34*b* show examples of radioactive sources which may be used with the present invention.

Figure 32A:
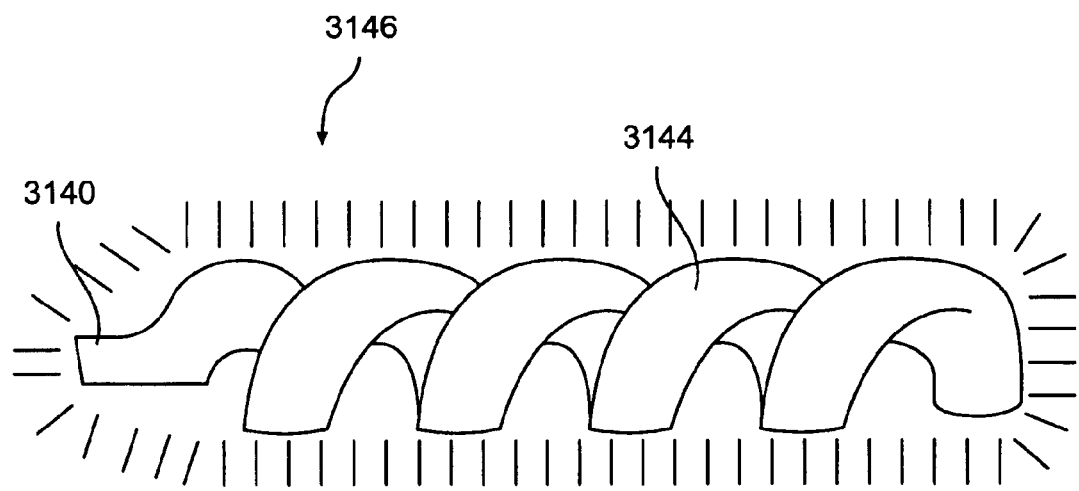
Figure 32B:
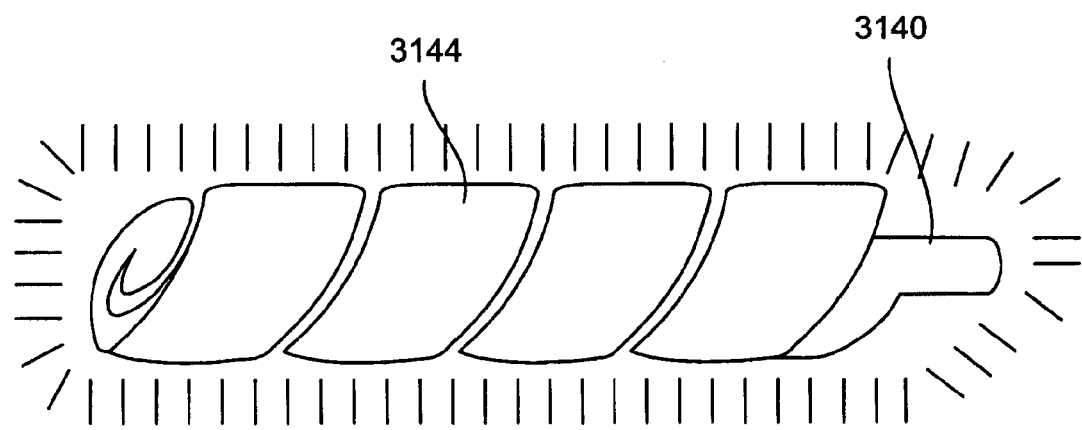

FIGS. 32*a* and 32*b* are radioactive coil sources 3146. Each radioactive coil source 3146 fits over a stud 3108. The radioactive coil 3146 has an alignment end 3140 and a coil segment 3144. The alignment end 3140 may be fitted into a slot on the drive cable 3104 or stud 3108 such as that shown in FIG. 31*a*. The coil segment 3144 fits over a stud 3108 such as that shown in FIG. 31a. The coils 3144 may be held in place by the stud 3108, stud head 3116, or a stopper 3120.

FIG. 32b depicts a more tightly wound coil than FIG. 32a. Many variations in the coil design are possible.

Figure 32C:
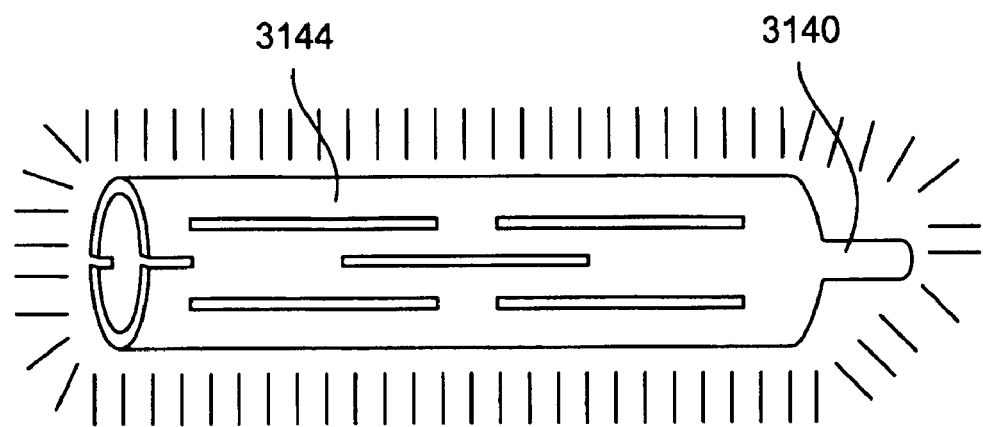
Figure 32D:
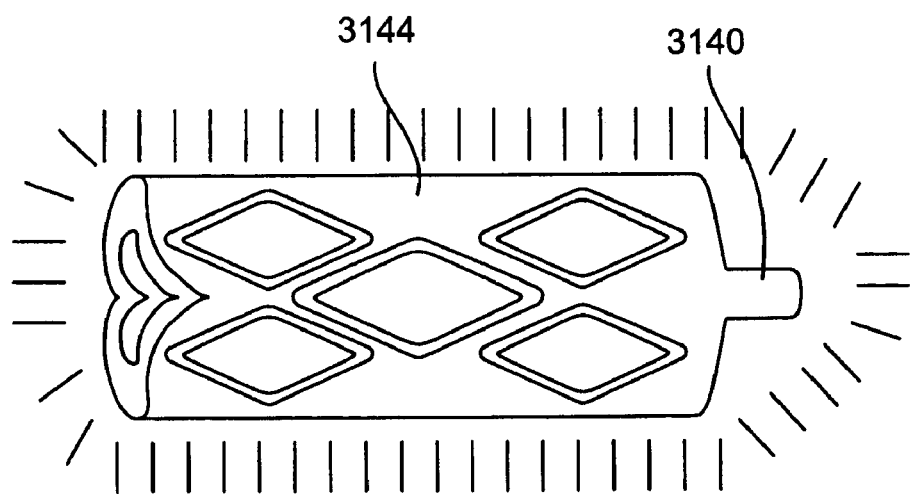

Also, FIGS. 32c and 32d depict two other designs for radioactive sources which may be used to fit over a stud 3108. Various designs may be used such as cylindrical, roller, tubular, net, and stent shaped designs. Opposite the alignment end 3140, FIGS. 32c and 32d show clefts or crevices that can be used to lock the radioactive source in place. The radioactive sources may be locked into place using external pressure and/or by the stud or other material filling the cleft, crevice, or tip of the radioactive source.

FIG. 33a shows a doughnut or washer-shaped radioactive source which can be fit over a stud 3108. The doughnut or washer-shaped source has a cylindrical-shaped body 3148 and a hollowed out opening or hole 3152. A cross-sectional view of the doughnut or washer-shaped radioactive source is shown in FIG. 33b. Various radioactive materials can be used with the doughnut or washer shaped sources. The radioactive sources may have mechanical means to lock the source to a drive cable or other source in a chain of sources.

FIG. 34a shows a longer shaped cylindrical tube for carrying a radioactive source. FIG. 34b shows a cross-sectional view of such a cylindrical shaped radioactive source. The cylinder shown in FIGS. 34a and 34b is preferably formed of a metal or plastic material and filled with a radioactive source. The radioactive source within the cylinder may take a liquid, gel, or solid form. The cylinder has a long cylindrical body 3156 and a hollowed out inner section or hole 3160. Preferably, the diameter of the cylinder is the same or smaller than the drive cable, or nonradioactive portion. The cylinder is empty or void within the cylindrical shaped portion 3156 and can be filled with radioactive material. The cylinder may be filled with liquids, gels, microseeds or seeds of radioactive material. For example, strontium seeds may be placed in the cylinder. In such a configuration the wire transport system of the present invention can transport microseeds or seeds to the patient area to be treated. These microseeds or seeds can be safely encapsulated in a cylinder.

FIGS. 35a and 35b show embodiments of the present invention using a drive cable 3104 or nonradioactive portion and a radioactive portion. Specifically, in FIGS. 35a and 35b there is a stud 3108 connected to the drive cable 3104 (which may be formed of one metal) carrying radioactive parts. More specifically, the stud 3108 is carrying doughnut-shaped or washer-shaped radioactive parts and the head of the stud 3108 is capped with a stopper 3120. Also, it is preferred that a cover 3164 is used in both embodiments.

In the particular embodiment shown in FIG. 35a, six spaced apart doughnut or washer radioactive sources or radioactive parts 3148 are fit over the stud 3108. The radioactive parts 3148 are spaced apart along the length of the stud 3108. Spacers or other material providing spaces between the radioactive parts 3148 may be used. In this particular embodiment, the stud head 3116 is threaded or has a ridged surface so that the stopper 3120 may be snapped on or fitted over the stud head 3116. Also, in this embodiment, the stopper 3120 holds the radioactive parts 3148 and spacers in place on the stud.

Using this configuration of stud 3108 with radioactive parts 3148 fitting over the stud 3108, the number of radioactive parts 3148, such as doughnuts or washers, can be increased or decreased. If the number of doughnuts or washers is decreased, additional spacers may be needed to form a tight fit along the length of the stud 3108 capped by the stopper 3120. By increasing or decreasing the number of radioactive parts 3148 fitting over the stud 3108 the radioactivity of the wire system may be changed. In the preferred embodiment, each radioactive part is locked into position so it cannot be dislodged and lost. The locks may take various mechanical forms.

FIG. 35b shows an embodiment similar to FIG. 35a but with less space (little or no space) between radioactive parts 3148. No spacers are needed for the embodiment of FIG. 35b. The radioactive waves emitted by the embodiment of FIG. 35b may be more uniform than that shown in FIG. 35a.

FIGS. 36a, 36b and 36c show other embodiments of the wire system of the present invention. FIGS. 35, 36a, 36b and 36c show a drive cable 3108 with a slot 3160, an alignment end 3140, coils 3144, a stud 3108, a stud head 3116, a stopper 3120 and a cover 3164. In this configuration of the wire system, the radioactive part is a coil part 3146 as shown in FIG. 32. The coil part 3146 has an alignment end 3140 which fits into a slot on the drive cable 3160. The coil part 3146 fits over the stud 3108 between the connection of the stud to the drive cable 3108 and the stud head 3116. A stopper 3120 is supplied to maintain the radioactive part, the coil 3146, fixed in place over the stud 3108. Alternatively, the coil part 3146 or other radioactive source may be soldered into place.

Also, in this embodiment a cover 3164 is placed over the radioactive portion. The cover 3164 fits between the drive cable 3108 and the stopper 3120 and is preferably made of a plastic material. The cover 3164 is optional and is used to ensure a smooth outer finish to the radioactive portion of the wire system. The cover 3164 may be made of plastic or metallic material and it isolates the radioactive material of the system as an additional security measure to prevent the loss of any radioactive material during use or manipulating of the wire system. When the radioactive material being used is a beta emitter, the material for the cover 3164 must not block or stop the energy of the beta emitter. Therefore, the material must be a thin metallic cover or plastic material which does not absorb or inhibit the beta emissions.

Instead of, or in addition to the cover shown in FIGS. 35a, 35b and 36, a retractable sleeve generally in the same shape as the cover may be used. Like the cover, the sleeve is near the end or point, but the sleeve can be retracted or pulled back and away to uncover or expose the radioactive source. The sleeve should be about 0.1 mm over the wire. The sleeve should allow spacing for movement. A wire may be used to move or pull-back the sleeve.

FIG. 37 shows another embodiment of the present invention including a drive cable 3104, a stud 3108, radioactive parts in the form of doughnuts or washers 3148, a spacer 3168 and a stopper 3120'. In this particular embodiment, the stud 3108 has a stud head 3116 which has a diameter that is the same as or smaller than the stud itself. In particular, in this embodiment the stopper 3120' fits in or is connected to the body of the stud. The stopper 3120' holds the spacers and radioactive parts in place on the stud 3108. In this embodiment the radioactive parts 3148 can be slid into place over the stud 3108. The spacer 3168 can be placed over the stud 3108 just prior to the placement of the stopper 3120'.

FIG. 38 is another embodiment of the present invention that uses a push in and lock connection for connecting the stud 3108' to the drive cable 3104. In this embodiment, the radioactive parts are cylinders or doughnuts 3148 which fit over the stud 3108'. The stud head 3116 is large enough to hold the doughnuts and washers 3148 along with spacers in place. Preferably a cover 3164 is also used with this embodiment.

To form the push in and lock connection a female receptacle 3172 is provided at the terminal end of the drive cable 3104. One end of the stud, the end opposite the stud head 3116 a male terminal 3176 is used. The female receptacle 3172 of the drive cable 3104 and the male terminal 3176 of the stud 3108 may take a variety of forms. However, it is preferred that the connection be of the type that the stud 3108 may simply be pushed in and locked into position. Various teeth or laches may be used in this push in and lock connection.

In this embodiment, the radioactive parts or sources 3148 are placed on the stud prior to locking the stud 3108 in place.

FIG. 39 is another embodiment using a push in and lock connection. FIG. 39 also includes a drive cable 3104, stud 3108, stud head 310, a female receptacle 3172', a male terminal 3176', and a cover 3164. However, the embodiment shown in FIG. 39 uses a cylinder 3156 filled with radioactive material as the radioactive part (which is fit over the stud 3108). The push in and lock connection shown in FIG. 39 is a variation of the push in and lock connection shown in FIG. 38.

The various embodiments shown such as FIGS. 35*a*, 35*b*, 36, 37, 38, and 39, may include material on either side of the radioactive source to assist in locating the source on a monitor during a procedure. Specifically, radiological marks, or radiopaque material can be used to highlight the two ends of the radioactive source. This assists with orientation of the radioactive source during the procedure.

FIGS. 40*a* through 40*c*, 41*a* through 41*f*, and 42*a* through 42*f*, and 43*a* through 43*c* show different types of pins, locks or stoppers that are placed on the end of the stud 3108 away from the drive cable 3104 to lock the radioactive parts 3148 in place on the drive cable 3104.

FIG. 40*a* shows a threaded or ridged stud head 3116' on a stud 3108 attached to a drive cable 3104. FIG. 40*b* shows a cross-sectional view of a stopper 3120 to be used on a threaded or ridged stud head 3116' shown in FIG. 40*a*. FIG. 40*c* shows the stopper 3120 placed over the threaded or ridged stud head 3116' shown in FIG. 40*a*. This configuration of stud head 3116' and stopper 3120 serves as a lock at the end of the stud head 3116' locking into position any radioactive parts 3148 or spacers or other items which are placed on the stud 3108. (For example, as shown in FIG. 35). Other types of mechanical locks are possible for the stopper 3120 and stud head 3116.

Alternatively, the stopper 3120 and stud head 3116 may be fused or soldered together. Using, for example, heat and/or electricity, the stopper 3120 and stud head 3116 may be fused into place. Also, a metal solder could be used. This would limit any possibility that the radioactive portions would come loose or undone.

Figure 41A:
Figure 41B:
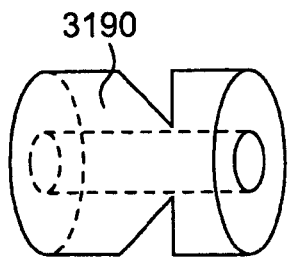
Figure 41C:
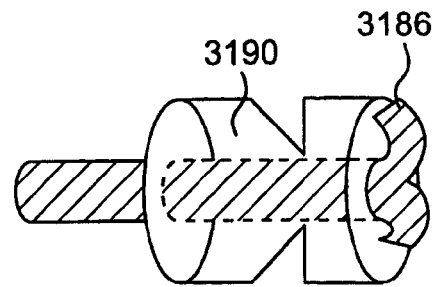
Figure 41D:
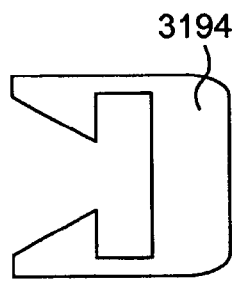
Figure 41E:
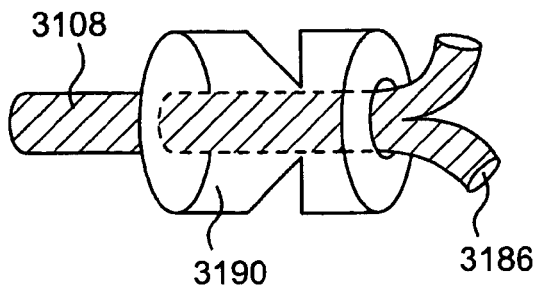
Figure 41F:
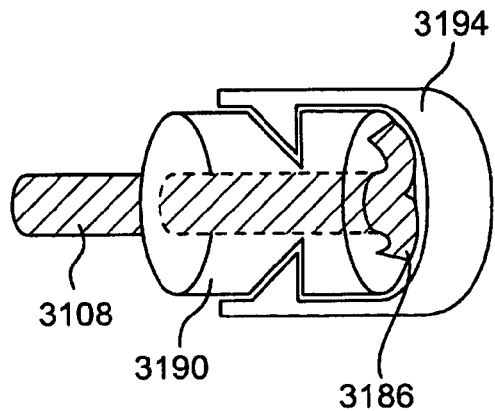

FIGS. 41*a* through 41*f* show an alternative embodiment to lock radioactive parts 3148 in place on a stud 3108. FIG. 41*a* shows a stud 3108 with a split end 3186 attached to a drive cable 3104. Instead of a stud head 3116, the stud shown in FIG. 41*a* has a split end 3186 at that end which is opposite the connection to the drive cable 3104. A split end pin 3190 is shown in FIG. 41*b*. This split end pin 3190 is positioned over the split end 3186 as shown in FIG. 41*c* and 41*e*. As shown in FIG. 41*e*, after the split end pin 3190 is placed over the split end 3186 of the stud 3108, the split ends 3186 of the stud 3108 are separated. As shown in FIG. 41*c*, the split ends 3186 are separated and pushed apart until they make contact with the split end pin 3190 and form a lock against the split end pin 3190. A pin cap 3194 shown in FIG. 41*d* is then placed over the split end pin 3190 as shown in FIG. 41*f* as an added safety precaution. The split end pin cap 3194 is an optional element of the system.

When using the configuration shown in FIGS. 41*a* through 41*f*, the radioactive parts are preferably placed on or over the stud 3108 along with any spacers desired prior to mounting the split end pin 3190 and split end cap 3194 into position. The split end pin 3190 locks the radioactive parts 3148 and spacers in position over the stud 3108.

Figure 42A:
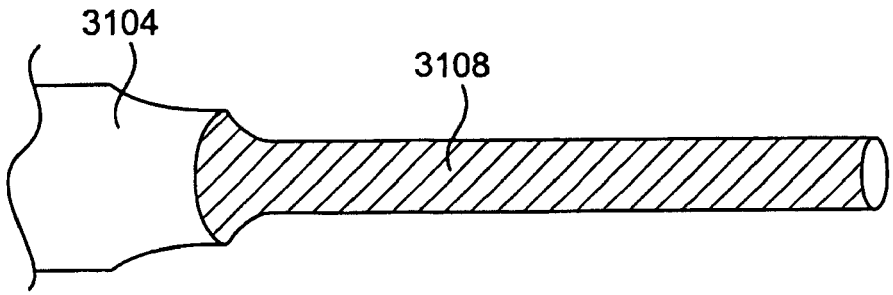
Figure 42B:
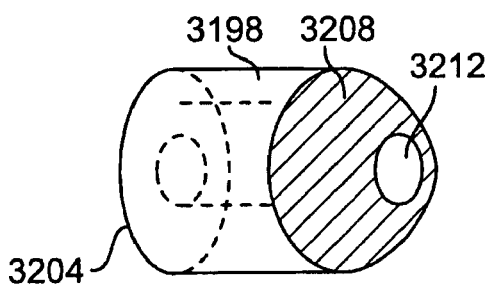
Figure 42C:
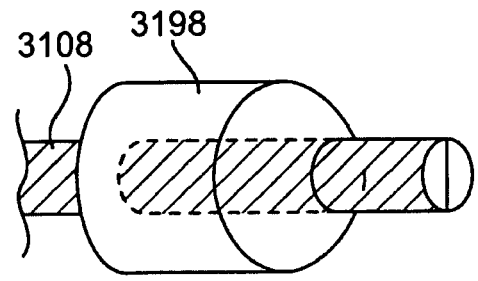
Figure 42D:
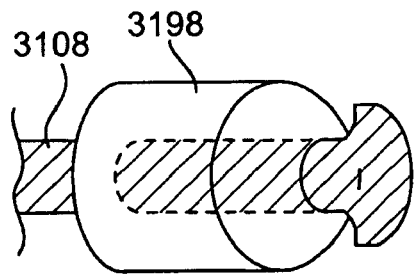
Figure 42E:
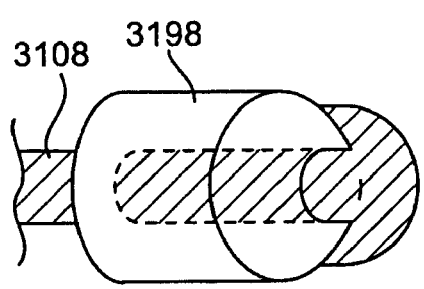

FIGS. 42*a* through 42*e* show an alternative embodiment to the split end pin 3190. Stud end pin 3198 shown in FIG. 42*b* fits over a stud 3108 shown in FIG. 42*a*. The stud end pin 3198 is formed in the shape of a rubber gasket or rubber washer having a generally cylindrical shape. Preferably, one end or side of the stud end pin 3198 is flat 204 while the second end or side is a rounded or pointed 208 and shaped away from the hole 212 in the center. This stud end pin 3198 is placed over the stud as shown in FIG. 42*c* and then the shape or form of the end of the stud 3108 is changed. Specifically, as shown in FIG. 42*d*, the end of the stud 3108 away from the drive cable 3104 may be flattened, opened or widened, in any fashion, so as to lock the stud end pin 3198 in place at the end of the stud 3108 (which is away from the drive cable 3104). FIG. 42*d* and FIG. 42*e* show different shapes of the stud end 3108 which allow the stud end pin 3198 to be locked into place.

FIGS. 43*a* through 43*c* show an alternative embodiment for use with a stud 3108, stud head 3116" and a stopper 3120. Specifically, a stud 3108 with a stud head 3116" in the shape of a male terminal 3176 (on one end) and a second end being connected to the drive cable 3104 is shown. A stopper 3120 having an inside or internal shape for a female receptacle 3172 is shown in FIG. 43*b*. FIG. 43*c* shows the stopper 3120 placed over the stud head 3116" and forming a lock on the end of stud 3108 to maintain any radioactive parts 3148 or spacers on the stud 3108.

FIGS. 44*a* through 44*f*, FIG. 45, and FIGS. 46*a* through 46*b* are alternative embodiments that use a nonradioactive wire portion and radioactive portion 3312 but do not use a stud 3108. These embodiments use a drive cable 3104 which is nonradioactive or substantially nonradioactive and a connected or attached second portion of the wire which is radioactive and/or contains radioactive parts 3312. These embodiments show that there are various methods for attaching the radioactive portion and nonradioactive portion as well as various methods for the radioactive portion to carry radioactive sources or radioactive parts 3312.

FIGS. 44*a* through 44*f* show an embodiment that uses a push in connection to connect the radioactive portion with the nonradioactive portion of the wire system. Specifically, a drive cable 3104 is used with a female receptacle 3172. The female receptacle 3172 accepts a male terminal 3178 from the radioactive portion to connect the radioactive portion to the drive cable 3104.

In this embodiment, as well as those shown in FIGS. 45 and 46, the radioactive sources or parts 3312 fit inside a casing or housing which makes up the body of the radioactive portion, instead of the radioactive sources or parts 3312 fitting over a stud 3108.

Figure 44A:
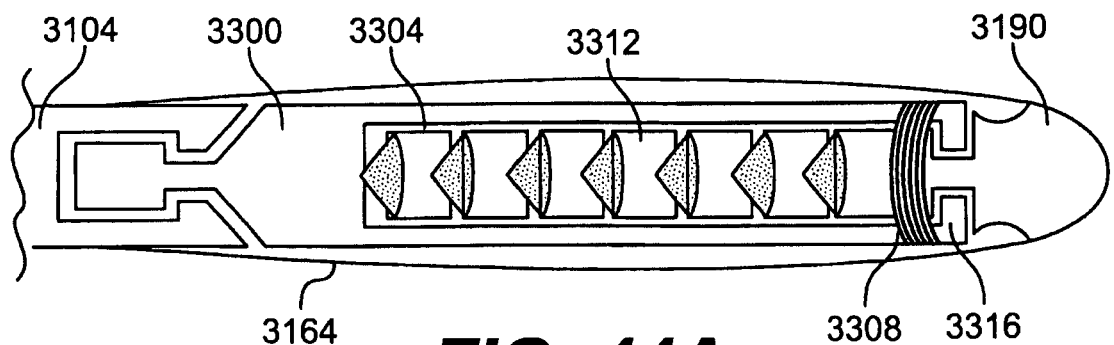

In FIG. 44*a* the casing or housing 3300 has an interior opening 3304 for holding radioactive sources or radioactive parts 3148.

The radioactive portion of this embodiment is made up of the casing or housing 3300 with interior section 3304, radioactive parts 3148, a pin 3190", a wrapping 3308 and a cover 3164. The radioactive portion is configurable by placing different radioactive parts 3148 or spacers within the interior opening 3304 of the casing 3300. Preferably, the radioactive parts 3148 and spacers are held in place by a pin 3190" which secures the end of the radioactive portion and is wrapped in place by wrap 3308. Variations of the casing 3300 and pin 3190" are shown in FIGS. 44*b* and 44*d*.

Figure 44D:
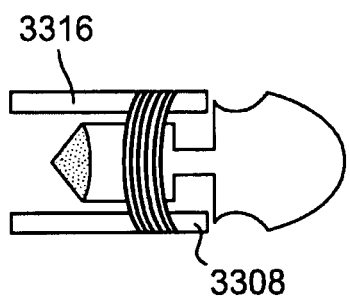
Figure 44B:
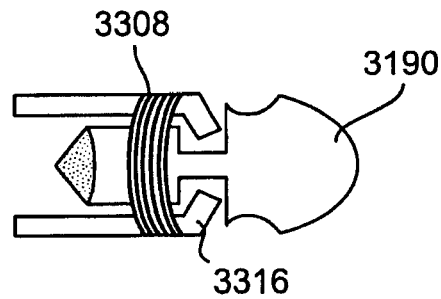
Figure 44E:
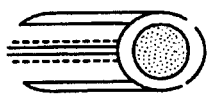
Figure 44C:
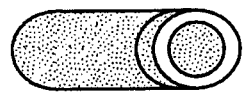

After placing the radioactive parts 3312 and spacers (not shown) in the interior 3304, the pin 3190" is then placed into position as shown in FIG. 44*d*. FIG. 44*e* shows a cross-sectional view of the radioactive portion shown in FIG. 44*d*. At this point, the pin 3190" may be left as shown in FIG. 44*d* or the walls of the casing 3300 or the walls 3316 of the casing 3300 may be partially bent as shown in FIG. 44*b*. The cross sectional view for FIG. 44*b* is shown in FIG. 44*c*. Or, in yet a third embodiment or variant, the walls 3316 may be bent to nearly a 90° angle or a 90° angle as shown in FIG. 44*a*.

Figure 44F:

FIG. 44f shows an example of the radioactive parts 3312 which can be used in the interior 3304 of casing 3300. It is preferred that the radioactive parts 3312 for this type of an interior held embodiment, generally have a conically-topped cylinder shape or a pentagonal pyramid shape. These shapes are preferred over other shapes because of their ability to interlock. Specifically, FIG. 44f shows a radioactive part 3312 with a conically-shaped top and a hollowed bottom to receive another conically-shaped radioactive part 3312 within, so that the parts 3312 are interlocking.

FIG. 45 shows another alternative embodiment for a radioactive portion that does not use a stud 3108. FIG. 45 is a variation of the embodiment shown in FIG. 44a. The embodiment of FIG. 45 generally uses a similar configuration to the embodiment shown in FIG. 44a except a different connection is used between the radioactive portion 3312 and the nonradioactive portion or the drive cable 3104. Specifically, the drive cable 3104 in FIG. 45 ends in a male terminal 3176 and the casing 3300' shown in FIG. 45 accepts the male terminal 3176 of the drive cable 3104 within the interior of the casing 3304. Thus, the male/female role of the connection between the drive cable 3104 and the radioactive portion 3312 is reversed from that shown in FIG. 44a.

The male terminus 3320 of the drive cable 3104 is preferably formed with a conical-shaped opening at the very end. This conical-shaped opening accepts the conical-shaped top of the first radioactive part 3312 which will rest up against the male terminus 3320. In this way, the male terminus 3320 and the interlocking radioactive parts 3312, as well as the conically-shaped tip of the pin 3190" are all locked securely together. A wrap 3308 may be used on either end of the radioactive portion (shown in FIG. 45) to hold the walls 3316 of the casing 3300 from spreading apart. These wrappings 3308 are optional.

FIGS. 46a through 46g show two alternative embodiments of a radioactive portion which does not use a stud 3108. The embodiments shown in FIGS. 46a and 46g are similar to the embodiment shown in FIG. 45 with the primary exception being that the radioactive part 3312' is a generally a hallow cylindrical-shaped part which is filled with radioactive material. The radioactive material held by the radioactive part 3312' may be solid, liquid or gel. It is preferred in this embodiment that the cylindrically-shaped radioactive part 3312' have conical ends 3328 to assist in locking the radioactive part 3312' into position between the male terminus 3320 of the drive cable 3104 and the inner portion of the pin 3190'". To accommodate this, the inner portion of the pin has a female receptacle 3172 to accept the conical-shaped end 3328 of the radioactive part 3312', cylinder. Although the cylinder is shown with outwardly-shaped conical ends, the cylinder may be shaped so that the conical ends 3328 are removed or are inwardly shaped.

FIGS. 46b and 46e show an expanded view of the conically-shaped radioactive part 3312. In most other respects, the embodiments shown in FIGS. 46a and 46g are generally similar to that shown in FIG. 45 with drive cable 3104, male terminus 3320, casing 3300 with casing walls 3316, an interior area 3304, a radioactive part 3312, a pin 3190", optional wrappings 3308 and optional cover 3164.

The radioactive parts 3312' can be singular or assembled one after another in series and remain securely locked in place as shown in FIG. 46a.

In these embodiments, wraps of plastic or metallic bands or nets may be used to secure the radioactive parts 3312' in place in the radioactive portion. Preferably after the radioactive portion is assembled or connected to the drive cable 3104, the entire structure is covered with a cover 3164 made of metallic or plastic material that can isolate and seal the outer portion of the drive cable 3104 connection and radioactive portion 3312'.

FIG. 46c shows a drive end cable design 3104. FIG. 46d shows an alternative design for a pin 3190". FIG. 46e is an alternative design for a radioactive source.

FIG. 46f depicts a hollow shaped holding device for the radioactive part 3312 to fit inside.

In use, when the radioactive source 3312' is a high activity source or a gamma emitter, a mechanical delivery system is required, preferably, robotic source handling is used. Preferably an after loader system is used with both an active and a simulation wire which moves the wires with independent drive systems.

If a beta emitter source is used in the wire system, a robotic or mechanical delivery system may not be needed. Preferably, a special catheter that permits accurate site placement is used. It is also preferred that the manual system which is used to move the wire having the beta source shields the operator from the radiation. Also, a chronometer for controlling the radioactive exposure time may be used. Any manual-type system for advancing the wire into a catheter should be responsive to the operator's inputs.

A person of ordinary skill in the art would realize there are many variations to the above-described invention that are possible.

What is claimed is:

1. A catheter assembly, comprising:
   (a) a flexible tubular catheter body having an inner lumen; and
   (b) at least one fluid communication structure integrally formed on the catheter body, wherein the at least one fluid communication structure comprises:
   at least one bulk formed on the catheter body; and
   at least one conduit formed on the bulk, wherein the at least one conduit is adapted to permit fluid flow through a biological path; and
   where the at least conduit can have around the whole or partial periphery open channels and wherein the open channels are covered by a membrane.

2. The catheter of claim 1, wherein the catheter has a plurality of bulks on the catheter body.

3. The catheter of claim 2, wherein each bulk has a length, the length of each bulk being approximately three to seven millimeters.

4. The catheter of claim 1, further comprising at least one market attached to the catheter body, wherein the market enables a user to position a radiating source within a biological path.

5. The catheter of claim 1, further comprising at least one balloon attached to a distal end of the outer surface of the catheter body.

6. The catheter of claim 5, wherein the at least one balloon extends over the at least one bulk.

7. The catheter of claim 6, wherein the at least one balloon extends over each conduit on a bulk such that the path for the fluid is formed by the conduit and the balloon.

8. The catheter of claim 6, wherein a balloon control communicates with the balloon through the inner lumen or micro conduits.

9. The catheter assembly of claim 1, wherein the catheter includes a valve.

10. The catheter of claim 9 wherein the value is a U-shaped metallic valve built into a lumen or channel of the catheter.

11. The catheter of claim 9 wherein the catheter has multiple valves.

12. The catheter assembly of claim 1, wherein the catheter further comprises a pressure monitor or a blood pressure monitor.

13. The catheter assembly of claim 1, wherein the catheter further comprises a marker.

14. The catheter of claim 13 wherein the market is for visually marking the catheter with visual monitoring equipment.

15. The catheter assembly of claim 1, further comprising a stent or membrane for maintaining a cell wall.

16. The catheter assembly of claim 1, further comprising a guidewire.

17. The catheter of claim 16 further comprising a second guidewire, wherein at least one of the guidewires is made of nickel alloy.

18. The catheter assembly of claim 1, further comprising an over-the-wire guidewire.

19. The catheter assembly of claim 1, wherein a guidewire may be removed from the catheter and another wire placed into the catheter.

20. A catheter assembly, comprising:
    (a) a flexible tubular catheter body having an inner lumen and a guidewire channel;
    (b) a guidewire disposed within the guidewire channel for selectively positioning the catheter body;
    (c) a first balloon structure attached to a distal end of the catheter body, wherein the balloon is in communication with a balloon control through micro conduits, where at least one micro conduit can have around the whole or partial periphery open channels and wherein the open channels are covered by a membrane;
    (d) a guidewire exit port in communication with the guidewire channel; and
    (e) at least one perfusion hole at a proximal side of the first balloon structure and at least one perfusion hole at a distal side of the first balloon structure to permit fluid flow through a biological path.

21. The catheter assembly of claim 20, further comprising a second balloon enveloping the first balloon structure.

22. A catheter for use in biological paths to provide fluids and/or gases perfusion along the length of the catheter when inserted in a biological path, wherein the catheter comprises two or more integral concentric or non concentric conduits and one or more balloons attached to a more exterior conduit; a more interior conduit used for placing devices used in catheter operations; the more exterior conduit for providing a track for fluids and/or gases without substantially obstructing fluid flow through the biological paths when the one or more balloons are inflated, wherein the one or more balloons, when inflated, provide a wall for the more exterior conduit and where the at least conduit can have around the whole or partial periphery open channels and wherein the open channels are covered by a membrane.

23. The catheter according to claim 22, where the balloon constitutes a concentric or non concentric most external conduit with respect to the interior and exterior conduits.

24. The catheter according to claim 22, where around the whole or partial periphery and at specific location of the exterior conduit are attached one or more balloons.

25. The catheter according to claim 22, where the balloon prolongate along the entire length of the exterior conduit.

26. The catheter according to claim 25, where the ends of the balloons are attached to distal locations of the edges of the external conduit.

27. The catheter according to claim 22, where the balloons are located at specific locations along the entire length of the exterior conduit.

28. A catheter for use in biological paths to provide fluids and/or gases perfusion along the length of the catheter when inserted in a biological path, wherein the catheter comprises two or more integral concentric or non concentric conduits; a more interior conduit used for placing devices used in catheter operations; a more exterior conduit for providing a track for fluids and/or gases without substantially obstructing fluid flow through the biological paths, wherein the catheter provides a continuous wall for the more exterior conduit and where the exterior conduit can have around the whole or partial periphery open channels and wherein the open channels are covered by a membrane.

29. The catheter according to claim 28, where the exterior conduit permits positioning a radiation and/or radioactive source at a desirable distance from the biological paths.

30. The catheter according to claim 28, where the exterior conduit supports the walls of the biological paths.

31. The catheter according to claim 28, where the exterior conduit is of flexible material.

32. The catheter according to claim 28, where the exterior conduit prolongate along the entire length of the interior conduit.

33. The catheter according to claim 28, where the exterior conduit are segments of conduits located along the entire length and/or at specific locations of the interior channel.

34. The catheter according to claim 28, where the exterior conduit have perpendicular to its cross section micro-conduits and/or pores.

35. The catheter according to claim 34, where the cross section of the micro-conduits and/or pores are parallelepites of regular or irregular shape.

36. The catheter according to claim 35, where the cross section of the micro-conduits and/or pores are circles, ellipses and/or rectangles.

37. The catheter according to claim 34, where the micro-conduits and/or pores are arranged in an ordered manner and/or non-ordered manner.

38. The catheter according to claim 28, where the interior conduits are used for introducing devices used in catheter operations.

39. The catheter according to claim 38, where the devices used in catheter operations are guidewires.

40. The catheter according to claim 28, where the exterior conduit can have around the whole or partial periphery open channels.

41. The catheter according to claim 40, where the walls of the open channels have regular or irregular shape.

42. The catheter according to claim 40, where the open channels are arranged in an ordered manner and/or non-ordered manner.

43. The catheter according to claim 34, where said external conduits having on its outer surface pores which extend from said outer surface to the above mentioned micro-conduits, said pores being oriented at whatever desired angle with respect to the micro-conduits.

44. The catheter of claim 33, wherein the segments and the space between the segments are covered by a membrane.

45. The catheter of claim 40, wherein the open channels are covered by a membrane.

\* \* \* \* \*